(12) United States Patent
Yang et al.

(10) Patent No.: US 11,680,121 B2
(45) Date of Patent: Jun. 20, 2023

(54) CATALYST SYSTEMS AND PROCESSES FOR POLY ALPHA-OLEFIN HAVING HIGH VINYLIDENE CONTENT

(71) Applicant: ExxonMobil Chemical Patents Inc., Baytown, TX (US)

(72) Inventors: Jian Yang, Houston, TX (US); Jo Ann M. Canich, Houston, TX (US); Hua Zhou, Missouri City, TX (US); Jennifer L. Rapp, Houston, TX (US)

(73) Assignee: ExxonMobil Chemical Patents Inc., Baytown, TX (US)

(*) Notice: Subject to any disclaimer, the term of this patent is extended or adjusted under 35 U.S.C. 154(b) by 25 days.

(21) Appl. No.: 17/348,546

(22) Filed: Jun. 15, 2021

(65) Prior Publication Data

US 2022/0106422 A1    Apr. 7, 2022

Related U.S. Application Data

(62) Division of application No. 16/270,085, filed on Feb. 7, 2019, now Pat. No. 11,084,894.

(60) Provisional application No. 62/732,311, filed on Sep. 17, 2018, provisional application No. 62/629,200, filed on Feb. 12, 2018.

(51) Int. Cl.
  *C07C 2/30*    (2006.01)
  *C07C 2/32*    (2006.01)
  *C08F 4/6592*  (2006.01)
  *C08F 210/16*  (2006.01)
  *C08F 4/659*   (2006.01)

(52) U.S. Cl.
  CPC ............ *C08F 210/16* (2013.01); *C07C 2/30* (2013.01); *C07C 2/32* (2013.01); *C08F 4/65908* (2013.01); *C08F 4/65912* (2013.01); *C08F 4/65922* (2013.01)

(58) Field of Classification Search
  CPC .......... C07C 2/30; C07C 2/32; C08F 4/65925
  See application file for complete search history.

(56) References Cited

U.S. PATENT DOCUMENTS

| | | | | |
|---|---|---|---|---|
| 5,284,988 A | * | 2/1994 | Schaerl, Jr. | C10G 50/02 585/16 |
| 2008/0146469 A1 | * | 6/2008 | Sato | F16C 33/109 384/100 |

* cited by examiner

*Primary Examiner* — Caixia Lu
(74) *Attorney, Agent, or Firm* — ExxonMobil Technology and Engineering Company-Chemicals

(57) ABSTRACT

A process for making a poly alpha-olefin (PAO) having a relatively high vinylidene content (or combined vinylidene and tri-substituted vinylene content) and a relatively low vinyl and/or di-substituted vinylene content, as well as a relatively low molecular weight. The process includes: contacting a feed containing a $C_2$-$C_{32}$ alpha-olefin with a catalyst system comprising activator and a bis-cyclopentadienyl metallocene compound, typically a cyclopentadienyl-benzindenyl group 4 transition metal compound.

12 Claims, 2 Drawing Sheets

CATALYST SYSTEMS AND PROCESSES FOR POLY ALPHA-OLEFIN HAVING HIGH VINYLIDENE CONTENT

PRIORITY CLAIM

This application is a divisional application of U.S. application Ser. No. 16/270,085 filed Feb. 7, 2019, which claims priority to and the benefit of U.S. Ser. No. 62/629,200, filed Feb. 12, 2018, and U.S. Ser. No. 62/732,311, filed Sep. 17, 2018 the disclosures of which are incorporated herein by reference in their entireties.

STATEMENT OF RELATED APPLICATIONS

This application is related to U.S. Ser. No. 15/706,088, filed Sep. 15, 2017 (which is published as WO 2018/0094088.

This application is also related to U.S. Ser. No. 15/921,757, filed Mar. 15, 2018 (which is published as WO 2018/182982.

FIELD OF THE INVENTION

The present invention relates to poly alpha-olefin (PAO) materials and processes for making them. In particular, the present invention relates to ethylenically unsaturated PAO materials and saturated PAO materials derived from polymerization of alpha-olefins in the presence of a catalyst system comprising a metallocene-compound specifically designed to yield a high vinylidene content.

BACKGROUND OF THE INVENTION

This section provides background information related to the present invention which is not necessarily prior art.

Alpha-olefins, especially those containing about 6 to about 20 carbon atoms, and oligomers thereof have been used as intermediates in the manufacture of detergents, lubricants, or other types of commercial products. Longer chain alpha-olefins, such as vinylidene-terminated polydecenes are also known and can be useful as building blocks following functionalization or as macromonomers.

Metallocene catalyst systems are known for polymerizing alpha-olefin polymers and oligomers. For example, U.S. Patent Application Publication No. 2005/0159299 discloses polymerization and oligomerization with catalyst compounds on a specifically treated support and exemplifies polymerization with a catalyst compound of dimethylsilyl bis(2-methyl-4-phenyl-indenyl) zirconium dimethyl on a capped support. Such catalysts however typically produce about 50% vinyl and about 50% vinylidene terminal unsaturations (of the termini that are unsaturated). Another example includes U.S. Pat. No. 8,318,998, which discloses cyclopentadienyl-benzindenyl metallocene compounds useful for production of alpha-olefin polymers, such as ethylene and or propylene polymers, having high allyl chain end content. The Examples in this publication show that the resultant alpha-olefin polymers/oligomers have a proportionally low vinylidene content and a proportionally high vinyl content. U.S. Patent Application Publication No. 2013/0023633 also discloses metallocene compounds and use thereof in making polyolefins having proportionally high vinyl content.

Another example, U.S. Pat. No. 8,748,361, discloses a mixture comprising unsaturated poly alpha-olefin (uPAO) material made from, e.g., oligomerization of alpha-olefins in the presence of metallocene catalysts. It was disclosed in this reference that the uPAOs could comprise, among others, vinyls, vinylenes, di-substituted vinylenes, and tri-substituted vinylenes. The vinyls and vinylidenes are terminal olefins, while the di- and tri-substituted vinylene olefins are internal olefins. In this publication, mixtures of the uPAOs produced from the polymerization step were subsequently hydrogenated by hydrogen using a hydrogenation catalyst. A great majority of the C=C double bonds in the mixture were then hydrogenated to form a substantially saturated, stable, aliphatic PAO mixture which, in turn, can be separated by distillation to obtain a hydrogenated PAO material that is particularly suitable as the basestock for lubricating oil compositions used in various applications. To the extent the presence of C=C bonds in the PAO molecules in a lubricating oil composition is considered generally detrimental to the performance of the oil, especially to the oxidation stability thereof, it is highly desired that the uPAO has an overall composition that would result in saturation of the C=C bonds at a degree as high as possible in the hydrogenation step.

Recently, however, research and development in various chemical fields reveal that the ethylenically unsaturated PAO materials prepared from oligomerization of linear alpha-olefins can be particularly advantageously used as an intermediate for making various specialty chemicals because of the reactivity of the C=C double bond present in molecular structure of the oligomer molecules. For example, various chemical functional groups can be bonded to the carbon backbone of the uPAO molecule when a chemical agent reactive with the C=C bond is allowed to contact the uPAO material. The functional group thus introduced onto the PAO structure can bring about unique properties to the functionalized and saturated PAO molecules.

It has been found that the reactivity of the C=C bonds in vinyls, vinylidenes, di-substituted vinylenes, and tri-substituted vinylenes are different with regard to many chemical functionalization agents. For a specific type of functionalization agent, one or more particular type(s) of olefin(s) may be more desirable than the other(s). In addition, uPAOs having various molecular weight and molecular weight distribution and differing reactivities may be desired for making differing derivatives comprising differing functional groups thereon. It is known that vinylidenes and tri-substituted vinylenes are more reactive than di-substituted vinylenes with many common reagents reactive with C=C double bonds.

WO 2017/188602 discloses at paragraph [117]Me$_2$Si (Me$_4$Cp)(2-Me-benzindenyl)MCl$_2$, where the 2 position on the benzindenyl is methyl.

WO 2012/134720, compound G, discloses 1,3-dimethyl benz[e]indenyl)(Me$_5$Cp)HfMe$_2$.

WO 2018/0094088 discloses benzindenyl compounds such as (1,3-dimethyl benz[e]indenyl)(CpMe$_5$)ZrMe$_2$ and (1,3-dimethyl benz[e]indenyl)(CpMe$_4$)ZrMe$_2$.

Other publications of interest include, but are not necessarily limited to: U.S. application Ser. No. 12/642,453 filed Dec. 18, 2009; Ser. No. 12/533,465 filed Jul. 31, 2009; 61/136,172 filed Aug. 15, 2008; 62/477,683 filed Mar. 28, 2017; 62/477,706 filed Mar. 28, 2017; PCT Publication Nos. WO 95/27717; WO 2009/155471; WO 2009/155472; WO 2009/155510; WO 2009/155517; WO 2017/155149; WO 2012/133717; WO 2018/0094088; WO 2018/182982; U.S. Pat. Nos. 3,367,987; 7,214,745; 8,816,027; 8,669,326; 8,940,839; 8,754,170; 8,426,659; 8,841,397; 8,501,894; 8,669,330; 8,835,563; 8,841,394; 8,399,724; 8,623,974; 8,981,029; 6,403,732; 6,818,585; 7,199,072; US Patent Application Publication Nos. 2018/0094088; 2009/0318644, 2004/0102590; 2017/0233516; Japanese Publication No. JP 2005-336092; JP 2011-037164A; Chinese Publication No. CN 105622807; EP Publication Nos. EP 0 659 756; EP 0 610 851; EP 0 283 739; Korean Publication No. KR 1725004; Rulhoff, Sascha, and Kaminsky, "Synthesis and Characterization of Defined Branched Poly(propylene)s with Different Microstructures by Copolymerization of Propylene and Linear Ethylene Oligomers ($C_n$=26-28) with Metallocenes/MAO Catalysts," Macromolecules 16 2006, pp. 1450-1460; Kaneyoshi, Hiromu et al. "Synthesis of Block and Graft Copolymers with Linear Polyethylene Segments by Combination of Degenerative Transfer Coordination Polymerization and Atom Transfer Radical Polymerization," Macromolecules, 38, 2005, pp. 5425-5435; Teuben et al. (*J. Mol. Catal.*, 62, 1990, pp. 277-87); X. Yang et al. (*Angew. Chem., Int'l Edn.*, Engl., 31, 1992, pp. 1375-1377); Small and Brookhart (*Macromol.*, 32, 1999, pp. 2120-2130); Weng et al. (*Macromol Rapid Comm.*, 2000, 21, pp. 1103-1107); *Macromolecules*, 33, 2000, pp. 8541-8548; Moscardi et al. (*Organomet.*, 20, 2001, pp. 1918); Zhu et al. (*Macromol.*, 2002, 35, pp. 10062-10070 and *Macromol. Rap. Commun.*, 2003, 24, pp. 311-315); Coates et al. (*Macromol.*, 2005, 38, pp. 6259-6268); Rose et al. (*Macromolecules*, 2008, 41, pp. 559-567); and Janiak and Blank (*Macromol. Symp.*, 236, 2006, pp. 14-22).

There remains a need for uPAO materials having a high concentration of vinylidenes (and/or of vinylidenes and tri-substituted vinylenes combined), as well as for processes for, and catalyst systems specifically tailored to, making such uPAO materials.

SUMMARY OF THE INVENTION

This section provides a general summary of the invention, and is not a comprehensive invention of its full scope or all of its features.

One aspect of the invention relates to a process for making a poly alpha-olefin (PAO). The process can include a step of contacting a feed containing a $C_2$-$C_{32}$ alpha-olefin with a catalyst system comprising a metallocene compound in a polymerization reactor under polymerization conditions to effect a polymerization reaction to obtain a polymerization reaction mixture comprising vinylidenes, tri-substituted vinylenes, optionally di-substituted vinylenes, and optionally vinyls. The process can also include a step of obtaining an unsaturated PAO product from the polymerization reaction mixture, with the unsaturated PAO product comprising vinylidenes, tri-substituted vinylenes, optionally di-substituted vinylenes, optionally vinyls, and, optionally, is substantially free of the alpha-olefin feed.

The process can also include a step of obtaining an unsaturated PAO product from the polymerization reaction mixture, wherein the polymerization reaction exhibits a selectivity toward greater than or equal to about 80 mol % vinylidenes, preferably 90 mol % vinylidenes, more preferably 96.5 mol % vinylidenes, based on total moles of vinyls, vinylidenes, di-substituted vinylenes, and tri-substituted vinylenes in the unsaturated PAO product.

This invention relates to a process for making a poly alpha-olefin, PAO, the process comprising: contacting a feed comprising a $C_6$-$C_{32}$ alpha-olefin, with a catalyst system comprising a metallocene compound in a polymerization reactor under polymerization conditions to effect a polymerization reaction to obtain a polymerization reaction mixture comprising vinylidenes, tri-substituted vinylenes, optionally di-substituted vinylenes, and optionally vinyls; and obtaining an unsaturated PAO product from the polymerization reaction mixture, wherein the unsaturated PAO product comprises vinylidenes, tri-substituted vinylenes, optionally di-substituted vinylenes, optionally vinyls, wherein the metallocene compound is represented by formula (F-MC):

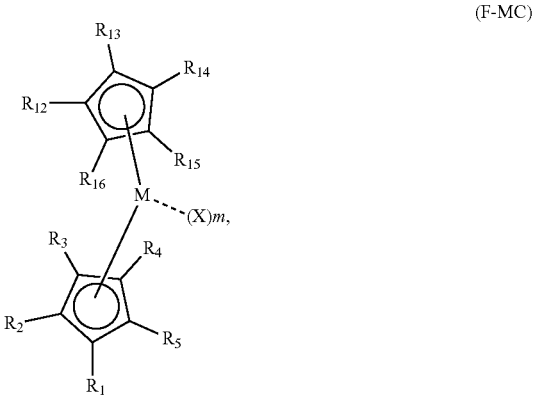

wherein:

each $R^1$, $R^2$, and $R^3$ is, independently, hydrogen or a substituted or unsubstituted linear, branched linear, or cyclic $C_1$-$C_{20}$ hydrocarbyl or silylcarbyl group;

$R^4$ and $R^5$ are each independently a substituted or unsubstituted linear, branched linear, or cyclic $C_1$-$C_{30}$ hydrocarbyl or silylcarbyl group where $R^4$ and $R^5$, taken together with the carbon atoms in the first cyclopentadienyl ring to which they are directly connected, collectively form one or more substituted or unsubstituted rings annelated to the first cyclopentadienyl ring;

$R^{12}$, $R^{13}$, $R^{14}$, $R^{15}$, and $R^{16}$ are each independently a hydrogen, or a substituted or unsubstituted linear, branched linear, or cyclic $C_1$-$C_{20}$ hydrocarbyl, silylcarbyl, or germanyl group, and optionally at least three of $R^{12}$, $R^{13}$, $R^{14}$, $R^{15}$, and $R^{16}$ are not hydrogen;

M is a group 3, 4 or 5 transition metal having an integer coordination number of v, such as 3, 4, or 5;

each X is independently a halogen, a hydride, an amide, an alkoxide, a sulfide, a phosphide, a diene, an amine, a phosphine, an ether, or a $C_1$-$C_{20}$ substituted or unsubstituted linear, branched, or cyclic hydrocarbyl group, or optionally two or more X moieties may together form a fused ring or ring system; and m is an integer equal to v-2, such as 1, 2, or 3.

In some embodiments, the metallocene compound has a structure represented by formula (I):

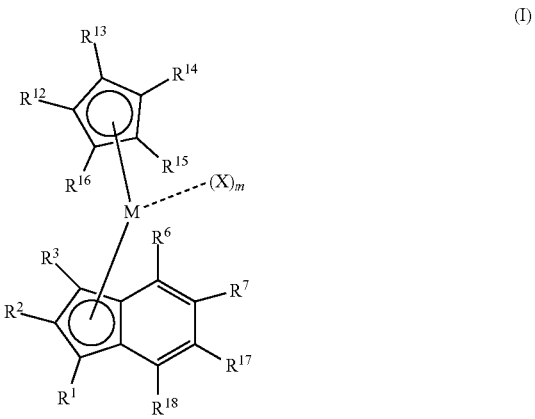

wherein:

each $R^1$, $R^2$, and $R^3$ is, independently, hydrogen or a substituted or unsubstituted linear, branched linear, or cyclic $C_1$-$C_{20}$ hydrocarbyl group, preferably wherein a first one of $R^1$, $R^2$, and $R^3$ is a substituted or unsubstituted linear, branched linear, or cyclic $C_1$-$C_{20}$ hydrocarbyl group; a second one of $R^1$, $R^2$, and $R^3$ is hydrogen; and a third one of $R^1$, $R^2$, and $R^3$ is hydrogen, a substituted or unsubstituted linear, branched linear, or cyclic $C_1$-$C_{20}$ hydrocarbyl group;

$R^6$, $R^7$, $R^{17}$, and $R^{18}$ are each independently hydrogen; a substituted or unsubstituted linear, branched linear, or cyclic $C_1$-$C_{30}$ hydrocarbyl group; or $R^6$ and $R^7$, $R^7$ and $R^{17}$, or $R^{17}$ and $R^{18}$, taken together with the carbon atoms in the indenyl ring to which they are directly connected, collectively form one or more substituted or unsubstituted rings annelated to the indenyl ring;

$R^{12}$, $R^{13}$, $R^{14}$ and $R^{15}$, are each independently a substituted or unsubstituted linear, branched linear, or cyclic $C_1$-$C_{20}$ hydrocarbyl group;

$R^{16}$ is a substituted or unsubstituted linear, branched linear, or cyclic $C_1$-$C_{20}$ hydrocarbyl group or silylcarbyl group;

each X is independently a halogen, a hydride, an amide, an alkoxide, a sulfide, a phosphide, a diene, an amine, a phosphine, an ether, a $C_1$-$C_{20}$ substituted or unsubstituted linear, branched linear, or cyclic hydrocarbyl group, or two or more X moieties together form a fused ring or ring system;

M is a transition metal, preferably group 3, 4 or 5, having an integer coordination number of v, such as 3, 4, or 5; and m is an integer equal to v-2, such as 1, 2, or 3.

Another aspect of the invention relates to a catalyst compound suitable to produce an unsaturated PAO product from $C_6$-$C_{32}$ alpha-olefin under polymerization conditions. In some embodiments, the catalyst compound comprises a polymerization selectivity suitable to form an unsaturated PAO product comprising greater than or equal to about 80 mol % vinylidenes, preferably 90 mol % vinylidenes, more preferably 96.5 mol % vinylidenes, based on total moles of vinyls, vinylidenes, di-substituted vinylenes, and tri-substituted vinylenes in the unsaturated PAO product; represented by the formula (F-MC2):

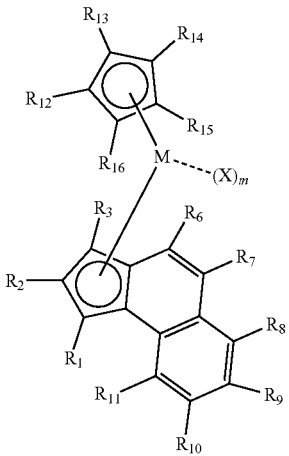

(F-MC2)

in which one of $R^1$, $R^2$, and $R^3$ comprises an alpha Group 14 atom directly attached to the indenyl ring, and a beta Group 14 atom attached to the alpha atom, and two or more, preferably three, substituted or unsubstituted linear, branched linear, or cyclic $C_1$-$C_8$ hydrocarbyl groups attached to the beta atom, optionally two of $R^1$, $R^2$, and $R^3$ are each hydrogen;

$R^6$, $R^7$, $R^8$, $R^9$, $R^{10}$, and $R^{11}$ are each independently a hydrogen or a substituted or unsubstituted linear, branched linear, or cyclic $C_1$-$C_{20}$ hydrocarbyl group;

$R^{12}$, $R^{13}$, $R^{14}$ and $R^{15}$ are each independently a hydrogen, or a substituted or unsubstituted linear, branched linear, or cyclic $C_1$-$C_{20}$ hydrocarbyl group;

$R^{16}$ is a hydrogen, a substituted or unsubstituted linear, branched linear, or cyclic $C_1$-$C_{20}$ hydrocarbyl group or silylcarbyl group;

each X is independently a halogen, a hydride, an amide, an alkoxide, a sulfide, a phosphide, a diene, an amine, a phosphine, an ether, or a $C_1$-$C_{20}$ substituted or unsubstituted linear, branched linear, or cyclic hydrocarbyl group, or two or more X moieties together form a fused ring or ring system;

M is a transition metal, preferably group 3, 4 or 5 having an integer coordination number of v, preferably 3, 4 or 5; and m is an integer equal to v-2, such as 1, 2, or 3.

Another aspect of the invention relates to an unsaturated poly alpha-olefin (PAO) product comprising vinylidenes, tri-substituted vinylenes, optionally di-substituted vinylenes, optionally vinyls. In particular embodiments, the unsaturated PAO product comprises greater than or equal to about 80 mol % vinylidenes, preferably 90 mol % vinylidenes, more preferably 96.5 mol % vinylidenes, based on total moles of vinyls, vinylidenes, di-substituted vinylenes, and ti-substituted vinylenes contained therein.

Further areas of applicability will become apparent from the description provided herein. The description and specific examples in this summary are intended for purposes of illustration only and are not intended to limit the scope of the present invention.

DETAILED DESCRIPTION

Figure 1:
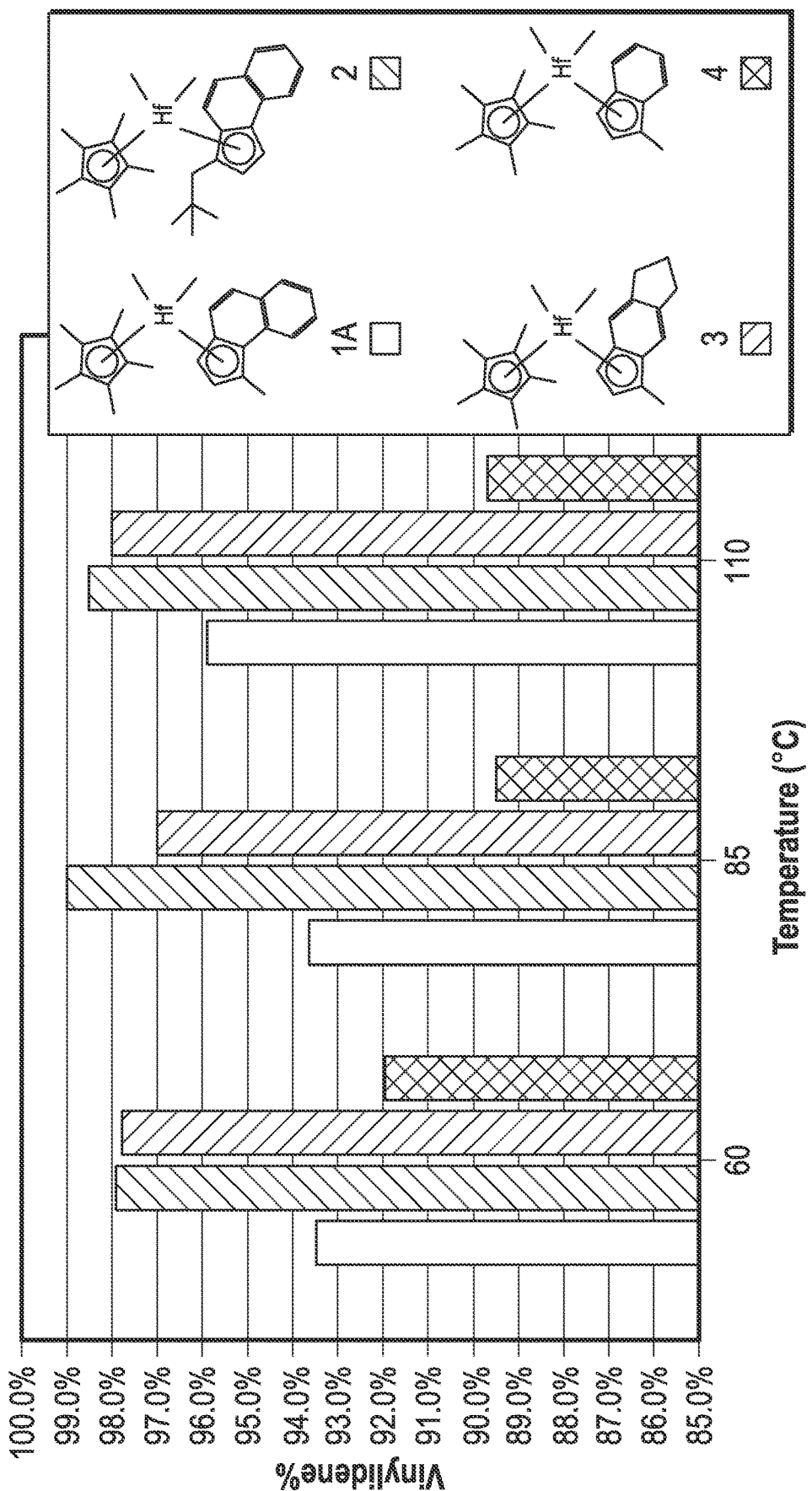
FIG. 1 is a bar graph comparing mole percent vinylidene according to the polymerization temperature of catalysts according to embodiments of the invention.

The term "alkyl" or "alkyl group" interchangeably refers to a saturated hydrocarbyl group consisting of carbon and hydrogen atoms. An alkyl group can be linear, branched linear, cyclic, or substituted cyclic.

The term "branched linear" is defined to mean a branched group that is not dendritic (i.e., branch on branch) or crosslinked, typically a branched linear group is a linear group that has one or more branches, including but not limited to those compounds represented by formula F-V below.

The term "cycloalkyl" or "cycloalkyl group" interchangeably refers to a saturated hydrocarbyl group wherein the carbon atoms form one or more ring structures.

The term "alkenyl" or "alkenyl group" interchangeably refers to a linear unsaturated hydrocarbyl group comprising a C=C bond therein.

The term "cycloalkenyl" or "cycloalkenyl group" interchangeably refers to cyclic hydrocarbyl group comprising a C=C bond in the ring.

The term "aryl" or "aryl group" interchangeably refers to a hydrocarbyl group comprising an aromatic ring structure therein.

Unless otherwise indicated, a substituted group means such a group in which at least one atom is replaced by a different atom or a group. Thus, a substituted alkyl group can be an alkyl group in which at least one hydrogen atom is replaced by a hydrocarbyl group, a halogen, any other non-hydrogen group, and/or a least one carbon atom and hydrogen atoms bonded thereto is replaced by a different group. Preferably, a substituted group is a radical in which at least one hydrogen atom has been substituted with a heteroatom or heteroatom containing group, preferably with at least one functional group, such as halogen (Cl, Br, I, F), $NR^*_2$, $OR^*$, $SeR^*$, $TeR^*$, $PR^*_2$, $AsR^*_2$, $SbR^*_2$, $SR^*$, $BR^*_2$, $SiR^*_3$, $GeR^*_3$, $SnR^*_3$, $PbR^*_3$, and the like or where at least one heteroatom has been inserted within the hydrocarbyl radical, such as halogen (Cl, Br, I, F), O, S, Se, Te, $NR^*$, $PR^*$, $AsR^*$, $SbR^*$, $BR^*$, $SiR^*_2$, $GeR^*_2$, $SnR^*_2$, $PbR^*_2$, and the like, where $R^*$ is, independently, hydrogen or a hydrocarbyl.

The terms "hydrocarbyl radical," "hydrocarbyl group," or "hydrocarbyl" interchangeably refers to a group consisting of hydrogen and carbon atoms only. A hydrocarbyl group can be saturated or unsaturated, linear or branched linear, cyclic or acyclic, aromatic or non-aromatic.

Substituted hydrocarbyl radicals are radicals in which at least one hydrogen atom has been substituted with a heteroatom or heteroatom containing group, preferably with at least one functional group, such as halogen (Cl, Br, I, F), $NR^*_2$, $OR^*$, $SeR^*$, $TeR^*$, $PR^*_2$, $AsR^*_2$, $SbR^*_2$, $SR^*$, $BR^*_2$, $SiR^*_3$, $GeR^*_3$, $SnR^*_3$, $PbR^*_3$, and the like or where at least one heteroatom has been inserted within the hydrocarbyl radical, such as halogen (Cl, Br, I, F), O, S, Se, Te, $NR^*$, $PR^*$, $AsR^*$, $SbR^*$, $BR^*$, $SiR^*_2$, $GeR^*_2$, $SnR^*_2$, $PbR^*_2$, and the like, where $R^*$ is, independently, hydrogen or a hydrocarbyl.

In some embodiments, the hydrocarbyl radical is independently selected from methyl, ethyl, ethenyl and isomers of propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, heneicosyl, docosyl, tricosyl, tetracosyl, pentacosyl, hexacosyl, heptacosyl, octacosyl, nonacosyl, triacontyl, propenyl, butenyl, pentenyl, hexenyl, heptenyl, octenyl, nonenyl, decenyl, undecenyl, dodecenyl, tridecenyl, tetradecenyl, pentadecenyl, hexadecenyl, heptadecenyl, octadecenyl, nonadecenyl, eicosenyl, heneicosenyl, docosenyl, tricosenyl, tetracosenyl, pentacosenyl, hexacosenyl, heptacosenyl, octacosenyl, nonacosenyl, triacontenyl, propynyl, butynyl, pentynyl, hexynyl, heptynyl, octynyl, nonynyl, decynyl, undecynyl, dodecynyl, tridecynyl, tetradecynyl, pentadecynyl, hexadecynyl, heptadecynyl, octadecynyl, nonadecynyl, eicosynyl, heneicosynyl, docosynyl, tricosynyl, tetracosynyl, pentacosynyl, hexacosynyl, heptacosynyl, octacosynyl, nonacosynyl, and triacontynyl. Also included are isomers of saturated, partially unsaturated and aromatic cyclic structures wherein the radical may additionally be subjected to the types of substitutions described above. Examples include phenyl, methylphenyl, benzyl, methylbenzyl, naphthyl, cyclohexyl, cyclohexenyl, methylcyclohexyl, and the like. For this invention, when a radical is listed, it indicates that radical type and all other radicals formed when that radical type is subjected to the substitutions defined above. Alkyl, alkenyl, and alkynyl radicals listed include all isomers including where appropriate cyclic isomers, for example, butyl includes n-butyl, 2-methylpropyl, 1-methylpropyl, tert-butyl, and cyclobutyl (and analogous substituted cyclopropyls); pentyl includes n-pentyl, cyclopentyl, 1-methylbutyl, 2-methylbutyl, 3-methylbutyl, 1-ethylpropyl, and neopentyl (and analogous substituted cyclobutyls and cyclopropyls); butenyl includes E and Z forms of 1-butenyl, 2-butenyl, 3-butenyl, 1-methyl-1-propenyl, 1-methyl-2-propenyl, 2-methyl-1-propenyl, and 2-methyl-2-propenyl (and cyclobutenyls and cyclopropenyls). Cyclic compound having substitutions include all isomer forms, for example, methylphenyl would include ortho-methylphenyl, meta-methylphenyl and para-methylphenyl; dimethylphenyl would include 2,3-dimethylphenyl, 2,4-dimethylphenyl, 2,5-dimethylphenyl, 2,6-diphenylmethyl, 3,4-dimethylphenyl, and 3,5-dimethylphenyl.

Silylcarbyl radicals (also referred to as silylcarbyls, silylcarbyl groups or silylcarbyl substituents) are radicals in which one or more hydrocarbyl hydrogen atoms have been substituted with at least one $SiR^*3$ containing group or where at least one $—Si(R^*)_2—$ has been inserted within the hydrocarbyl radical where $R^*$ is independently a hydrocarbyl or halocarbyl radical, and two or more $R^*$ may join together to form a substituted or unsubstituted saturated, partially unsaturated or aromatic cyclic or polycyclic ring structure. Silylcarbyl radicals can be bonded via a silicon atom or a carbon atom.

Substituted silylcarbyl radicals are silylcarbyl radicals in which at least one hydrogen atom has been substituted with at least one functional group such as $NR^*_2$, $OR^*$, $SeR^*$, $TeR^*$, $PR^*_2$, $AsR^*_2$, $SbR^*_2$, $SR^*$, $BR^*_2$, $GeR^*_3$, $SnR^*_3$, $PbR_3$ and the like or where at least one non-hydrocarbon atom or group has been inserted within the silylcarbyl radical, such as $—O—$, $—S—$, $—Se—$, $—Te—$, $—N(R^*)—$, $=N—$, $—P(R^*)—$, $=P—$, $—As(R^*)—$, $=As—$, $—Sb(R^*)—$, $=Sb—$, $—B(R^*)—$, $=B—$, $—Ge(R^*)_2—$, $—Sn(R^*)_2—$, $—Pb(R^*)_2—$ and the like, where $R^*$ is independently a hydrocarbyl or halocarbyl radical, and two or more $R^*$ may join together to form a substituted or unsubstituted saturated, partially unsaturated or aromatic cyclic or polycyclic ring structure.

Halocarbyl radicals are radicals in which one or more hydrocarbyl hydrogen atoms have been substituted with at least one halogen (e.g., F, Cl, Br, I) or halogen-containing group (e.g., $CF_3$).

Substituted halocarbyl radicals are radicals in which at least one halocarbyl hydrogen or halogen atom has been substituted with at least one functional group such as $NR^*_2$, $OR^*$, $SeR^*$, $TeR^*$, $PR^*_2$, $AsR^*_2$, $SbR^*_2$, $SR^*$, $BR^*_2$, $SiR^*_3$, $GeR^*_3$, $SnR^*_3$, $PbR^*_3$, and the like or where at least one non-carbon atom or group has been inserted within the halocarbyl radical such as $—O—$, $—S—$, $—Se—$, $—Te—$, $—N(R^*)—$, $=N—$, $—P(R^*)—$, $=P—$, $—As(R^*)—$, $=As—$, $—Sb(R^*)—$, $=Sb—$, $—B(R^*)—$, $=B—$, $—Si(R^*)_2—$, $—Ge(R^*)_2—$, $—Sn(R^*)_2—$, $—Pb(R^*)_2—$ and the like, where $R^*$ is independently a hydrocarbyl or halocarbyl radical provided that at least one halogen atom remains on the original halocarbyl radical. Additionally, two or more $R^*$ may join together to form a substituted or unsubstituted saturated, partially unsaturated or aromatic cyclic or polycyclic ring structure.

The term "Cn" group or compound refers to a group or a compound comprising carbon atoms at total number thereof of n. Thus, a "Cm-Cn" group or compound refers to a group or compound comprising carbon atoms at a total number thereof in the range from m to n. Thus, a $C_1$-$C_{50}$ alkyl group refers to an alkyl group comprising carbon atoms at a total number thereof in the range from 1 to 50.

The term "olefin," alternatively termed "alkene," refers to an unsaturated hydrocarbon compound having a hydrocarbon chain containing at least one carbon-to-carbon double bond in the structure thereof, wherein the carbon-to-carbon double bond does not constitute a part of an aromatic ring. The olefin may be linear, branched linear, or cyclic. For purposes of this specification and the claims appended thereto, when a polymer or copolymer is referred to as comprising an olefin, including, but not limited to ethylene, propylene, and butene, the olefin present in such polymer or copolymer is the polymerized form of the olefin. For example, when a copolymer is said to have an "ethylene" content of 35 wt % to 55 wt %, it is understood that the mer unit in the copolymer is derived from ethylene in the polymerization reaction and said derived units are present at 35 wt % to 55 wt %, based upon the weight of the copolymer. A "polymer" has two or more of the same or different mer units. A "homopolymer" is a polymer having mer units that are the same. A "copolymer" is a polymer having two or more mer units that are different from each other. A "terpolymer" is a polymer having three mer units that are different from each other. "Different" as used to refer to mer units indicates that the mer units differ from each other by at least one atom or are different isomerically. Thus, an "olefin" is intended to embrace all structural isomeric forms of olefins, unless it is specified to mean a single isomer or the context clearly indicates otherwise. An oligomer is a polymer having a low molecular weight, such as an Mn of 21,000 g/mol or less (preferably 10,000 g/mol or less), and/or a low number of mer units, such as 100 mer units or less (preferably 75 mer units or less).

The term "alpha-olefin" refers to an olefin having a terminal carbon-to-carbon double bond in the structure thereof ($(R^1R^2)$—C=CH$_2$, where $R^1$ and $R^2$ can be independently hydrogen or any hydrocarbyl group; preferably $R^1$ is hydrogen and $R^2$ is an alkyl group). A "linear alpha-olefin" is an alpha-olefin defined in this paragraph wherein $R^1$ is hydrogen, and $R^2$ is hydrogen or a linear alkyl group. Non-limiting examples of α-olefins include ethylene, 1-butene, 1-pentene, 1-hexene, 1-heptene, 1-octene, 1-nonene, 1-decene, 1-undecene 1-dodecene, 1-tridecene, 1-tetradecene, 1-pentadecene, 1-hexadecene, 1-heptadecene, 1-octadecene, 1-nonadecene, 1-eicosene, 1-heneicosene, 1-docosene, 1-tricosene, 1-tetracosene, 1-pentacosene, 1-hexacosene, 1-heptacosene, 1-octacosene, 1-nonacosene, 1-triacontene, 4-methyl-1-pentene, 3-methyl-1-pentene, 5-methyl-1-nonene, 3,5,5-trimethyl-1-hexene, vinylcyclohexane, and vinylnorbornane. Non-limiting examples of cyclic olefins and diolefins include cyclobutene, cyclopentene, cyclohexene, cycloheptene, cyclooctene, cyclononene, cyclodecene, norbornene, 4-methylnorbornene, 2-methylcyclopentene, 4-methylcyclopentene, vinylcyclohexane, norbornadiene, dicyclopentadiene, 5-ethylidene-2-norbornene, vinylcyclohexene, 5-vinyl-2-norbornene, 1,3-divinylcyclopentane, 1,2-divinylcyclohexane, 1,3-divinylcyclohexane, 1,4-divinylcyclohexane, 1,5-divinylcyclooctane, 1-allyl-4-vinylcyclohexane, 1,4-diallylcyclohexane, 1-allyl-5-vinylcyclooctane, and 1,5-diallylcyclooctane.

The term "vinyl" means an olefin having the following formula:

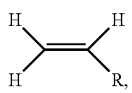

wherein R is a hydrocarbyl group, preferably a saturated hydrocarbyl group such as an alkyl group.

The term "vinylidene" means an olefin having the following formula:

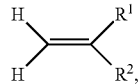

wherein $R^1$ and $R^2$ are each independently a hydrocarbyl group, preferably a saturated hydrocarbyl group such as alkyl group. Vinylidenes are 1,1-di-substituted vinylene groups.

The term "di-substituted vinylene" means:
(i) an olefin having the following formula:

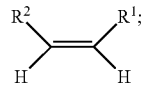

(ii) an olefin having the following formula:

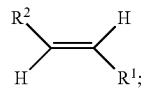

(iii) a mixture of (i) and (ii) at any proportion thereof, wherein $R^1$ and $R^2$, the same or different at each occurrence, are each independently a hydrocarbyl group, preferably saturated hydrocarbyl group such as alkyl group. Di-substituted vinylenes represent only 1,2-di-substituted vinylene groups and do not include vinylidenes, or 1,1-di-substituted vinylenes. The term "vinylene," as used herein, is an alternative term for "di-substituted vinylene" only and not as a generic class of multiple vinylene species.

The term "tri-substituted vinylene" means an olefin having the following formula:

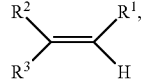

wherein $R^1$, $R^2$ and $R^3$ are each independently a hydrocarbyl group, preferably a saturated hydrocarbyl group such as alkyl group, or alternatively $R^1$ and $R^2$ can together form a non-aryl ring structure with $R^3$ being a pendant hydrocarbyl group.

As used herein, "poly alpha-olefin(s)" (PAO(s)) are polymers of one or more alpha-olefin monomers, particularly an oligomer of one or more alpha-olefins. PAOs are polymeric, typically oligomeric, molecules produced from the polymerization reactions of alpha-olefin monomer molecules in the presence of a catalyst system, optionally further hydrogenated to remove residual carbon-carbon double bonds therein or optionally further functionalized by reaction with some or all of the residual carbon-carbon bonds therein. Thus, the PAO can be a dimer, a trimer, a tetramer, or any other oligomer or polymer comprising two or more structure units derived from one or more alpha-olefin monomer(s). The PAO molecule can be highly regio-regular, such that the bulk material may exhibit an isotacticity, or a syndiotacticity when measured by $^{13}$C NMR. The PAO molecule can be highly regio-irregular, such that the bulk material can be substantially atactic when measured by $^{13}$C NMR. A PAO material made by using a metallocene-based catalyst system is typically called a metallocene-PAO (mPAO), and a PAO material made by using traditional non-metallocene-based catalysts (e.g., Lewis acids, supported chromium oxide, and the like) is typically called a conventional PAO (cPAO).

The term "carbon backbone" refers to the longest straight carbon chain in the molecule of the compound or the group in question. "Branches" or "pendant groups" interchangeably refer to any non-hydrogen group connected to the carbon backbone other than those attached to the carbon atoms at the very ends of the carbon backbone. As used herein, the term "length" of a pendant group is defined as the total number of carbon atoms in the longest carbon chain in the pendant group, counting from the first carbon atom attached to the carbon backbone and ending with the final carbon atom therein, without taking into consideration any substituents or pendant groups on the chain. In some embodiments, the pendant group is free of substituents comprising more than 2 carbon atoms (or more than 1 carbon atom), or is free of any substituent. A pendant group may contain a cyclic group or a portion thereof in the longest carbon chain, in which case half of the carbon atoms in the cyclic group are counted toward the length of the pendant group. Thus, by way of examples, a linear $C_8$ pendant group has a length of 8; each of the pendant groups PG-1 (cyclohexylmethylene) and PG-2 (phenylmethylene) has a length of 4; and each of the pendant groups PG-3 (o-heptylphenylmethylene) and PG-4 (p-heptylphenylmethylene) has a length of 11. Where a PAO molecule contains multiple pendant groups, the arithmetic average of the lengths of all such pendant groups is calculated as the average length of all pendant groups in the PAO molecule.

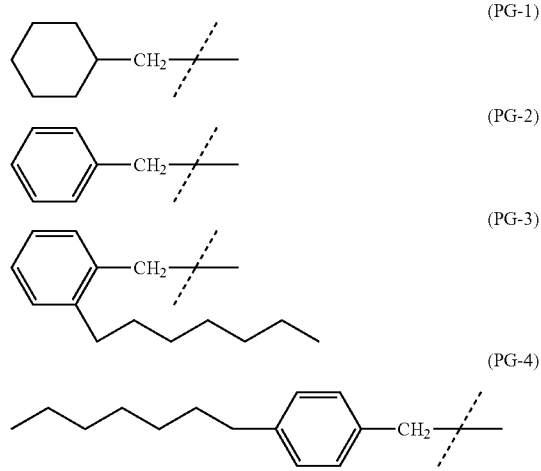

In the present invention, any metallocene compound may have one or more optical isomers. All metallocene compound identified herein by name or structure shall include all possible optical isomers thereof and mixtures of any such optical isomers. For example, metallocene compound Me$_2$Si (Me$_4$Cp)(3-PrInd)ZrMe$_2$ shall include the following two optical isomers and mixtures thereof, even if only one structure is given when it is described:

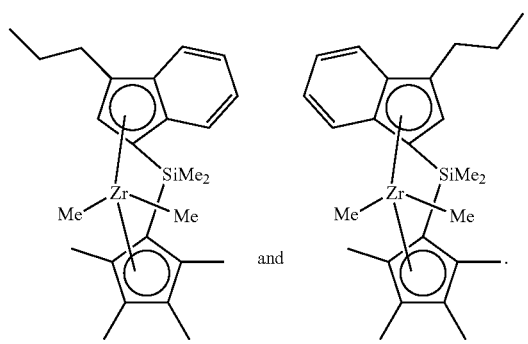

Unless specified otherwise, the term "substantially all" with respect to PAO molecules means at least 90 mol % (such as at least 95 mol %, at least 98 mol %, at least 99 mol %, or even 100 mol %).

Unless specified otherwise, the term "substantially free of" with respect to a particular component means the concentration of that component in the relevant composition is no greater than 10 mol % (such as no greater than 5 mol %, no greater than 3 mol %, no greater than 1 mol %, or about 0%, within the bounds of the relevant measurement framework), based on the total quantity of the relevant composition.

The terms "catalyst" and "catalyst compound" are defined to mean a compound capable of initiating catalysis and/or of facilitating a chemical reaction with little or no poisoning/consumption. In the description herein, the catalyst may be described as a catalyst precursor, a pre-catalyst compound, or a transition metal compound, and these terms are used interchangeably. A catalyst compound may be used by itself to initiate catalysis or may be used in combination with an activator to initiate catalysis. When the catalyst compound is combined with an activator to initiate catalysis, the catalyst compound is often referred to as a pre-catalyst or catalyst precursor. A "catalyst system" is combination of at least one catalyst compound, at least one activator, an optional co-activator, and an optional support material, where the system can polymerize monomers to form polymer.

A scavenger is a compound typically added to facilitate oligomerization/polymerization by scavenging impurities. Some scavengers may also act as activators and may be referred to as co-activators. A co-activator, that is not a scavenger, may be used in conjunction with an activator in order to form an active catalyst. In some embodiments, a co-activator can be pre-mixed with the catalyst compound to form an alkylated catalyst compound.

As used herein, a "lubricant" refers to a substance that can be introduced between two or more moving surfaces and lower the level of friction between two adjacent surfaces moving relative to each other. A lubricant "base stock" is a material, typically a fluid at the operating temperature of the lubricant, used to formulate a lubricant by admixing it with other components. Non-limiting examples of base stocks suitable in lubricants include API Group I, Group II, Group III, Group IV, Group V and Group VI base stocks. Fluids derived from Fischer-Tropsch process or Gas-to-Liquid ("GTL") processes are examples of synthetic base stocks useful for making modern lubricants. GTL base stocks and processes for making them can be found, e.g., in PCT Publication No. WO 2005/121280 and in U.S. Pat. Nos. 7,344,631; 6,846,778; 7,241,375; and 7,053,254.

All kinematic viscosity values in the present invention are as determined according to ASTM D445. Kinematic viscosity at 100° C. is reported herein as KV100, and kinematic viscosity at 40° C. is reported herein as KV40. Unit of all KV100 and KV40 values herein is cSt, unless otherwise specified.

All viscosity index (VI) values in the present invention are as determined according to ASTM D2270.

All Noack volatility (NV) values in the present invention are as determined according to ASTM D5800 unless specified otherwise. Units of all NV values are wt %, unless otherwise specified.

Unless otherwise indicated, bromine number values in the present invention are determined according to ASTM D 1159.

All numerical values within the detailed description and the claims herein are modified by "about" or "approximately" the indicated value, and consider experimental error and variations that would be expected by a person having ordinary skill in the art.

In the present invention, all percentages of pendant groups, terminal carbon chains, and side chain groups are by mole, unless specified otherwise. Percent by mole is expressed as "mol %," and percent by weight is expressed as "wt %."

In the present invention, all molecular weight data are in the unit of g mol$^{-1}$.

NMR spectroscopy provides key structural information about the synthesized polymers. Proton NMR ($^1$H-NMR) analysis is used to determine the molecular weight of oligomer or polymer materials (including functionalized, hydrogenated, and uPAO materials). However, molecular weights of oligomer or polymer materials measured by $^1$H-NMR herein represent a number average molecular weight (Mn). In addition, $^1$H-NMR analysis of the unsaturated PAO product can give a quantitative breakdown of the olefinic structure types (viz. vinyl, di-substituted vinylene, tri-substituted vinylene, and vinylidene). In the present invention, compositions of mixtures of olefins comprising terminal olefins (vinyls and vinylidenes) and internal olefins (di-substituted vinylenes and tri-substituted vinylenes) are determined by using $^1$H-NMR as described in the experimental section. Carbon-13 NMR ($^{13}$C-NMR) can be used to determine tacticity of the PAOs of the present invention. Carbon-13 NMR can be used to determine the percentages of the triads, denoted (m,m)-triads (i.e., meso, meso), (m,r)—(i.e., meso, racemic) and (r,r)—(i.e., racemic, racemic) triads, respectively. The concentrations of these triads can define whether the polymer is isotactic, atactic or syndiotactic. In the present invention, the percentage of the (m,m)-triads in mol % is recorded as the isotacticity of the PAO material. Spectra for a PAO sample are acquired in the following manner. Approximately 100-1000 mg of the PAO sample is dissolved in ~2-3 ml of chloroform-d for $^{13}$C-NMR analysis. The samples are run with a ~60 s delay and ~90° pulse with at least 512 transients. The tacticity can be calculated using the peak around 35 ppm (CH$_2$ peak next to the branch point). Analysis of the spectra can be performed according to the paper by Kim, I.; Zhou, J.-M.; and Chung, H. Journal of Polymer Science: Part A: Polymer Chemistry 2000, 38 1687-1697. The calculation of tacticity is mm*100/(mm+mr+rr) for the molar percentages of (m,m)-triads, mr*100/(mm+mr+rr) for the molar percentages of (m,r)-triads, and rr*100/(mm+mr+rr) for the molar percentages of (r,r)-triads. The (m,m)-triads correspond to ~35.5-~34.55 ppm, the (m,r)-triads to ~34.55-~34.1 ppm, and the (r,r)-triads to ~34.1-~33.2 ppm.

The following abbreviations may be used through this specification: Cp is cyclopentadiene or cyclopentadienyl; Me is methyl, Ph is phenyl, Et is ethyl, Pr is propyl, iPr is isopropyl, n-Pr is normal propyl, Bu is butyl, iBu is isobutyl, tBu is tertiary butyl, p-tBu is para-tertiary butyl, nBu is normal butyl, TMS is trimethylsilyl, TIBAL is triisobutyl-aluminum, TNOAL or TNOA is triisobutyl n-octylalumi-num, MAO is methylalumoxane, pMe is para-methyl, Ar* is 2,6-diisopropylaryl, Bz or Bn are interchangeably benzyl, THF is tetrahydrofuran, RT is room temperature (i.e., approximately 23° C.), and tol is toluene.

In embodiments according to the present invention, a process for making a poly alpha-olefin, PAO comprises contacting a feed containing a $C_6$-$C_{32}$ alpha-olefin and optional ethylene with a catalyst system comprising a metallocene compound in a polymerization reactor under polymerization conditions to effect a polymerization reaction to obtain a polymerization reaction mixture comprising vinylidenes, tri-substituted vinylenes, and optionally di-substituted vinylenes, and optionally vinyls; and obtaining an unsaturated PAO product from the polymerization reaction mixture, wherein the polymerization reaction exhibits a selectivity toward greater than or equal to about 80 mol % vinylidenes, preferably 90 mol % vinylidenes, more preferably 96.5 mol % vinylidenes, based on total moles of vinyls, vinylidenes, di-substituted vinylenes, and tri-substituted vinylenes in the unsaturated PAO product; wherein the metallocene compound is represented by formula (I):

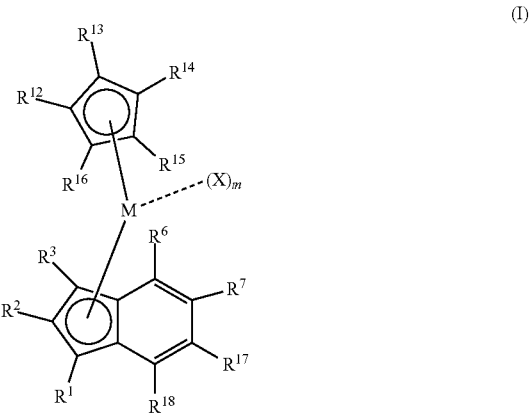

wherein: each $R^1$, $R^2$, and $R^3$ is, independently, hydrogen or a substituted or unsubstituted linear, branched linear, or cyclic $C_1$-$C_{20}$ hydrocarbyl group, preferably wherein a first one of $R^1$, $R^2$, and $R^3$ is a substituted or unsubstituted linear, branched linear, or cyclic $C_1$-$C_{20}$ hydrocarbyl group; a second one of $R^1$, $R^2$, and $R^3$ is hydrogen; and a third one of $R^1$, $R^2$, and $R^3$ is hydrogen, a substituted or unsubstituted linear, branched linear, or cyclic $C_1$-$C_{20}$ hydrocarbyl group; $R^6$, $R^7$, $R^{17}$, and $R^{18}$ are each independently hydrogen; a substituted or unsubstituted linear, branched linear, or cyclic $C_1$-$C_{30}$ hydrocarbyl group; or $R^6$ and $R^7$, $R^7$ and $R^{17}$, or $R^{17}$ and $R^{18}$, taken together with the carbon atoms in the indenyl ring to which they are directly connected, collectively form one or more substituted or unsubstituted rings annelated to the indenyl ring; $R^{12}$, $R^{13}$, $R^{14}$ and $R^{15}$ are each independently a substituted or unsubstituted linear, branched linear, or cyclic $C_1$-$C_{20}$ hydrocarbyl group; $R^{16}$ is a substituted or unsubstituted linear, branched linear, or cyclic $C_1$-$C_{20}$ hydrocarbyl group or silylcarbyl group; each X is independently a halogen, a hydride, an amide, an alkoxide, a sulfide, a phosphide, a diene, an amine, a phosphine, an ether, a $C_1$-$C_{20}$ substituted or unsubstituted linear, branched linear, or cyclic hydrocarbyl group, or two or more X moieties together form a fused ring or ring system; M is a group 3, 4 or 5 transition metal having an integer coordination number of v, typically 3, 4, or 5; and m is an integer equal to v-2, typically 1, 2, or 3.

In particular embodiments of the process, $R^2$ is hydrogen. In embodiments, one of $R^1$ and $R^3$ is a substituted or unsubstituted linear, branched linear, or cyclic $C_1$-$C_6$ hydrocarbyl group, and the other one of $R^1$ and $R^3$ is a hydrogen.

In some embodiments, one or both of $R^1$ and $R^3$ is a substituted or unsubstituted linear, branched linear, or cyclic $C_1$-$C_6$ hydrocarbyl group.

In some embodiments one of $R^1$ and $R^3$ comprise an alpha Group 14 atom directly attached to the indenyl ring, a beta Group 14 atom attached to the alpha atom, and two or more, preferably three, substituted or unsubstituted linear, branched linear, or cyclic $C_1$-$C_8$ hydrocarbyl groups attached to the beta atom.

In particular embodiments, the metallocene compound is represented by formula (II):

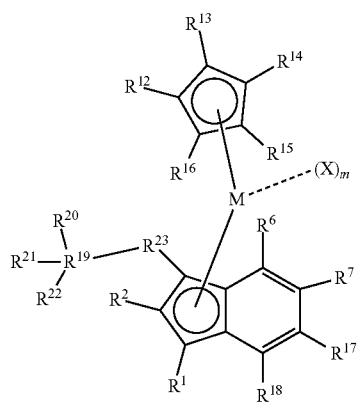

(II)

wherein: $R^1$ and $R^2$ are hydrogen; $R^{23}$ and $R^{19}$ comprise Group 14 atoms, preferably C, Ge, or Si (preferably $R^{23}$ is C and $R^{19}$ is C or Si); $R^{20}$, $R^{21}$, and $R^{22}$ are independently hydrogen or a substituted or unsubstituted linear, branched linear, or cyclic $C_1$-$C_{20}$ hydrocarbyl group and at least two of $R^{20}$, $R^{21}$, and $R^{22}$ are independently a substituted or unsubstituted linear, branched linear, or cyclic $C_1$-$C_{20}$ hydrocarbyl group, wherein at least two of $R^{20}$, $R^{21}$, and $R^{22}$ are a substituted or unsubstituted linear, branched linear, or cyclic $C_1$-$C_{20}$ hydrocarbyl group; $R^6$, $R^7$, $R^{17}$, and $R^{18}$ are each independently hydrogen; a substituted or unsubstituted linear, branched linear, or cyclic $C_1$-$C_{30}$ hydrocarbyl group; or $R^6$ and $R^7$, $R^7$ and $R^{17}$, or $R^{17}$ and $R^{18}$, taken together with the carbon atoms in the indenyl ring to which they are directly connected, collectively form one or more substituted or unsubstituted rings annelated to the indenyl ring; $R^{12}$, $R^{13}$, $R^{14}$, $R^{15}$, and $R^{16}$ are each independently a substituted or unsubstituted linear, branched linear, or cyclic $C_1$-$C_8$ hydrocarbyl group; each X is independently a halogen, a hydride, an amide, an alkoxide, a sulfide, a phosphide, a diene, an amine, a phosphine, an ether, or a $C_1$-$C_{20}$ substituted or unsubstituted linear, branched linear, or cyclic hydrocarbyl group, or two or more X moieties together form a fused ring or ring system; M is a group 3, 4, or 5 transition metal having an integer coordination number of v, such as 3, 4 or 5; and m is an integer equal to v-2, such as 1, 2 or 3.

In particular embodiments, $R^6$ and $R^7$, $R^7$ and $R^{17}$, or $R^{17}$ and $R^{18}$, taken together with the respective carbon atoms in the indenyl ring to which they are directly connected, form a ring annelated to the indenyl ring. In some embodiments, the ring annelated to the indenyl ring comprises one or more saturated carbon atoms. In some embodiments, at least four of $R^{12}$, $R^{13}$, $R^{14}$, $R^{15}$, and $R^{16}$ are each independently a substituted or unsubstituted linear, branched linear, or cyclic $C_1$-$C_8$ hydrocarbyl group, preferably methyl or ethyl.

In particular embodiments, $R^{16}$ is a substituted or unsubstituted linear, branched linear, or cyclic $C_1$-$C_8$ hydrocarbyl group, preferably methyl or ethyl. In some embodiments, i) at least three of $R^{12}$, $R^{13}$, $R^{14}$, $R^{15}$, and $R^{16}$ if present are not hydrogen; ii) two or more of $R^{12}$, $R^{13}$, $R^{14}$, $R^{15}$ and $R^{16}$ if present together form a fused ring or ring system; iii) at least two of $R^6$, $R^7$, $R^{17}$, and $R^{18}$ are hydrogen; iv) each X is independently a halogen or a substituted or unsubstituted linear, branched linear, or cyclic $C_1$-$C_6$ hydrocarbyl group; v) M comprises Zr or Hf; or a combination thereof.

In particular embodiments, $R^{12}$, $R^{13}$, $R^{14}$, $R^{15}$, and $R^{16}$ are each independently a substituted or unsubstituted linear, branched linear, or cyclic $C_1$-$C_8$ hydrocarbyl group, preferably methyl or ethyl.

In particular embodiments the metallocene compound is represented by formula (I-B), (III-B), (IV-B), (VI), (VIII), (IX), (X), (XI), (XII), (XV), (XVII), (XVIII), or (XIX):

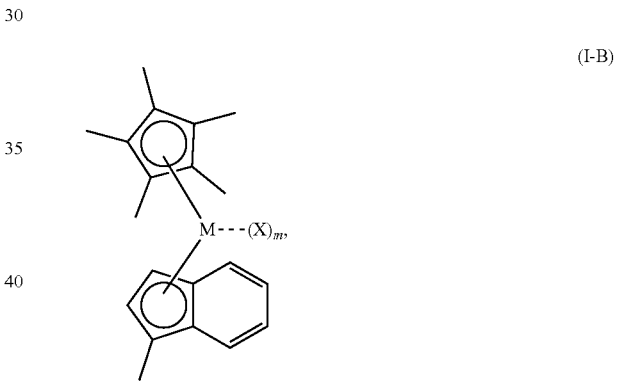

(I-B)

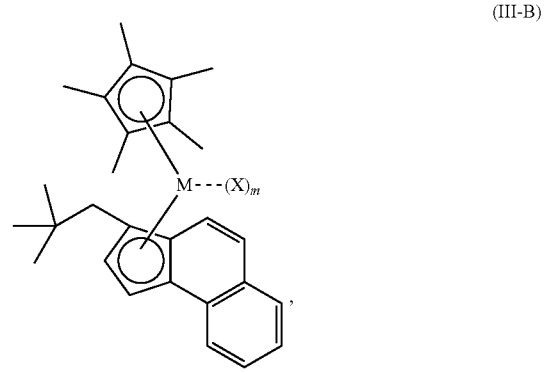

(III-B)

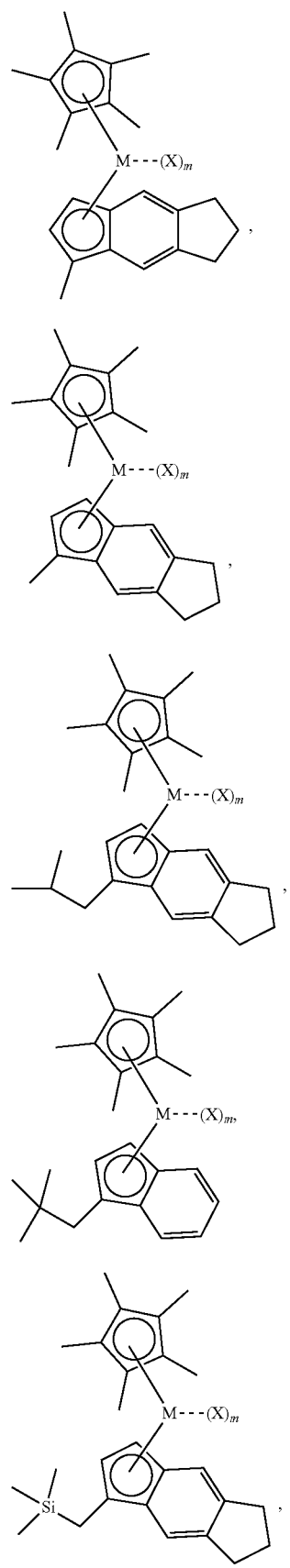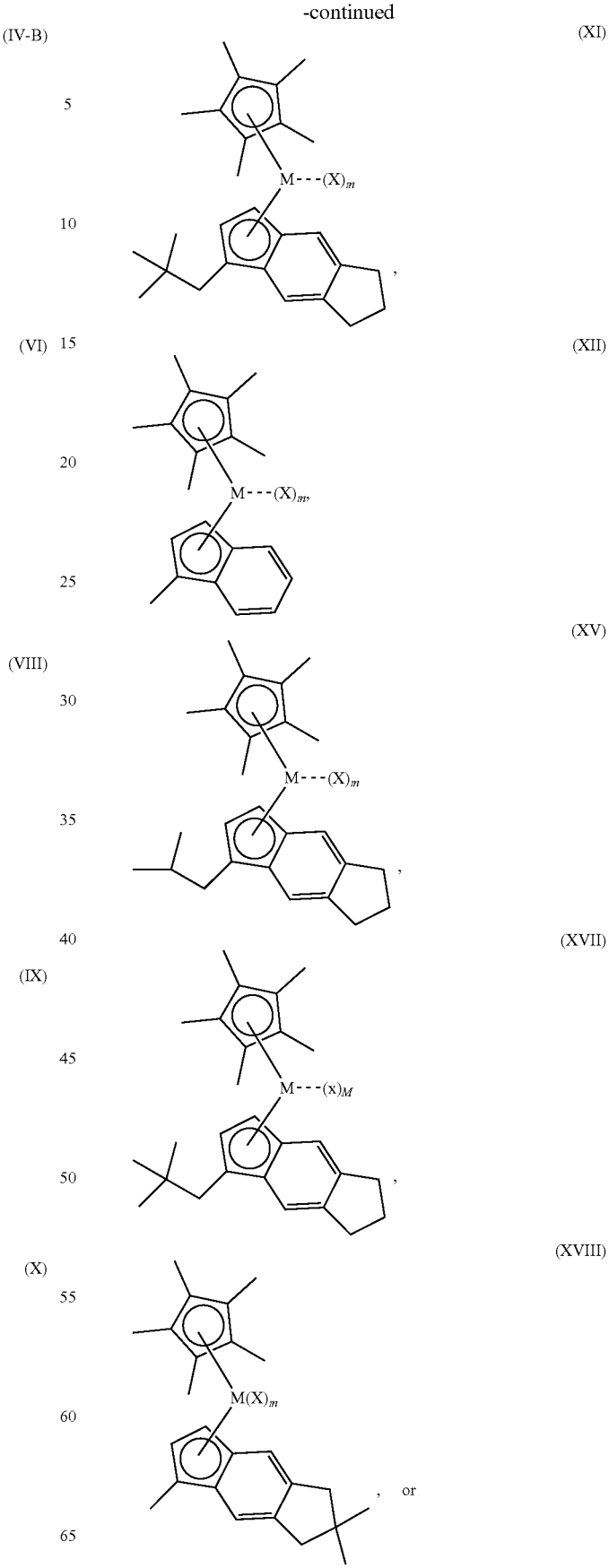

-continued (XIX)

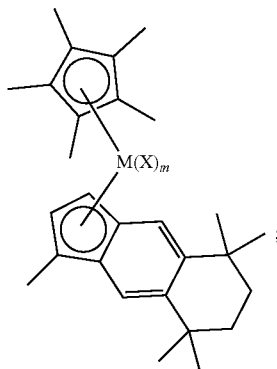

wherein each X is independently a halogen, a hydride, an amide, an alkoxide, a sulfide, a phosphide, a diene, an amine, a phosphine, an ether, or a $C_1$-$C_{20}$ substituted or unsubstituted linear, branched linear, or cyclic hydrocarbyl group, or two or more X moieties may together form a fused ring or ring system; M is Hf or Zr; and m is 2. In particular embodiments of the process, the metallocene is not represented by formula (I-B).

In some embodiments of the process, the polymerization reaction exhibits a selectivity toward a combination of greater than or equal to about 96.5 mol % vinylidenes, from 0.5 mol % to 3.5 mol % tri-substituted vinylenes, less than or equal to about 1.5 mol % di-substituted vinylenes, and less than or equal to about 1.5 mol % vinyls, based on total moles of vinyls, vinylidenes, di-substituted vinylenes, and tri-substituted vinylenes in the unsaturated PAO product.

In particular embodiments of the process, the polymerization reaction exhibits a selectivity toward a combination of vinylidenes of equal to or greater than 97.0 mol %, preferably equal to or greater than 97.9 mol %; tri-substituted vinylenes of less than 2.1 mol %; di-substituted vinylenes of 0.5 mol % or less; and vinyls of 1.0 mol % or less, based on total moles of vinyls, vinylidenes, di-substituted vinylenes, and tri-substituted vinylenes in the unsaturated PAO product. In particular embodiments of the process, the polymerization reaction exhibits a selectivity towards a combination of vinylidenes and tri-substituted vinylenes of collectively greater than 98.0 mol %, preferably greater than 98.5 mol %, and a combination of di-substituted vinylenes and vinyls of collectively less than 2.0 mol %, preferably less than 1.5 mol %, based on total moles of vinyls, vinylidenes, di-substituted vinylenes, and tri-substituted vinylenes in the unsaturated PAO product.

In some embodiments of the process the polymerization reaction results in the unsaturated PAO product having a number average molecular weight (Mn) of 1500 g/mol or less, preferably from 300 to 800 g/mol, as measured by $^1$H NMR. In some embodiments, the catalyst system further comprises a non-coordinating anion type activator, preferably wherein the non-coordinating anion type activator comprises: dimethylanilinium tetrakisperfluorophenylborate, dimethylanilinium tetrakisperfluoro-naphthylborate, triphenylcarbonium tetrakisperfluorophenylborate, triphenylcarbonium tetrakisperfluoronaphthylborate, dimethylanilinium tetrakisperfluorophenylaluminate, dimethylanilinium tetrakisperfluoronaphthylaluminate, or combinations thereof.

In particular embodiments of the process, the polymerization conditions comprise a reaction temperature from 40° C. to 150° C.; an average activity level of at least 1200 g/s·mol; the polymerization reaction mixture exhibits an oligomer yield of at least 10%; or a combination thereof.

In some embodiments the process further comprises: a) contacting the unsaturated PAO product with hydrogen to convert at least a portion of the unsaturated PAO product to a hydrogenated PAO product; b) contacting the unsaturated PAO product with a chemical reagent to convert at least a portion of the unsaturated PAO product to a functionalized PAO product; or a combination thereof.

In particular embodiments of the process, the feed comprises $C_6$-$C_{24}$ alpha-olefin; and any combination of $C_2$-$C_5$ alpha-olefins are collectively present in the alpha-olefin feed at no higher than 25 mol %, based on the total moles of the alpha-olefins supplied to the polymerization reactor, preferably wherein the alpha-olefin feed is substantially free of ethylene, propylene, $C_4$ alpha-olefins, and $C_5$ alpha-olefins; or a combination thereof. Preferably, the alpha-olefin feed is substantially free (preferably absent, 0 mol %) of propylene, $C_4$ alpha-olefins, and $C_5$ alpha-olefins; or a combination thereof and optionally comprises less than 25 mol % ethylene, preferably less than 15 mol %, preferably less than 5 mol %.

In embodiments of the invention, an unsaturated poly alpha-olefin product comprises greater than or equal to about 80 mol % vinylidenes, preferably 90 mol % vinylidenes, more preferably 96.5 mol % vinylidenes, based on total moles of vinyls, vinylidenes, di-substituted vinylenes, and tri-substituted vinylenes contained therein. In particular embodiments the unsaturated poly alpha-olefin product comprises 96.5 mol % to 99.9 mol % of vinylidenes; 0.1 mol % to 3.5 mol % of tri-substituted vinylenes; 3.0 mol % or less of di-substituted vinylenes; 3.0 mol % or less of vinyl groups; based on total moles of vinylidenes, tri-substituted vinylenes, di-substituted vinylenes, and vinylidenes contained therein; and a number average molecular weight (Mn) of 1500 g/mol or less as measured by $^1$H NMR.

In some embodiments the unsaturated poly alpha-olefin product comprises less than or equal to about 1.0 mol % di-substituted vinylenes, when present; less than or equal to about 1.0 mol % vinyl groups when present; and a number average molecular weight (Mn) of 1000 g/mol or less as measured by $^1$H NMR.

In particular embodiments, the unsaturated poly alpha-olefin product comprises from 98 mol % to 99.5 mol % of a combination of vinylidenes and tri-substituted vinylenes; 0.5 mol % to 2 mol % of a combination of di-substituted vinylenes and vinyl groups, and a number average molecular weight (Mn) of 800 g/mol or less as measured by $^1$HNMR.

In embodiments of the invention, a catalyst compound suitable to produce an unsaturated PAO product from $C_6$-$C_{32}$ alpha-olefin under polymerization conditions comprises a polymerization selectivity suitable to form an unsaturated PAO product comprising greater than or equal to about 80 mol % vinylidenes, preferably 90 mol % vinylidenes, more preferably 96.5 mol % vinylidenes, based on total moles of vinyls, vinylidenes, di-substituted vinylenes, and tri-substituted vinylenes in the unsaturated PAO product. In particular embodiments, the catalyst compound is represented by the formula (F-MC2):

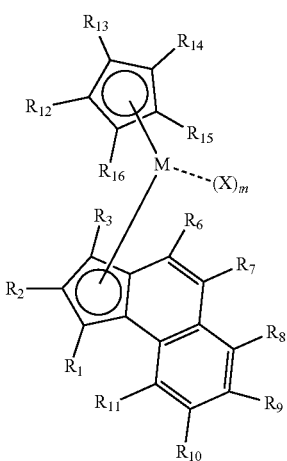

(F-MC2)

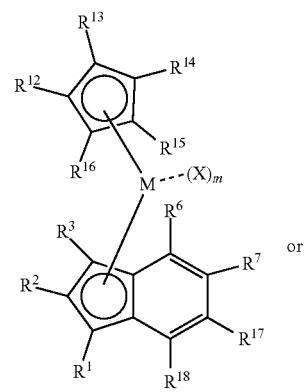

(I)

in which one of $R^1$, $R^2$, and $R^3$ is an alpha Group 14 atom directly attached to the indenyl ring, and a beta Group 14 atom attached to the alpha atom, and two or more, preferably three, substituted or unsubstituted linear, branched linear, or cyclic $C_1$-$C_8$ hydrocarbyl groups attached to the beta atom, optionally two of $R^1$, $R^2$, and $R^3$ are each hydrogen; $R^6$, $R^7$, $R^8$, $R^9$, $R^{10}$, and $R^{11}$ are each independently a hydrogen or a substituted or unsubstituted linear, branched linear, or cyclic $C_1$-$C_{20}$ hydrocarbyl group; $R^{12}$, $R^{13}$, $R^{14}$, and $R^{15}$ are each independently a hydrogen, or a substituted or unsubstituted linear, branched linear, or cyclic $C_1$-$C_{20}$ hydrocarbyl group; $R^{16}$ is a hydrogen, a substituted or unsubstituted linear, branched linear, or cyclic $C_1$-$C_{20}$ hydrocarbyl group or silylcarbyl group; each X is independently a halogen, a hydride, an amide, an alkoxide, a sulfide, a phosphide, a diene, an amine, a phosphine, an ether, or a $C_1$-$C_{20}$ substituted or unsubstituted linear, branched linear, or cyclic hydrocarbyl group, or two or more X moieties together form a fused ring or ring system; M is a group 3, 4, or 5 transition metal having an integer coordination number of v, such as 3, 4, or 5; and m is an integer equal to v-2, such as 1, 2 or 3.

In particular embodiments, the catalyst compound comprises a polymerization selectivity suitable to form an unsaturated PAO product comprising 96.5 mol % to 99.9 mol % of vinylidenes; 0.1 mol % to 3.5 mol % of tri-substituted vinylenes; 2.0 mol % or less of di-substituted vinylenes; 2.0 mol % or less of vinyl groups; based on total moles of vinyls, vinylidenes, di-substituted vinylenes, and tri-substituted vinylenes in the unsaturated PAO product; and a number average molecular weight (Mn) of 1500 g/mol or less as measured by $^1$H NMR.

In particular embodiments, the catalyst compound is represented by formula (I), (II), (F-MC2), or (IV):

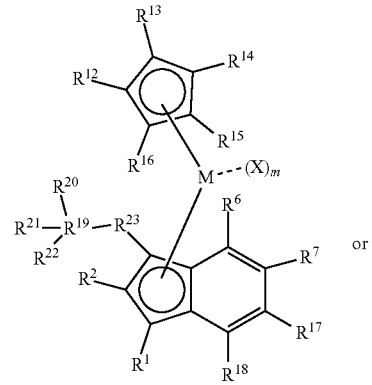

(II)

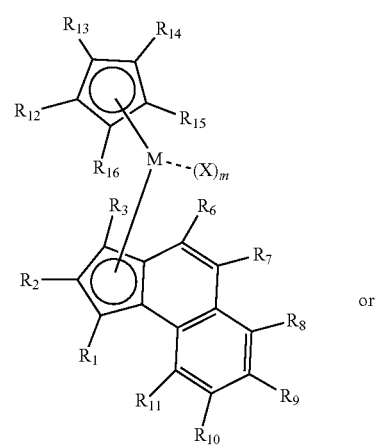

(F-MC2)

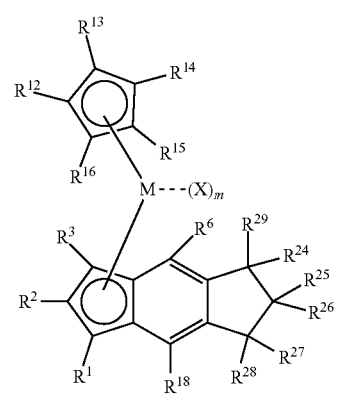

(IV)

wherein:

i) according to formula (I): a first one of $R^1$ and $R^3$ is a substituted or unsubstituted linear, branched linear, or cyclic $C_1$-$C_{20}$ hydrocarbyl group; a second one of $R^1$, $R^2$, and $R^3$ is a hydrogen; the third one of $R^1$, $R^2$, and $R^3$ is a hydrogen; $R^6$, $R^7$, $R^{17}$, and $R^{18}$ are each independently hydrogen, a substituted or unsubstituted linear, branched linear, or cyclic $C_1$-$C_{30}$ hydrocarbyl group; and R $R^{12}$, $R^{13}$, $R^{14}$, $R^{15}$, and $R^{16}$ are each independently a substituted or unsubstituted linear, branched linear, or cyclic $C_1$-$C_{20}$ hydrocarbyl group or $R^{16}$ may be a substituted or unsubstituted linear, branched linear, or cyclic $C_1$-$C_{20}$, preferably $C_1$-$C_8$, hydrocarbyl group or silylcarbyl group; or ii) according to formula (II): $R^1$ and $R^2$ are hydrogen; $R^{23}$ and $R^{19}$ comprise Group 14 atoms, such as C, Ge, and Si; $R^{20}$, $R^{21}$, and $R^{22}$ are independently hydrogen or a substituted or unsubstituted linear, branched linear, or cyclic $C_1$-$C_{20}$ hydrocarbyl group, wherein at least two of $R^{20}$, $R^{21}$, and $R^{22}$ are a substituted or unsubstituted linear, branched linear, or cyclic $C_1$-$C_{20}$ hydrocarbyl group; $R^6$, $R^7$, $R^{17}$, and $R^{18}$ are each independently hydrogen, a substituted or unsubstituted linear, branched linear, or cyclic $C_1$-$C_{30}$ hydrocarbyl group, or two of $R^6$, $R^7$, $R^{17}$, and $R^{18}$ taken together with the carbon atoms in the indenyl ring to which they are directly connected, collectively form one or more substituted or unsubstituted rings annelated to the indenyl ring; and $R^{12}$, $R^{13}$, $R^{14}$, $R^{15}$ and $R^{16}$ are each independently a substituted or unsubstituted linear, branched linear, or cyclic $C_1$-$C_{20}$ hydrocarbyl group; or iii) according to formula (F-MC2): one of $R^1$ and $R^3$ is a substituted or unsubstituted linear, branched linear, or cyclic $C_1$-$C_{20}$ hydrocarbyl group; two of $R^1$, $R^2$, and $R^3$ are each hydrogen; $R^6$, $R^7$, $R^8$, $R^9$, $R^{10}$, and $R^{11}$ are each independently hydrogen, a substituted or unsubstituted linear, branched linear, or cyclic $C_1$-$C_{30}$ hydrocarbyl group, or two of $R^6$, $R^7$, $R^8$, $R^9$, $R^{10}$, and $R^{11}$ taken together with the carbon atoms in the benzindenyl ring to which they are directly connected, collectively form one or more substituted or unsubstituted rings annelated to the benz-indenyl ring; and $R^{12}$, $R^{13}$, $R^{14}$, $R^{15}$, and $R^{16}$ are each independently a substituted or unsubstituted linear, branched linear, or cyclic $C_1$-$C_{20}$ hydrocarbyl group; or iv) according to formula (IV): one of $R^1$ and $R^3$ is a substituted or unsubstituted linear, branched linear, or cyclic $C_1$-$C_{20}$ hydrocarbyl group; two of $R^1$, $R^2$, and $R^3$ are each hydrogen; $R^6$, $R^{18}$, $R^{29}$, $R^{24}$, $R^{25}$, $R^{26}$, and $R^{27}$ are each independently hydrogen, a substituted or unsubstituted linear, branched linear, or cyclic $C_1$-$C_{30}$ hydrocarbyl group, or two of $R^6$, $R^{18}$, $R^{29}$, $R^{24}$, $R^{25}$, $R^{26}$, and $R^{27}$ taken together with the carbon atoms in the cyclopentan-indenyl ring to which they are directly connected, collectively form one or more substituted or unsubstituted rings annelated to the cyclopentan-indenyl ring; and $R^{12}$, $R^{13}$, $R^{14}$, $R^{15}$, and $R^{16}$ are each independently a substituted or unsubstituted linear, branched linear, or cyclic $C_1$-$C_{20}$ hydrocarbyl group; wherein in the formulae (I), (II), (III), (IV): each X is independently a halogen, a hydride, an amide, an alkoxide, a sulfide, a phosphide, a diene, an amine, a phosphine, an ether, a $C_1$-$C_{20}$ substituted or unsubstituted linear, branched linear, or cyclic hydrocarbyl group, or two or more X moieties together form a fused ring or ring system; M is a group 3, 4, or 5 transition metal having an integer coordination number of v, such as 3, 4, or 5; and m is an integer equal to v-2, such as 1, 2, or 3.

In particular embodiments, the catalyst compound comprises a polymerization selectivity suitable to form an unsaturated PAO product comprising: greater than or equal to about 96.5 mol % vinylidenes; less than or equal to about 3.5 mol % tri-substituted vinylenes; less than or equal to about 1.0 mol % di-substituted vinylenes, when present; less than or equal to about 1.0 mol % vinyl groups when present; based on total moles of vinyls, vinylidenes, di-substituted vinylenes, and tri-substituted vinylenes in the unsaturated PAO product; and a number average molecular weight (Mn) of 1500 g/mol or less as measured by $^1$H NMR.

In particular embodiments, the catalyst compound is represented by formula (III-B), (IV-B), (VI), (VIII), (IX), (X), (XI), (XII), (XV), (XVII) (XVIII) or (XIX):

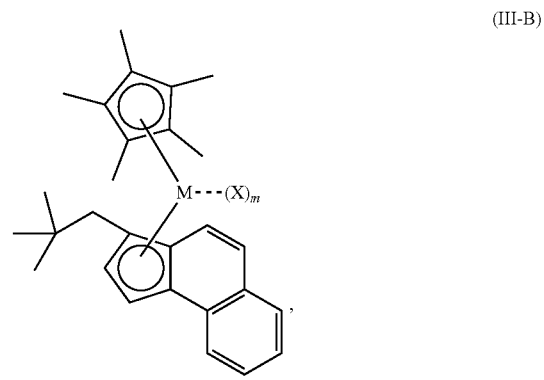

(III-B)

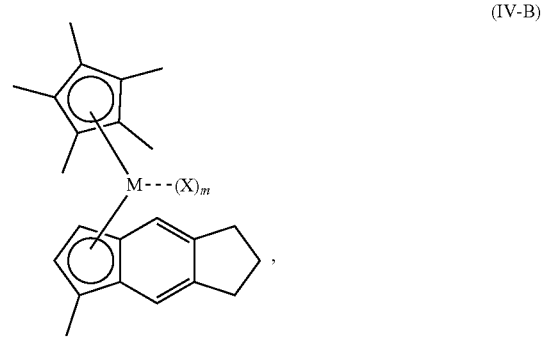

(IV-B)

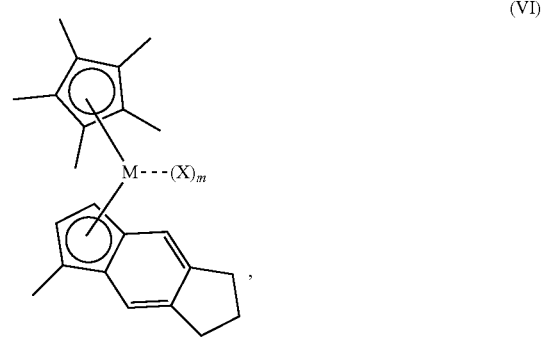

(VI)

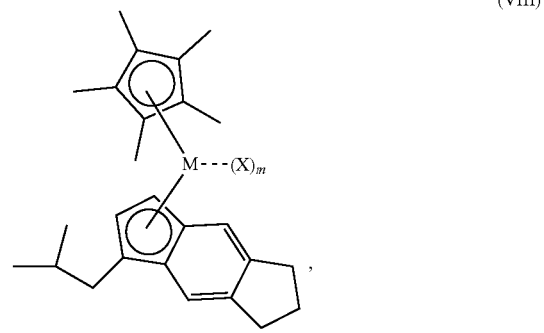

(VIII)

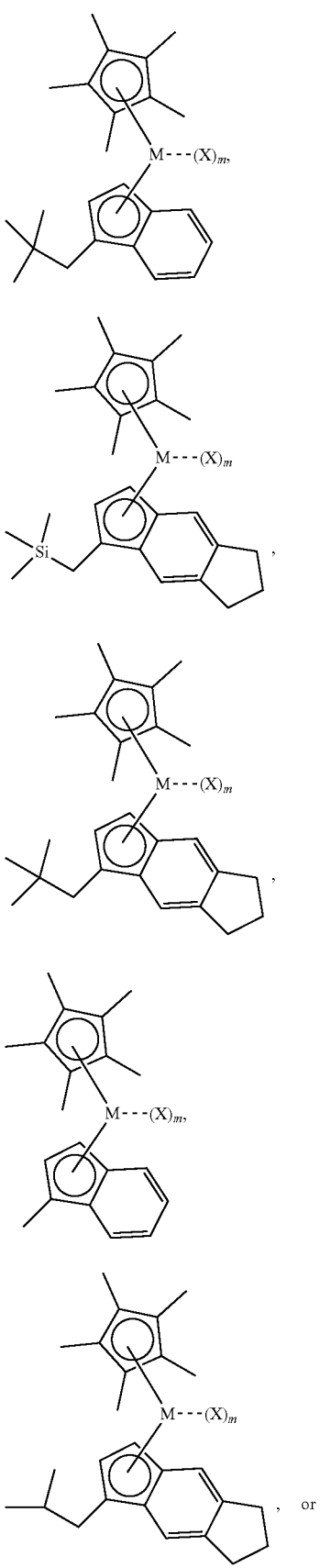

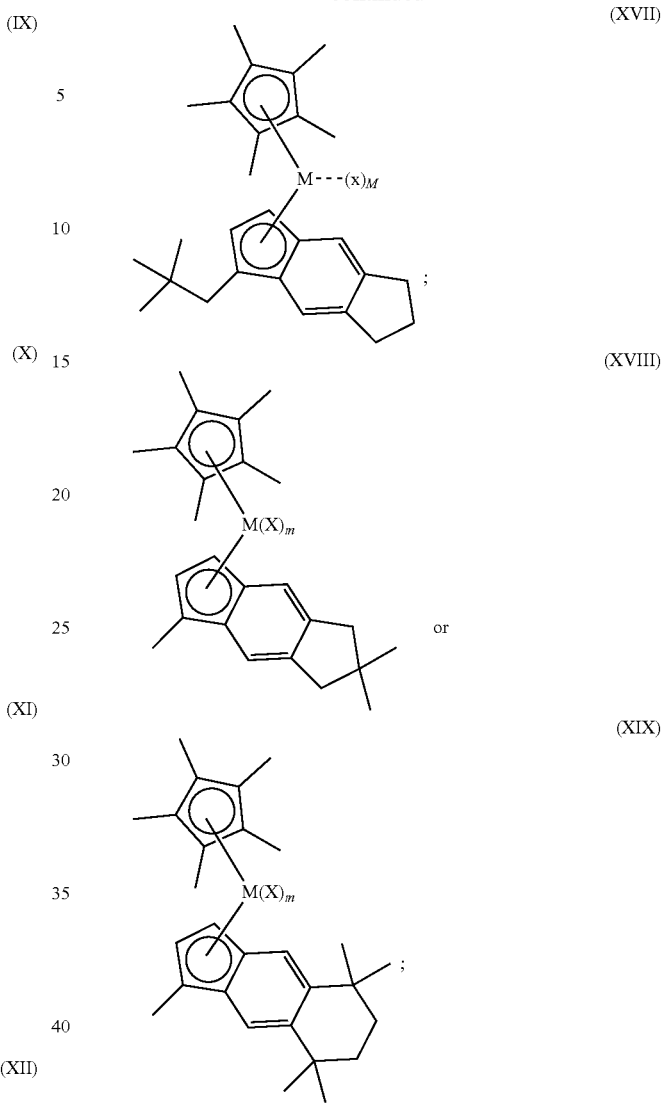

wherein each X is independently a halogen, a hydride, an amide, an alkoxide, a sulfide, a phosphide, a diene, an amine, a phosphine, an ether, or a $C_1$-$C_{20}$ substituted or unsubstituted linear, branched linear, or cyclic hydrocarbyl group, or two or more X moieties may together form a fused ring or ring system; M is a group 3, 4, or 5 transition metal having an integer coordination number of v, such as 3, 4, or 5; and m is an integer equal to v-2, such as 1, 2 or 3.

I. Unsaturated PAO Product

PAOs are polymeric, typically oligomeric, molecules produced from the polymerization reactions of alpha-olefin monomer molecules in the presence of a catalyst system. An unsaturated poly alpha-olefin (uPAO) molecule in the material of the present invention contains a C=C bond therein. Each uPAO molecule has a carbon chain with the largest number of carbon atoms, which is designated the carbon backbone of the molecule. Any non-hydrogen group attached to the carbon backbone other than to the carbon atoms at the very ends thereof is defined as a pendant group. The number of carbon atoms in the longest carbon chain in each pendant group is defined as the length of the pendant group. The backbone typically comprises the carbon atoms derived from the C=C bonds in the monomer molecules participating in the polymerization reactions, and additional carbon atoms from monomer molecules and/or molecules in the catalyst system that form the two ends of the backbone. A typical uPAO molecule can be represented by the following formula (F-1):

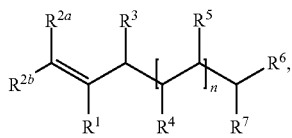

(F-1)

where $R^1$, $R^{2a}$, $R^{2b}$, $R^3$, each of $R^4$ and $R^5$, $R^6$, and $R^7$, the same or different at each occurrence, independently represents a hydrogen or a substituted or unsubstituted hydrocarbyl (preferably an alkyl) group, and n is a non-negative integer corresponding to the degree of polymerization. Where $R^1$, $R^{2a}$ and $R^{2b}$ are all hydrogen, (F-1) represents a vinyl uPAO; where $R^1$ is not hydrogen, and both $R^{2a}$ and $R^{2b}$ are hydrogen, (F-1) represents a vinylidene uPAO; where $R^1$ is hydrogen, and only one of $R^{2a}$ and $R^{2b}$ is hydrogen, (F-1) represents a di-substituted vinylene uPAO; and where $R^1$ is not hydrogen, and only one of $R^{2a}$ and $R^{2b}$ is hydrogen, then (F-1) represents a tri-substituted vinylene uPAO.

Where n=0, (F-1) represents an uPAO dimer produced from the reaction of two monomer molecules after a single addition reaction between two C=C bonds.

Where n=m, m being a positive integer, (F-1) represents a molecule produced from the reactions of m+2 monomer molecules after m+1 steps of linear addition reactions between two C=C bonds.

Thus, where n=1, (F-1) represents a trimer produced from the reactions of three monomer molecules after two steps of linear addition reactions between two C=C bonds.

Assuming a carbon chain starting from $R^1$ and ending with $R^7$ has the largest number of carbon atoms among all straight carbon chains existing in (F-1), that carbon chain starting from $R^1$ and ending with $R^7$ having the largest number of carbon atoms constitutes the carbon backbone of the unsaturated PAO product molecule (F-1). $R^2$, $R^3$, each of $R^4$ and $R^5$, and $R^6$, which can be substituted or unsubstituted hydrocarbyl (preferably alkyl) groups, are pendant groups (if not hydrogen).

If only alpha-olefin monomers are used in the polymerization process, and no isomerization of the monomers and oligomers ever occurs in the reaction system during polymerization, about half, typically at least one more than half, of $R^1$, $R^{2a}$, $R^{2b}$, $R^3$, all $R^4$ and $R^5$, $R^6$, and $R^7$ would be hydrogen, and one of $R^1$, $R^{2a}$, $R^{2b}$, $R^6$, and $R^7$ would be a hydrocarbyl, such as methyl, and about half, typically less than half, of groups $R^1$, $R^{2a}$, $R^{2b}$, $R^3$, all $R^4$ and $R^5$, $R^6$, and $R^7$ would be hydrocarbyl groups introduced from the alpha-olefin monomer molecules. In a specific example of such case, assuming $R^{2a}$ and $R^{2b}$ are hydrogen, $R^3$, all $R^5$, and $R^6$ are hydrogen, and $R^1$, all $R^4$, and $R^7$ have 8 carbon atoms in the longest carbon chains contained therein, and n=8, then the carbon backbone of the (F-1) PAO molecule would comprise 35 carbon atoms, and the average pendant group length of the pendant groups (the initial =$CR^{2a}R^{2b}$ group, and all of $R^4$) would be 7.22 (i.e., (1+8*8)/9). Such an uPAO molecule, which may be produced by polymerizing 1-de-cene using certain metallocene catalyst systems, such as described in greater detail below, can be represented by formula (F-2) below:

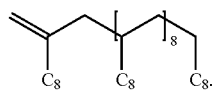

(F-2)

In such a molecule, the longest 5%, 10%, 20%, 40%, 50%, and 100% of the pendant groups have average pendant group length of Lpg(5%) of 8, Lpg(10%) of 8, Lpg(20%) of 8, Lpg(50%) of 8, and Lpg(100%) of 7.22, respectively.

Depending on the polymerization catalyst system used, however, different degrees of isomerization of the monomers and/or oligomers can occur in the reaction system during the polymerization process, resulting in different degrees of substitution on the carbon backbone. In a specific example of such case, assuming $R^{2a}$ and $R^{2b}$ are both hydrogen, $R^3$ and all $R^5$ are methyl, $R^6$ is hydrogen, $R^1$ has 8 carbon atoms in the longest carbon chain contained therein, all $R^4$ and $R^7$ have 7 carbon atoms in the longest carbon chain contained therein, and n=8, then the carbon backbone of the (F-1) uPAO molecule would comprise 34 carbon atoms, and the average pendant group length of the pendant groups (the initial =$CR^{2a}R^{2b}$ group, all $R^4$, and $R^5$) would be ~3.7 (i.e., (1+1+7*8+8*1)/18). Such an uPAO molecule, which may be produced by polymerizing either 1-decene, with a given level and pattern of isomerization, or by polymerizing a combination of 1-decene and 2-decene, using certain non-metallocene catalyst systems, such as described in greater detail below, can be represented by the following formula (F-3):

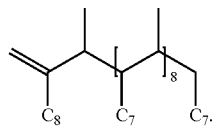

(F-3)

In this molecule, the longest 5%, 10%, 20%, 40%, 50%, and 100% of the pendant groups have average pendant group lengths of Lpg(5%) of 7, Lpg(10%) of 7, Lpg(20%) of 7, Lpg(50%) of 6.3, and Lpg(100%) of 3.7, respectively.

One skilled in the art, with knowledge of the molecular structure or the monomer(s) used in the polymerization step for making the unsaturated PAO product, the process conditions (catalyst used, reaction conditions, etc.), and the polymerization reaction mechanism, inter alia, can approximate the molecular structure of the uPAO molecules, thus the pendant groups attached to the carbon backbone, and hence approximate values of Lpg(5%), Lpg(10%), Lpg (20%), Lpg(50%), and Lpg(100%), respectively.

One skilled in the art can determine the Lpg(5%), Lpg (10%), Lpg(20%), Lpg(50%), and Lpg(100%) values of a given unsaturated PAO product by using separation and characterization techniques available to polymer chemists. For example, gas chromatography/mass spectroscopy machines equipped with boiling point column separator can be used to separate and identify individual chemical species and fractions; and standard characterization methods such as NMR, IR, and UV spectroscopy can be used to further confirm the structures.

The unsaturated PAO products of the present invention may be a homopolymer made from a single alpha-olefin monomer or a copolymer made from a combination of two or more alpha-olefin monomers. In some embodiments, the alpha-olefin monomer(s) can include, consist essentially of, or be 1-hexene, 1-octene, 1-decene, 1-dodecene, or a combination thereof, such as 1-octene, 1-decene, and 1-dodecene.

The unsaturated PAO products of the present invention may be produced by using a catalyst system comprising a specific type of metallocene compound, such as described in detail below. The unsaturated PAO products can be substantially free of the alpha-olefin monomer(s), and may advantageously contain vinylidenes at a high concentration, desirably in the range from $c1$ to $c2$ mol % in total, where $c1$ and $c2$ can be, independently, 80, 85, 90, 91, 92, 93, 94, 95, 96, 96.5, 97, 98, 99, 99.5, or 99.9, based on the total moles of vinyls, vinylidenes, di-substituted vinylenes, and tri-substituted vinylenes, as long as $c1<c2$. In particular embodiments, $c1=90$ and $c2=99$; $c1=91$ and $c2=99$; $c1=92$ and $c2=98$; $c1=93$ and $c2=97$; $c1=96.5$ and $c2=99.9$; or $c1=98$ and $c2=99.5$. Without intending to be bound by a particular theory, it is believed that the high concentrations of vinylidenes can be achieved partly by the unique structure of the metallocene compound used in the catalyst system.

Between the vinylidenes and tri-substituted vinylenes in the unsaturated PAO product of the present invention, tri-substituted vinylenes tend to have a considerably lower concentration than the vinylidenes. In some embodiments, the unsaturated PAO products of the present invention can contain a concentration of tri-substituted vinylenes in the range from $c3$ to $c4$ mol %, based on the total moles of the vinyls, vinylidenes, di-substituted vinylenes, and tri-substituted vinylenes, where $c3$ and $c4$ can be, independently, 0, 0.1, 0.5, 1.0, 1.5, 2.0, 2.5, 3.0, 3.5, 4.0, 4.5, 5.0, 5.5 or 6.0, as long as $c3<c4$. In particular embodiments, $c3=0.5$ and $c4=5.5$; $c3=1.0$ and $c4=5.0$; $c3=0.5$ and $c4=4.0$; $c3=0$ and $c4=4.0$; $c3=0.1$ and $c4=3.5$; or $c3=0.5$ and $c4=2$.

In some embodiments, the unsaturated PAO products of the present invention can desirably contain a high combined concentration of vinylidenes and tri-substituted vinylenes, the combined concentration being in the range from $c5$ to $c6$ mol %, based on the total moles of the vinyls, vinylidenes, di-substituted vinylenes, and tri-substituted vinylenes, where $c5$ and $c6$ can be, independently, 85, 90, 91, 92, 93, 94, 95, 96, 97, 98, 99, or 99.5, based on the total moles of vinyls, vinylidenes, di-substituted vinylenes, and tri-substituted vinylenes, as long as $c5<c6$. In particular embodiments, $c5=90$ and $c6=99.5$; $c5=92$ and $c6=99.5$; $c5=94$ and $c6=99$; $c5=95$ and $c6=99$; or $c5=98$ and $c6=99.5$.

Without intending to be bound by a particular theory, it is believed that vinylidenes and tri-substituted vinylenes are more reactive than di-substituted vinylenes when reacted with many functionalizing agents. Thus, the high concentration of vinylidenes, as well as the high combined concentration of vinylidenes plus tri-substituted vinylenes, in the unsaturated PAO products of the present invention may be particularly advantageous if the unsaturated PAO products are used as intermediates for making functionalized PAO products.

The unsaturated PAO products of the present invention can desirably contain di-substituted vinylenes at a low concentration in the range from $c7$ to $c8$ mol %, based on the total moles of vinyls, vinylidenes, di-substituted vinylenes, and tri-substituted vinylenes, where $c7$ and $c8$ can be 0, 0.1, 0.2, 0.3, 0.4, 0.5, 0.6, 0.7, 0.8, 1.0, 1.2, 1.4, 1.6, 1.8, 2.0, 2.5, 3.0, 3.5, 4.0, 4.5, or 5.0, as long as $c7<c8$. In particular embodiments, $c7=0$ and $c8=4.0$; $c7=0$ and $c8=3.0$; $c7=0$ and $c8=2.0$; $c7=0$ and $c8=1$; $c7=0$ and $c8=1.2$; or $c7=0.1$ and $c8=2.5$. Without intending to be bound by a particular theory, it is believed that such low concentrations of di-substituted vinylenes in the unsaturated PAO products are achieved by the low selectivity toward these olefins in the polymerization reactions, which can be enabled at least partially by the unique structure of the metallocene compound in the catalyst system used in the polymerization reaction.

Depending on the metallocene compound used in the catalyst system, the unsaturated PAO products of the present invention can contain vinyls at a low concentration, e.g., from $c9$ to $c10$ mol %, based on the total moles of vinyls, vinylidenes, di-substituted vinylenes, and tri-substituted vinylenes, where $c9$ and $c10$ can be 0, 0.1, 0.2, 0.3, 0.4, 0.5, 0.6, 0.7, 0.8, 1.0, 1.2, 1.4, 1.6, 1.8, 2.0, 2.5, 3.0, 3.5, 4.0, 4.5, or 5.0, as long as $c9<c10$. In particular embodiments, $c9=0$ and $c10=4.0$; $c9=0$ and $c10=3.0$; $c9=0$ and $c10=2$; $c9=0$ and $c10=1.6$; $c9=0$ and $c10=1.0$; or $c9=0.1$ and $c10=1.2$. Without intending to be bound by a particular theory, it is believed that such low concentration of vinyls in the unsaturated PAO products are achieved by the low selectivity toward vinyls in the polymerization reactions, which can be enabled by choosing the molecular structure of the metallocene compound in the catalyst system used in the polymerization reaction.

In some embodiments, the unsaturated PAO products of the present invention can desirably contain a low combined concentration of vinyls and di-substituted vinylenes, the combined concentration being in the range from $c11$ to $c12$ mol %, based on the total moles of the vinyls, vinylidenes, di-substituted vinylenes, and tri-substituted vinylenes, where $c11$ and $c12$ can be, independently, 0, 0.1, 0.2, 0.3, 0.4, 0.5, 0.6, 0.7, 0.8, 1.0, 1.2, 1.4, 1.6, 1.8, 2.0, 2.5, 3.0, 3.5, 4.0, 4.5, 5.0, 5.5, or 6.0, as long as $c11<c12$. In particular embodiments, $c11=0$ and $c12=5.0$; $c11=0$ and $c12=4.0$; $c11=0.5$ and $c12=2$; $c11=0.5$ and $c12=4.5$; or $c11=0.8$ and $c12=5.0$.

Thus, the unsaturated PAO products of the present invention can typically comprise a plurality of PAO molecules, which may be the same or different. Each uPAO molecule can comprise a plurality of pendant groups, which may be the same or different, and the longest 5%, 10%, 20%, 40%, 50%, and 100% of the pendant groups of all of the olefin molecules of the unsaturated PAO product have an average pendent group length of $Lpg(5\%)$, $Lpg(10\%)$, $Lpg(20\%)$, $Lpg(40\%)$, $Lpg(50\%)$, and $Lpg(100\%)$, respectively. It is preferred that at least one of the following conditions are met:

(i) $a1 \leq Lpg(5\%) \leq a2$, where $a1$ and $a2$ can be, independently, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0 15.5, or 16.0, as long as $a1 \leq a2$;

(ii) $b1 \leq Lpg(10\%) \leq b2$, where $b1$ and $b2$ can be, independently, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, or 15.0, as long as $b1 \leq b2$;

(iii) $c1 \leq Lpg(20\%) \leq c2$, where $c1$ and $c2$ can be, independently, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, or 15.0, as long as $c1 \leq c2$;

(iv) $d1 \leq Lpg(40\%) \leq d2$; where $d1$ and $d2$ can be, independently, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, or 15.0, as long as $d1 \leq d2$;

(v) e1≤Lpg (50%)≤e2; where e1 and e2 can be, independently, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, or 14.0, as long as e1≤e2; and (vi) f1≤Lpg(100%)≤f2, where f1 and f2 can be, independently, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, or 13.0, as long as f1≤f2.

In some embodiments, at least 60% of the pendent groups on olefin molecules in the unsaturated PAO product are straight chain alkyls having at least 4 (e.g., at least 6, at least 8, or at least 10) carbon atoms. In particular embodiments, at least 90% of the pendent groups on the olefin molecules in the unsaturated PAO product are straight chain alkyls having at least 4 (e.g., at least 6, at least 8, or at least 10) carbon atoms.

The unsaturated PAO products of the present invention may have various levels of regio-regularity. For example, each uPAO molecule may be substantially atactic, isotactic, or syndiotactic. A category of metallocene compounds can lack C1, C2, and $C_s$ symmetry. Without intending to be bound by a particular theory, it is believed that PAO materials made by using such asymmetrical metallocene-based catalyst system can tend to be atactic.

The unsaturated PAO products of the present invention can have viscosity varying in a broad range. For example, the unsaturated PAO product may have a KV100 in a range from 1 to 5000 cSt, such as 1 to 3000 cSt, 2 to 2000 cSt, 2 to 1000 cSt, 2 to 800 cSt, 2 to 600 cSt, 2 to 500 cSt, 2 to 400 cSt, 2 to 300 cSt, 2 to 200 cSt, or 5 to 100 cSt. The exact viscosity of the unsaturated PAO product can be controlled by, e.g., monomer used, polymerization temperature, polymerization reactor residence time, catalyst used, concentration of catalyst used, distillation and separation conditions, and mixing multiple unsaturated PAO products with different viscosity.

In addition, the unsaturated PAO products of the present invention advantageously have a low polydispersity index (PDI) in the range from about 1.0 to about 5.0 (e.g., from 1.2 to 4.0, from 1.3 to 3.0, from 1.4 to 2.5, from 1.5 to 2.0, or from 1.6 to 1.8). A narrow molecular weight distribution of the uPAO molecules can be achieved by using metallocene-compound-based catalyst systems in the polymerization step under controlled polymerization conditions (temperature fluctuation, residence time, and the like). Such narrow PDI is desirable in that it defines a material with a high degree of homogeneity in molecular weight, molecular size, rheology behavior, viscosity index, and degrading behavior (such as shear stability and oxidation stability). From an olefin mixture with such degree of homogeneity one can produce a functionalized material having a similar degree of homogeneity as well.

In general, the olefin mixture in the unsaturated PAO products of the present invention can have an average molecular weight that can vary widely (and correspondingly, a KV100 that can vary widely). In some embodiments, the uPAO olefin mixture can have a number average molecular weight of Mn, where Mn1≤Mn≤Mn2, where Mn1 and Mn2 can be, independently, 150, 200, 300, 400, 500, 600, 700, 800, 900, 1000, 1100, 1200, 1300, 1400, 1500, 1700, 2000, 2500, 3000, 3500, 4000, 4500, 5000, 6000, 7000, 8,000, 9000, or 10000 g/mol, as long as Mn1<Mn2. In some embodiments, the uPAO olefin mixture can have a number average molecular weight of 3000 g/mol or less, e.g., 2500 g/mol or less, 2000 g/mol or less, 1700 g/mol or less, 1500 g/mol or less, 1400 g/mol or less, 1300 g/mol or less, 1200 g/mol or less, 1100 g/mol or less, 1000 g/mol or less, 900 g/mol or less, 800 g/mol or less, 700 g/mol or less, 650 g/mol or less, 620 g/mol or less, 600 g/mol or less, 520 g/mol or less, 500 g/mol or less, 400 g/mol or less, 380 g/mol or less, 370 g/mol or less, 360 g/mol or less, 350 g/mol or less, 340 g/mol or less, 330 g/mol or less, or 320 g/mol or less; typically, as the product is preferred to exclude olefin monomers but may include dimers and higher mers, the number average molecular weight can optionally be at least 100 g/mol, e.g., at least 150 g/mol or at least 200 g/mol, depending upon the molecular weight of a monomeric feed olefin component.

The unsaturated PAO products of the present invention may additionally comprise saturated hydrocarbons. The saturated hydrocarbons may be produced in situ in the polymerization step of the alpha-olefin for making the unsaturated PAO products, e.g., where the polymerization is conducted in the presence of a hydrogen-containing atmosphere. Alternatively or additionally, the saturated hydrocarbons may be produced by a partial hydrogenation of a portion of the unsaturated PAO product as produced from the polymerization step. Further additionally or alternatively, the saturated hydrocarbon may be blended with an olefin mixture to obtain a mixture of desired property and composition. Nonetheless, it is desired that the unsaturated PAO products of the present invention comprise the vinylidenes, tri-substituted vinylenes, optional vinyls and optional di-substituted vinylenes at a total concentration thereof of at least 50 wt % (e.g., at least 60, 65, 70, 75, 80, 85, 90, 91, 92, 93, 94, 95, 96, 97, 98, 99, 99.5, or 99.8 wt %), based on total weight of the unsaturated PAO product.

In general, it is desired that the unsaturated PAO product of the present invention has a bromine number in a range from Nb(PAO)1 to Nb(PAO)2, where Nb(PAO)1 and Nb(PAO)2 can be, independently, 1.0, 1.5, 2.0, 2.5, 3.0, 3.5, 4.0, 4.5, 5.0, 6.0, 7.0, 8.0, 9.0, or even 10.0, 15.0, 10.0, as long as Nb(PAO)1<Nb(PAO)2. Desirably, a great majority, such as at least 80, 85, 90, 95, 98, or even 99 mol % of the molecules in the unsaturated PAO product of the present invention may be unsaturated. Desirably, each unsaturated PAO molecule is capable of addition reaction with one Br$_2$ molecule to obtain a 1,2-dibromo-derivative thereof.

Molecular structures of exemplary vinylidene uPAOs made from a mixture of 1-octene and 1-dodecene alpha-olefin monomers at a molar ratio of 4:1 can be schematically represented by formula (F-V) as follows, where n can be any integer.

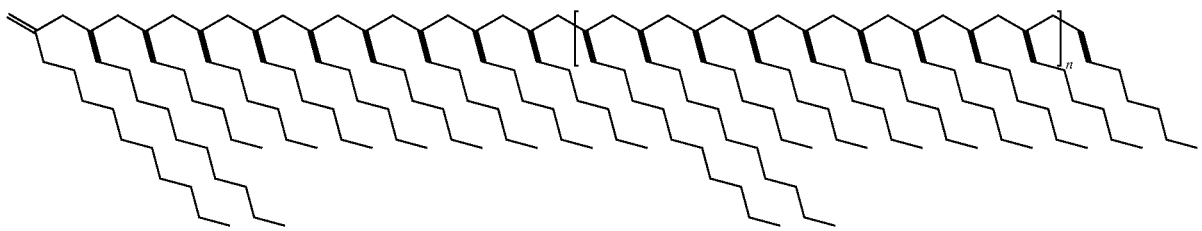

The two $C_{10}$ pendant groups are shown to be next to each other. In real molecules, they may be randomly distributed among all of the pendant groups. The structure shows nearly 100% isotacticity, i.e., 100 mol % of (m,m)-triads in the structure. In real molecules, a small fraction may be (m,r)- or (r,r)-triads. Nonetheless, each of the long pendant groups can extend to form a substantially linear chain, and interact with other long straight carbon chains from other uPAO molecules and other molecules in its vicinity.

Because of the presence of the C=C bonds in the uPAO molecules, when exposed to $O_2$ molecules (such as when exposed to air), the unsaturated PAO product can be oxidized if not protected by a more reactive material toward $O_2$. To that end, in the unsaturated PAO products, anti-oxidant materials may be added to prolong shelf life and facilitate handling, storage, and transportation thereof. Such anti-oxidants can include, but are not limited to, those anti-oxidants typically used in lubricant base stocks and lubricating oil compositions. Non-limiting examples of such anti-oxidants and the use quantity thereof are given in paragraphs [0101]-[0108], pages 9 and 10 of U.S. Patent Application Publication No. 2010/0087349, the content of which is hereby incorporated by reference in its entirety.

II. Hydrogenation of the Unsaturated PAO Products

The unsaturated PAO products made by the method of the present invention can be directly used as a lubricating oil base stock and other applications because it can be made to have the desired physical properties, particularly rheological properties interesting for such applications. However, due to the presence of C=C bonds on a large portion, if not all, of the uPAO molecules, direct use thereof as a lubricating oil base stock can cause stability issues to the oil if the oil is exposed to an oxidative environment, such as the air. Thus, in general, for lubricating oil applications, it may be desirable to hydrogenate the unsaturated PAO products to remove at least a portion, preferably a major portion, of the C=C bonds of the PAO molecules. For example, one can subject the unsaturated PAO product of the present invention to a step of hydrogenation by contacting it with a hydrogen-containing atmosphere in the presence of a hydrogenation catalyst, such as one containing one or more of Fe, Co, Ni, precious metals (such as Ru, Rh, Pd, Os, Ir, Pt), and the like. Because of the composition of the unsaturated PAO product of the present invention, they can be advantageously hydrogenated to convert a great majority of the C=C bonds present in the olefin molecules into carbon-carbon single bonds, thereby achieving a material that is substantially aliphatic and saturated (e.g., which can be characterized by a low Bromine number of no greater than 5.0, no greater than 4.0, no greater than 3.0, or no greater than 2.0). Such hydrogenated, largely aliphatic hydrocarbon materials can have one or more of high viscosity index, low pour point, high oxidation stability, and high shear stability. They can advantageously be used as, e.g., base stocks for lubricant compositions, such as those used in internal combustion engines, automotive grease oils, industrial grease oils, gear box oils, and the like.

The hydrogenated PAO products made from hydrogenating the unsaturated PAO products can generally exhibit viscosity, molecular weight distribution, pendent group distribution, polydispersity index, that are almost identical with those of precursor unsaturated PAO products. Thus, the hydrogenated PAO products of the present invention can have a KV100 in a range from 1 to 5000 cSt, such as 1 to 3000 cSt, 2 to 2000 cSt, 2 to 1000 cSt, 2 to 800 cSt, 2 to 600 cSt, 2 to 500 cSt, 2 to 400 cSt, 2 to 300 cSt, 2 to 200 cSt, or 5 to 100 cSt.

The hydrogenated PAO products of the present invention can advantageously have a low polydispersity index (PDI) in the range from about 1.0 to about 5.0 (e.g., from 1.2 to 4.0, from 1.3 to 3.0, from 1.4 to 2.5, from 1.5 to 2.0, or from 1.6 to 1.8). Such narrow PDI can be desirable, in that it defines a material with a high degree of homogeneity in molecular weight, molecular size, rheology behavior, viscosity index, and degrading behavior (such as shear stability and oxidation stability).

The hydrogenated PAO products of the present invention can have a number average molecular weight of Mn, where $Mn1 \leq Mn \leq Mn2$, where Mn1 and Mn2 can be, independently, 150, 200, 300, 400, 500, 600, 700, 800, 900, 1000, 1100, 1200, 1300, 1400, 1500, 1700, 2000, 2500, 3000, 3500, 4000, 4500, 5000, 6000, 7000, 8,000, 9000, or 10000, as long as Mn1<Mn2. In some embodiments, the hydrogenated PAO product can have a number average molecular weight of 3000 g/mol or less, e.g., 2500 g/mol or less, 2000 g/mol or less, 1700 g/mol or less, 1500 g/mol or less, 1400 g/mol or less, 1300 g/mol or less, 1200 g/mol or less, 1100 g/mol or less, 1000 g/mol or less, 900 g/mol or less, 800 g/mol or less, 700 g/mol or less, 600 g/mol or less, or 500 g/mol or less; typically, as the product is preferred to exclude olefin monomers but may include dimers and higher mers, the number average molecular weight can optionally be at least 100 g/mol, e.g., at least 150 g/mol or at least 200 g/mol, depending upon the molecular weight of a monomeric feed olefin component.

The hydrogenated PAO can be used as a high-quality API Group IV base stock. Various grades of the hydrogenated mPAO with KV100 varying from very low such as 1 cSt to very high such as 5,000 cSt can be made by using the method of the present invention, and used for blending with each other and other API Group I, II, III, IV, or V base stocks to make high-quality lubricating oil formulations, such as internal combustion engine oils, automobile drive line oils, industrial oils, greases, and the like. Furthermore, the mPAO can be used as heat transfer oil (e.g., transformer oil), processing oil, hydraulic power transfer oil, and the like.

III. Functionalization of the Unsaturated PAO Products

The unsaturated PAO products of the present invention as described above, desirably produced by polymerization of alpha-olefin and/or olefinic monomers in the presence of a metallocene-compound-based catalyst system, can be advantageously used as a chemical intermediate for making many products, especially those comprising a PAO molecule moiety and one or more functional groups. The hydrocarbon molecules in the unsaturated PAO products, if prepared from the polymerization of olefins/alpha-olefins containing only one C=C double bond in their pre-polymerized molecules, can tend to comprise no more than one C=C bond each, with the rest of the molecular structure typically consisting of C—C bonds and C—H bonds.

The C=C bonds present in the molecules of the unsaturated PAO product of the present invention are highly reactive, and therefore can react with multiple, different types of chemical agents having useful functional groups, thereby creating a PAO molecule further comprising a functional group bonded thereto. The functional group can comprise, in turn, other functional groups, which can react with additional chemical agents, bringing additional or different functional groups to the final molecule. The hydrocarbon substrate (i.e., the PAO structure) of thus functionalized PAO can impart desired properties to the functionalized material, such as solubility in organic media or hydrophobicity, and the functional groups can impart other desired properties to the final material, such as polarity, hydrophilicity (thus, solubility in aqueous media), and the like, making the final material particularly useful where such dual properties are desired (e.g., detergents).

U.S. Publication No. 2014/0087986 discloses multiple methods for making functionalized PAO from unsaturated PAO products produced by polymerization of alpha-olefin monomers in the presence of a metallocene-compound-based catalyst system. The entirety of the invention of this reference is incorporated by reference.

It is highly desired that upon functionalization of the unsaturated PAO product, the C=C double bond in the reacted uPAO molecule becomes saturated (i.e., each carbon atom in the original C=C bond is then bonded to four atoms). This can be achieved by using functionalization agents reactive substantially only toward the C=C bonds, but substantially inert toward the C—C bonds and C—H bonds in the uPAO olefin molecules under the functionalization conditions. Given that each uPAO olefin molecule comprises typically only one C=C bond, the uPAO olefin molecule would then become saturated upon such functionalization reaction.

Upon functionalization of the C=C bond in the uPAO olefin molecule, the overall structure of the functionalized PAO molecule would be substantially similar to that of a hydrogenated PAO molecule where the C=C bond has been saturated by hydrogenation as described above. Assuming that the bond between the functional group(s) to the carbon atom(s) is not significantly less robust than the C—C and C—H bonds, and assuming the functional group(s) per se are not significantly less robust than a pendant group on the PAO molecule under the use conditions, one can expect a stable oligomeric/polymeric structure retaining at least some of the interesting and useful properties of a saturated PAO molecule, such as one or more of viscosity index, oxidation stability, shear stability, Bromine number, and the like. The retained properties can make the functionalized PAO material particularly useful in applications typical for the saturated PAO materials, such as lubricating oil compositions, and the like.

It is highly desirable that the functionalization agent used to functionalize the unsaturated PAO product is highly selective toward reacting with the C=C bond only, and is substantially inert with respect to the C—C bonds and C—H bonds on the uPAO molecules. This can ensure the production of functionalized PAO molecules each comprising one or two functional group(s) only, and a complete functionalization of substantially all of the uPAO molecules if desired. In applications such as lubricating oil compositions, because of the high reactivity of C=C bonds in the uPAO molecules, it may be desired that substantially all of the C=C bonds in the uPAO molecules are saturated before the functionalized PAO material is put into the oil compositions, either as a base stock or as an additive.

Additionally or alternatively, one may also functionalize the uPAO molecules by substituting one or more of the hydrogen atoms on the carbon backbone or one of the pendant groups with a functional group by using chemical agents known to be reactive with C—H bonds. Because a uPAO molecule typically comprise many C—H bonds at multiple locations, such reaction would be less selective than selective functionalization of C=C bonds by using a functionalization agent that is inert to the C—H bonds, and can result in very large number of very different molecules, and thus is less desirable than functionalization selective toward the C=C bonds only.

Additionally or alternatively, the uPAO products of the present invention can be functionalized by reaction between the unsaturated C=C bonds of the uPAO molecules and a chemical reagent. The chemical reagent may contain the moiety to be directly or indirectly reacted with the reactive portion(s) of the uPAO, optionally in the presence of an appropriate catalyst or facilitating agent. Alternatively, the chemical reagent may be a precursor to be directly or indirectly reacted with the reactive portion(s) of the uPAO, optionally in the presence of an appropriate catalyst or facilitating agent, followed by at least one other treatment and/or chemical reagent reaction, also optionally in the presence of the same or a different appropriate catalyst or facilitating agent, in order to effectuate a desired final functionality at the reactive portion(s) of the uPAO. Further alternatively, the chemical reagent may be a co-reactant to be pre-reacted or simultaneously reacted with another chemical reagent for direct or indirect reaction with the reactive portion(s) of the uPAO, optionally in the presence of an appropriate catalyst or facilitating agent.

Optionally, more than one type of functionality can be desired, such that the functionalization can occur simultaneously (effectuating a variety of functionalities in a single result), in series, in parallel (provided two parallel reactions do not countermand each other), or some combination thereof. Whether one or more functionalities are desired, the reaction can be of any variety capable of effectively accomplishing the functionalization, e.g., liquid-phase chemistry, gas-liquid interfacial chemistry, solid-liquid surface chemistry, gaseous oxidation, gaseous oxidation followed by some other functionalization mechanism, plasma oxidation, plasma oxidation followed by some other functionalization mechanism, radical formation, radical formation followed by some other functionalization mechanism, or the like. The ultimately desired functional group(s) can be tailored to the particular end-use application, e.g., including but not limited to moieties containing an oxygen atom, a nitrogen atom, a sulfur atom, a phosphorus atom, a boron atom, a silicon atom, a halogen atom, or a combination thereof. The extent to which functionalization can be accomplished is another variable that can be tailored to the particular end-use application. Functionalization (single or multiple) can be partial or substantially complete (i.e., in which substantially all the unsaturations of the uPAO can be converted into a functional moiety, such as a heteroatom-containing moiety).

IV. The Catalyst System

In embodiments, the catalyst system comprises a catalyst compound, preferably a metallocene compound which is activated by one or more activators. The catalyst system may further include a solvent, a support, one or more scavengers, accelerators, and/or the like.

IV.1 the Metallocene Compound

The initial part to a catalyst system described herein is a metallocene compound. The metallocene compound used in the process of the present invention for making PAOs generally has a structure represented by formula (F-MC) below comprising a first cyclopentadienyl ring with carbon atoms directly connected with $R^1$, $R^2$, $R^3$, $R^4$, and $R^5$, and a second cyclopentadienyl ring with carbon atoms directly connected with $R^{12}$, $R^{13}$, $R^{14}$, $R^{15}$, and $R^{16}$.

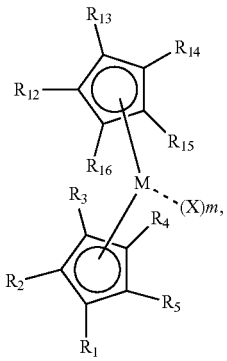

(F-MC)

wherein:

each $R^1$, $R^2$, and $R^3$ is, independently, hydrogen or a substituted or unsubstituted linear, branched linear, or cyclic $C_1$ to $C_{20}$, preferably $C_1$-$C_8$, hydrocarbyl group, wherein one of $R^1$, $R^2$, and $R^3$ is a substituted or unsubstituted linear, branched linear, or cyclic $C_1$ to $C_{20}$, preferably $C_1$-$C_8$, hydrocarbyl group, and optionally two of $R^1$, $R^2$, and $R^3$ are each a hydrogen;

$R^4$ and $R^5$ are each independently a substituted or unsubstituted linear, branched linear, or cyclic $C_1$-$C_{30}$ hydrocarbyl group, or $R^4$ and $R^5$, taken together with the carbon atoms in the first cyclopentadienyl ring to which they are directly connected, collectively form one or more substituted or unsubstituted rings annelated to the first cyclopentadienyl ring;

$R^{12}$, $R^{13}$, $R^{14}$, and $R^{15}$ are each independently a hydrogen, or a substituted or unsubstituted linear, branched linear, or cyclic $C_1$ to $C_{20}$, preferably $C_1$-$C_8$, hydrocarbyl group;

$R^{16}$ is a hydrogen, a substituted or unsubstituted linear, branched linear, or cyclic $C_1$ to $C_{20}$, preferably $C_1$-$C_8$, hydrocarbyl group or silylcarbyl group, preferably at least three (preferably at least four, preferably all five) of $R^{12}$, $R^{13}$, $R^{14}$, $R^{15}$, and $R^{16}$ are not hydrogen, optionally two or more of $R^{12}$, $R^{13}$, $R^{14}$, $R^{15}$ and $R^{16}$ moieties may together form a fused ring or ring system;

M is a group 3, 4, or 5 transition metal (preferably a group 4 transition metal, preferably Hf, Ti, or Zr), having an integer coordination number of v, preferably v is 3, 4, or 5;

each X is independently a halogen, a hydride, an amide, an alkoxide, a sulfide, a phosphide, a diene, an amine, a phosphine, an ether, or a $C_1$-$C_{20}$ substituted or unsubstituted linear, branched linear, or cyclic hydrocarbyl group, or optionally two or more X moieties may together form a fused ring or ring system; and m is an integer equal to v-2 (preferably m is 1, 2 or 3, preferably 2), preferably M is Zr or Hf, v is 4 and m is 2.

Preferably, in any formula herein, $R^2$ is hydrogen.

In some embodiments, preferred examples of $C_1$-$C_{20}$ and/or $C_1$-$C_{30}$ substituted or unsubstituted linear, branched linear, or cyclic hydrocarbyl groups can include, but are not necessarily limited to: methyl, ethyl, n-propyl, isopropyl, n-butyl, 1-methylpropyl, 1-ethylethyl, n-pentyl, 1-methyl-pentyl, 1-ethylpropyl, 1-hexyl, 1-methylpentyl, 1-ethyl-butyl, 1-propylpropyl, optionally substituted cyclohexyl, optionally substituted phenyl, optionally substituted benzyl, and the like, and any ethylenically unsaturated group that can be derived from them by eliminating one available hydrogen group from each of two adjacent carbon atoms therein.

In some embodiments, M comprises, consists essentially of, or is Ti, Zr, and/or Hf. In a preferred embodiment, M comprises, consists essentially of, or is Zr and/or Hf. In some embodiments, the coordination number of the transition metal M is 4, and thus m is 2.

In some embodiments, each X is independently a halogen or a substituted or unsubstituted linear, branched linear, or cyclic $C_1$-$C_6$ hydrocarbyl group, e.g., a methyl, an ethyl, a propyl, a butyl, a phenyl, a benzyl, a chloride, a bromide, or an iodide.

Preferably, each $R^1$, $R^2$, and $R^3$ is, independently, hydrogen or a substituted or unsubstituted linear, branched linear, or cyclic $C_1$-$C_6$ hydrocarbyl group (e.g., a methyl, an ethyl, a propyl, a butyl, a cyclohexyl, or a phenyl).

In some embodiments, one of $R^1$, $R^2$, and $R^3$ is a substituted or unsubstituted linear, branched linear, or cyclic $C_1$-$C_6$ hydrocarbyl group (e.g., a methyl, an ethyl, a propyl, a butyl, a cyclohexyl, or a phenyl, such as methyl), and (the other) two of $R^1$, $R^2$, and $R^3$ are each a hydrogen.

In some embodiments, $R^1$ and $R^3$ are each individually a substituted or unsubstituted linear, branched linear, or cyclic $C_2$-$C_6$ hydrocarbyl group (e.g., an ethyl, a propyl, a butyl, a cyclohexyl, or a phenyl), and $R^2$ is a hydrogen. In another embodiment, $R^1$ and $R^3$ are each a methyl group and $R^2$ is a hydrogen.

In some embodiments of the invention, one of $R^1$ and $R^3$ is a tertiary or quaternary beta branched ligand in which the alpha and beta atoms are a Group 14 atom, e.g., carbon, silicon, germanium, and two or more, preferably three, substituted or unsubstituted linear, branched linear, or cyclic $C_1$-$C_{18}$, preferably $C_1$-$C_8$, hydrocarbyl groups attached to the beta atom. Examples include neopentyl, beta trialkylsi-lyl-methyl, and beta-trialkylgermanyl-methyl moieties.

In some embodiments, $R^4$ and $R^5$, taken together with the carbon atoms in the first cyclopentadienyl ring to which they are directly connected, collectively form a substituted or unsubstituted phenyl ring annelated to the first cyclopentadienyl ring. In such embodiments, the four phenyl ring carbons not connected to the first cyclopentadienyl ring are each independently bonded to a hydrogen or a substituted or unsubstituted linear, branched linear, or cyclic $C_1$-$C_6$ hydrocarbyl group (e.g., a methyl, an ethyl, a propyl, a butyl, a cyclohexyl, or a phenyl). In some such embodiments, at least two (e.g., at least three or all four) of the four phenyl ring carbons not connected to the first cyclopentadienyl ring are connected to a hydrogen.

In some embodiments, $R^4$ and $R^5$, taken together with the carbon atoms in the first cyclopentadienyl ring to which they are directly connected, collectively form a substituted or unsubstituted naphthenyl ring annelated to the first cyclopentadienyl ring. In any embodiment, the annelated ring or rings may comprise saturated ring carbons, unsaturated ring compounds, or a combination of saturated and unsaturated carbon atoms, for example, a non-aromatic ring or a combination of aromatic and non-aromatic rings. In such embodiments, the metallocene compound can have a structure represented by formula (F-MC2) below:

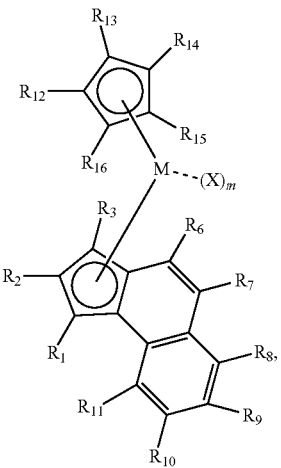

(F-MC2)

wherein $R^1$, $R^2$, $R^3$, $R^{12}$, $R^{13}$, $R^{14}$, R, $R^{16}$, M, X, v, and m are as defined in F-MC; and $R^6$, $R^7$, $R^8$, $R^9$, $R^{10}$, and $R^{11}$ are each independently a hydrogen or a substituted or unsubstituted linear, branched linear, or cyclic $C_1$-$C_6$ hydrocarbyl group (e.g., a methyl, an ethyl, a propyl, a butyl, a cyclohexyl, or a phenyl), optionally $R^1$ and $R^{11}$ are not both hydrocarbyl groups.

In some embodiments of formula (F-MC2), at least two (e.g., at least three, at least four, at least five, or all six) of $R^6$, $R^7$, $R^8$, $R^9$, $R^{10}$, and $R^{11}$ are a hydrogen.

Alternately, in some embodiments of formula (F-MC2), both $R^1$ and $R^{11}$ are hydrocarbyl, alternately $C_1$ to $C_{12}$ hydrocarbyl. Alternately, in some embodiments of formula (F-MC2), both $R^1$ and $R^{11}$ are not hydrocarbyl.

In some embodiments, the metallocene compound can have a structure represented by formula (F-MC2):

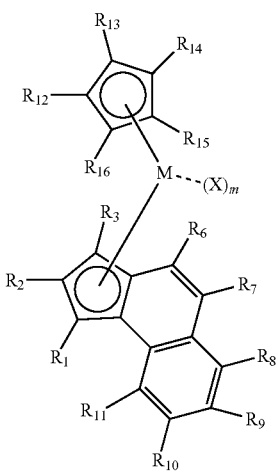

(F-MC2)

wherein:
$R^1$, $R^2$, $R^3$, $R^{16}$ are as defined in F-MC;
$R^6$, $R^7$, $R^8$, $R^9$, $R^{10}$, and $R^{11}$ are each independently a hydrogen or a substituted or unsubstituted linear, branched linear, or cyclic $C_1$ to $C_{20}$, preferably $C_1$-$C_8$, preferably $C_1$-$C_6$, hydrocarbyl group (e.g., a methyl, an ethyl, a propyl, a butyl, a cyclohexyl, or a phenyl), preferably $R^1$ and $R^{11}$ are not both hydrocarbyl groups; and one of $R^1$ and $R^3$ is a substituted or unsubstituted linear, branched linear, or cyclic $C_1$-$C_4$ hydrocarbyl group (e.g., a methyl, an ethyl, a propyl, or a butyl), or $R^2$ is a hydrogen, and either of $R^1$ and $R^3$ is a hydrogen;

$R^{12}$, $R^{13}$, $R^{14}$, and $R^{15}$ are each independently a hydrogen, or a substituted or unsubstituted linear, branched linear, or cyclic $C_1$ to $C_{20}$, preferably $C_1$-$C_8$, hydrocarbyl group (e.g., a methyl, an ethyl, a propyl, a butyl, a hexyl, an octyl, a cyclohexyl, a phenyl, or a benzyl), $R^{16}$ is a hydrogen, a substituted or unsubstituted linear, branched linear, or cyclic $C_1$ to $C_{20}$, preferably $C_1$-$C_8$, hydrocarbyl group (e.g., a methyl, an ethyl, a propyl, a butyl, a hexyl, an octyl, a cyclohexyl, a phenyl, or a benzyl) or silylcarbyl group, preferably at least three (e.g., at least four or all five) of $R^{12}$, $R^{13}$, $R^{14}$, $R^{15}$, and $R^{16}$ are not hydrogen further, optionally two or more of $R^{12}$, $R^{13}$, $R^{14}$, $R^{15}$ and $R^{16}$ moieties may together form a fused ring or ring system;

M comprises, consists essentially of, or is Zr and/or Hf;
m is 2; and each X is independently a methyl, an ethyl, a propyl, a butyl, a hexyl, an octyl, a phenyl, a benzyl, a chloride, a bromide, or an iodide.

Both the first and second Cp rings in the metallocene compound of the present invention are substituted. One, but preferably not both, of the first and second Cp rings can be annelated to one or more rings.

This invention also relates to catalyst compounds represented by the formula:

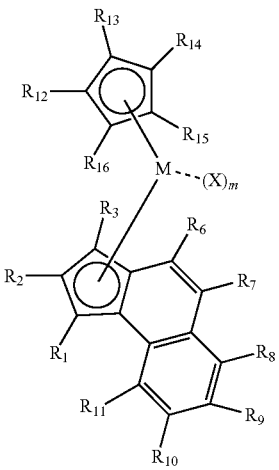

wherein $R^1$, $R^3$, $R^{12}$, $R^{13}$, $R^{14}$, $R^{15}$, $R^{16}$, M, X, v, and m are as defined for F-MC, $R^6$, $R^7$, $R^8$, $R^9$, $R^{10}$, and $R^{11}$ are as defined for F-MC2, and $R^2$ is hydrogen, or a substituted or unsubstituted linear, branched linear, or cyclic $C_1$-$C_{20}$, preferably $C_2$ to $C_{20}$, preferably $C_2$ to $C_8$, hydrocarbyl group (preferably hydrogen).

Preferably, in any embodiment of any formula herein, M is Hf or Zr; m is 2;

each X is independently a halogen, a hydride, an amide, an alkoxide, a sulfide, a phosphide, a diene, an amine, a phosphine, an ether, or a $C_1$-$C_{20}$ substituted or unsubstituted linear, branched linear, or cyclic hydrocarbyl group, or optionally two or more X moieties may together form a fused ring or ring system (preferably each X is independently Cl, Br, Me, Et, Pr, or Bu);

one of $R^1$ and $R^3$ is hydrogen and the other of $R^1$ and $R^3$ is a substituted or unsubstituted linear, branched linear, linear, or cyclic hydrocarbyl group (preferably a $C_1$ to $C_{12}$ hydrocarbyl group, preferably a $C_1$ to $C_4$ alkyl group, preferably methyl, ethyl, ethenyl and isomers of propyl, butyl, pentyl, hexyl, heptyl, octyl, nonyl, decyl, undecyl, or dodecyl) or a branching group;

$R^2$ is hydrogen, or a substituted or unsubstituted linear, branched linear, or cyclic $C_1$-$C_8$ hydrocarbyl group (preferably a $C_2$ to $C_6$ hydrocarbyl group, preferably a $C_1$ to $C_4$ alkyl group, preferably methyl, ethyl, ethenyl and isomers of propyl, butyl, pentyl, hexyl, heptyl, octyl, nonyl, decyl, undecyl, or dodecyl);

$R^6$, $R^7$, $R^8$, $R^9$, $R^{10}$, and $R^{11}$ are each independently a hydrogen or a substituted or unsubstituted linear, branched linear, or cyclic $C_1$-$C_6$ hydrocarbyl group (preferably a $C_1$ to $C_4$ hydrocarbyl group, preferably a $C_1$ to $C_4$ alkyl group, preferably a $C_1$ to $C_4$ alkyl group, preferably methyl, ethyl, ethenyl and isomers of propyl, butyl, pentyl, hexyl, heptyl, octyl, nonyl, decyl, undecyl, or dodecyl); and $R^{12}$, $R^{13}$, $R^{14}$, $R^{15}$ and $R^{16}$ are each independently a hydrogen, or a substituted or unsubstituted linear, branched linear, or cyclic $C_1$-$C_8$ hydrocarbyl group (preferably a $C_1$ to $C_6$ hydrocarbyl group, preferably a $C_1$ to $C_4$ alkyl group, preferably a $C_1$ to $C_4$ alkyl group, preferably methyl, ethyl, ethenyl and isomers of propyl, butyl, pentyl, hexyl, heptyl, octyl, nonyl, decyl, undecyl, or dodecyl), preferably at least three (preferably at least four, preferably all five) of $R^{12}$, $R^{13}$, $R^{14}$, $R^{15}$ and $R^{16}$ are not hydrogen optionally two or more of $R^{12}$, $R^{13}$, $R^{14}$, $R^{15}$ and $R^{16}$ moieties may together form a fused ring or ring system.

In a preferred embodiment in any formula described herein, $R^1$ is hydrogen and $R^3$ is methyl, ethyl, ethenyl and isomers of propyl, butyl, pentyl, hexyl, heptyl, octyl, nonyl, decyl, undecyl, or dodecyl, preferably methyl.

In some embodiments, the metallocene compound used in the process of the present invention for making PAOs generally has a structure represented by formula (I) below comprising an indenyl ring with carbon atoms directly connected with $R^1$, $R^2$, $R^3$, and a cyclopentadienyl ring with carbon atoms directly connected with $R^{12}$, $R^{13}$, $R^{14}$, $R^{15}$ and $R^{16}$:

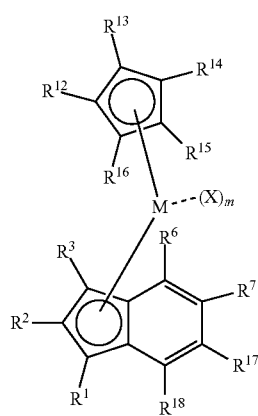

(I)

wherein:
each $R^1$, $R^2$, and $R^3$ is, independently, hydrogen, a substituted or unsubstituted linear, branched linear, or cyclic $C_1$-$C_{20}$, preferably $C_1$-$C_8$, hydrocarbyl group, wherein a first one of $R^1$, $R^2$, and $R^3$ is a substituted or unsubstituted linear, branched linear, or cyclic $C_1$-$C_{20}$, preferably $C_1$-$C_8$, hydrocarbyl group, a second one of $R^1$, $R^2$, and $R^3$ is hydrogen;

and the third one of $R^1$, $R^2$, and $R^3$ is hydrogen, a substituted or unsubstituted linear, branched linear, or cyclic $C_1$-$C_{20}$ hydrocarbyl group;

$R^6$, $R^7$, $R^{17}$, and $R^{18}$ are each independently hydrogen, a substituted or unsubstituted linear, branched linear, or cyclic $C_1$-$C_{30}$ hydrocarbyl group, or $R^6$ and $R^7$, $R^7$ and $R^{17}$, or $R^{17}$ and $R^{18}$, taken together with the carbon atoms in the indenyl ring to which they are directly connected, collectively form one or more substituted or unsubstituted rings annelated to the indenyl ring;

$R^{12}$, $R^{13}$, $R^{14}$ and $R^{15}$ are each independently a substituted or unsubstituted linear, branched linear, or cyclic $C_1$-$C_{20}$ hydrocarbyl group;

$R^{16}$ is a substituted or unsubstituted linear, branched linear, or cyclic $C_1$-$C_{20}$ hydrocarbyl group or silylcarbyl group;

M is a transition metal, preferably a group 4 transition metal, preferably Hf, Ti, or Zr, having an integer coordination number of v, preferably v is 3, 4, or 5;

each X is independently a halogen, a hydride, an amide, an alkoxide, a sulfide, a phosphide, a diene, an amine, a phosphine, an ether, or a $C_1$-$C_{20}$ substituted or unsubstituted linear, branched linear, or cyclic hydrocarbyl group, or optionally two or more X moieties may together form a fused ring or ring system; and m is an integer equal to v-2, preferably m is 1, 2 or 3, preferably 2, preferably M is Zr or Hf, v is 4 and m is 2.

Preferably, in any formula herein, $R^2$ is hydrogen.

In some embodiments, preferred examples of $C_1$-$C_{20}$ and/or $C_1$-$C_{30}$ substituted or unsubstituted linear, branched linear, or cyclic hydrocarbyl groups can include, but are not necessarily limited to: methyl, ethyl, n-propyl, isopropyl, n-butyl, 1-methylpropyl, 1-ethylethyl, n-pentyl, neopentyl (2,2-methylpropyl), 1-methylpentyl, 1-ethylpropyl, 1-hexyl, 1-methylpentyl, 1-ethylbutyl, 1-propylpropyl, optionally substituted cyclohexyl, optionally substituted phenyl, optionally substituted benzyl, and the like, and any ethylenically unsaturated group that can be derived from them by eliminating one available hydrogen group from each of two adjacent carbon atoms therein.

In some embodiments, M comprises, consists essentially of, or is Ti, Zr, and/or Hf. In a preferred embodiment, M comprises, consists essentially of, or is Zr and/or Hf, preferably Hf. In some embodiments, the coordination number of the transition metal M is 4, and thus m is 2.

In some embodiments, each X is independently a halogen or a substituted or unsubstituted linear, branched linear, or cyclic $C_1$-$C_6$ hydrocarbyl group, e.g., a methyl, an ethyl, a propyl, a butyl, a phenyl, a benzyl, a chloride, a bromide, or an iodide, preferably methyl.

Preferably, each $R^1$, $R^2$, and $R^3$ is, independently, hydrogen or a substituted or unsubstituted linear, branched linear, or cyclic $C_1$-$C_6$ hydrocarbyl group (e.g., a methyl, an ethyl, a propyl, a butyl, a cyclohexyl, or a phenyl), preferably subject to the proviso that at least one of $R^1$, $R^2$, and $R^3$ is a substituted or unsubstituted linear, branched linear, or cyclic $C_1$-$C_{20}$, preferably $C_1$-$C_8$, hydrocarbyl group, and two of $R^1$, $R^2$, and $R^3$ are each hydrogen.

In some embodiments, one of $R^1$ and $R^3$ is a beta branched ligand in which a Group 14 atom, e.g., carbon, silicon, germanium, is attached directly to the cyclopentadienyl ring, this same atom further includes at least two non-hydrogen substituents according to the above listing. In other words, the Group 14 atom is tertiary or quaternarily substituted, which includes the bond between the cyclopentadienyl ring and the group 14 atom. Examples include isobutyl, neopentyl, trialkylsilyl, and trialkylgermanyl moieties according to formula (II)

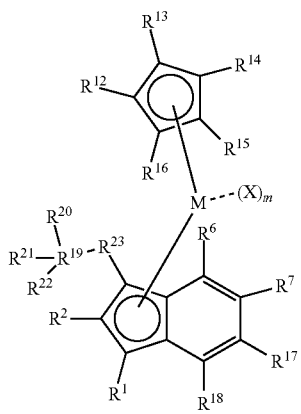

(II)

wherein $R^{23}$ and $R^{19}$ comprise Group 14 atoms, preferably carbon, silicon and/or germanium (preferably $R^{23}$ is C and $R^{19}$ is C or Si), and at least two of $R^{20}$, $R^{21}$, and $R^{22}$ are independently a substituted or unsubstituted linear, branched linear, or cyclic $C_1$-$C_{20}$, preferably $C_1$-$C_8$, hydrocarbyl group.

In some embodiments, one of $R^1$, $R^2$, and $R^3$ is a substituted or unsubstituted linear, branched linear, or cyclic $C_1$-$C_6$ hydrocarbyl group (e.g., a methyl, an ethyl, a propyl, a butyl, a pentyl, a neopentyl, an isoamyl, a cyclohexyl, or a phenyl, such as methyl), preferably a methyl or a neopentyl, and the remaining two of $R^1$, $R^2$, and $R^3$ are each hydrogen.

In some embodiments, $R^6$, $R^7$, $R^{17}$, and $R^{18}$ are each independently hydrogen, a substituted or unsubstituted linear, branched linear, or cyclic $C_1$-$C_{30}$ hydrocarbyl group. In some embodiments $R^6$, $R^7$, $R^{17}$, and $R^{18}$ are each independently hydrogen, a substituted or unsubstituted linear, branched linear, or cyclic $C_1$-$C_{30}$ hydrocarbyl group in which two of $R^6$, $R^7$, $R^{17}$, and $R^{18}$ taken together with the carbon atoms in the indenyl ring to which they are directly connected, collectively form one or more substituted or unsubstituted rings annelated to the indenyl ring. The rings are indicated by the dotted lines between the respective R group substitutions with a ring between $R^6$ and $R^7$ indicated as Ring 6-7, a ring between $R^7$ and $R^{17}$ indicated as Ring 7-17 and a ring between $R^{17}$ and $R^{18}$ indicated as Ring 17-18 as shown in the general formula (III-A) below:

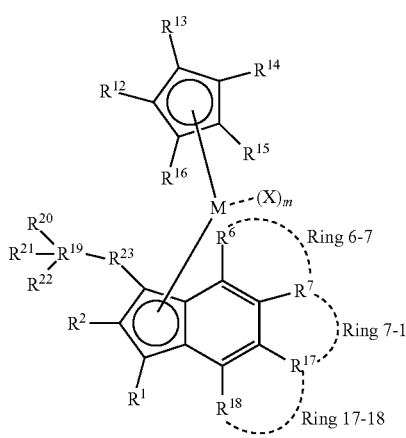

(III-A)

In some embodiments, $R^6$ and $R^7$ taken together with the carbon atoms in the indenyl ring to which they are directly connected, collectively form Ring 6-7 comprising a $C_3$-$C_6$ ring, preferably an alicyclic ring, preferably a 5 membered ring including two the carbons of the indenyl ring. In such embodiments, the 3 alicyclic ring carbons not directly part of the indenyl ring are each independently bonded to a hydrogen or a substituted or unsubstituted linear, branched linear, or cyclic $C_1$-$C_6$ hydrocarbyl group (e.g., a methyl, an ethyl, a propyl, a butyl, a cyclohexyl, or a phenyl). In some embodiments, at least two or all three of the alicyclic ring carbons are connected to a hydrogen, one of $R^1$ is a substituted or unsubstituted linear, branched linear, or cyclic $C_1$-$C_6$ hydrocarbyl group (e.g., a methyl, an ethyl, a propyl, a butyl, a pentyl, an isoamyl, a neopentyl, a cyclohexyl, or a phenyl), and $R^2$ is hydrogen.

Preferably, at least one of $R^{20}$, $R^{21}$, and $R^{22}$ are $C_1$-$C_6$ hydrocarbyl group (e.g., a methyl, an ethyl, a propyl, a butyl, a pentyl, an isoamyl, a neopentyl, a cyclohexyl, or a phenyl), such that $R^3$ is a beta-branched moiety. In some embodiments, $R^{23}$ and $R^{19}$ are carbon, silicon or germanium, and $R^{20}$, $R^{21}$, and $R^{22}$ are each a $C_1$-$C_6$ hydrocarbyl group; preferably $R^{23}$ is a methylene group (—$CH_2$—) and $R^{19}$, $R^{20}$, $R^{21}$ and $R^{22}$ form a trimethylsilyl, triethylsilyl, or terphenylsilyl moiety. Preferably in any of the above embodiments, $R^{12}$, $R^{13}$, $R^{14}$, $R^{15}$, $R^{16}$, $R^{17}$, and $R^{18}$ are each independently a hydrogen, or a substituted or unsubstituted linear, or branched $C_1$-$C_6$, hydrocarbyl group. Preferably $R^7$ and $R^{17}$ taken together with the carbon atoms in the indenyl ring to which they are directly connected, collectively form Ring 7-17 comprising three additional carbons to form a 5 membered alicyclic ring; $R^1$, $R^{12}$, $R^{13}$, $R^{14}$, $R^{15}$ and $R^{16}$ are methyl radicals, $R^2$, $R^3$, $R^6$, and $R^{18}$, are hydrogen. In such embodiments, the metallocene compound can have a structure represented by formula (IV-B) below:

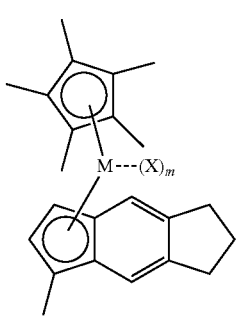

(IV-B)

In some embodiments $R^{17}$ and $R^{18}$ taken together with the carbon atoms in the indenyl ring to which they are directly connected, collectively form one or more substituted or unsubstituted $C_3$-$C_6$ rings annelated to the indenyl ring; and $R^6$, $R^7$, $R^{12}$, $R^{13}$, $R^{14}$, $R^{15}$ and $R^{16}$ are each independently a hydrogen, or a substituted or unsubstituted linear, or branched $C_1$-$C_6$, hydrocarbyl group. Preferably $R^{17}$ and $R^{18}$ taken together with the carbon atoms in the indenyl ring to which they are directly connected, collectively form a six membered phenyl ring, Ring 17-18 comprising four additional carbons. In such embodiments, the four phenyl ring carbons not directly part of the indenyl ring (the carbons attached to $R^8$, $R^9$, $R^{10}$, and $R^{11}$ in formula (III) below) are each independently bonded to a hydrogen or a substituted or unsubstituted linear, branched linear, or cyclic $C_1$-$C_6$ hydrocarbyl group (e.g., a methyl, an ethyl, a propyl, a butyl, a cyclohexyl, or a phenyl). In such embodiments, at least two of, or at least three of, or all four of $R^8$, $R^9$, $R^{10}$, and $R^{11}$ are hydrogen. Stated another way, $R^{17}$ and $R^{18}$ taken together with the carbon atoms in the first cyclopentadienyl ring to which they are directly connected, collectively form a substituted or unsubstituted naphthenyl ring annelated to the first cyclopentadienyl ring. In such embodiments, the metallocene compound can have a structure represented by formula (III) below:

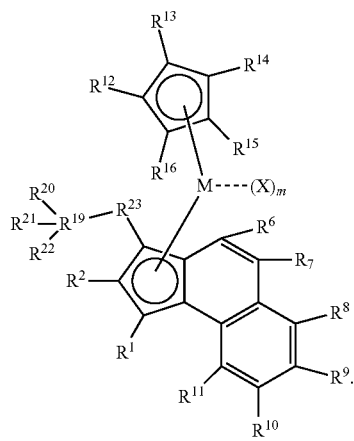

(III)

Preferably in such an embodiment, one of $R^1$ and $R^{23}$ are a substituted or unsubstituted linear, branched linear, or cyclic $C_1$-$C_6$ hydrocarbyl group (e.g., a methyl, an ethyl, a propyl, a butyl, a pentyl, an isoamyl, a neopentyl, a cyclohexyl, or a phenyl), $R^2$ and R1 are hydrogen. Preferably in such an embodiment, $R^{23}$ and $R^{19-22}$ form a neopentyl (i.e., 2,2-dimethylpropyl), $R^1$, $R^2$, $R^6$, $R^7$, $R^8$, $R^9$, $R^{10}$, and $R^{11}$ are each hydrogen, and $R^{12}$, $R^{13}$, $R^4$, $R^{15}$, $R^{16}$ are methyl; the metallocene compound can have a structure represented by formula (III-B) below:

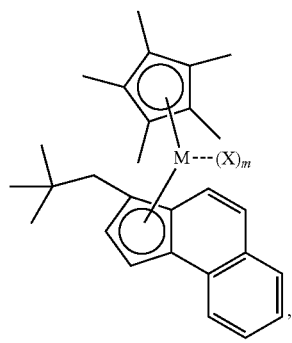

(III-B)

where M is Hf or Zr and M is 2.

Preferably, $R^{23}$, $R^{19-22}$ form a methyl-trimethylsilyl, methyl-triethylsilyl, or methyl-triphenylsilyl moiety, $R^6$, $R^7$, $R^{17}$, and $R^{18}$, are each hydrogen, and or a substituted or unsubstituted linear, or branched $C_1$-$C_6$, hydrocarbyl group. Preferably in such embodiments $R^6$, $R^7$, $R^{17}$, and $R^{18}$ are hydrogen, and $R^{12}$, $R^{13}$, $R^{14}$, R, $R^{16}$ are methyl; having a structure represented by formula (III-SI) below.

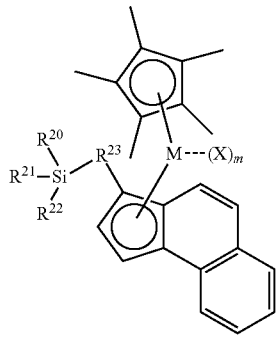

(III-SI)

wherein $R^{23}$, $R^{20}$, and $R^{21}$ are substituted or unsubstituted linear, branched linear, or cyclic $C_1$-$C_6$ hydrocarbyl group, preferably methyl, ethyl, or phenyl, more preferably each of $R^{23}$, $R^{20}$, and $R^{21}$ are methyl.

It is noted, in the embodiments listed above, $R^1$ and $R^3$ may be interchangeable. Reference to either of $R^1$ and $R^3$ are maintained for consistency and clarity herein. In any of the above embodiments, M preferably comprises, consists essentially of, or is Zr and/or Hf; m is 2; and each X is independently a methyl, an ethyl, a propyl, a butyl, a hexyl, an octyl, a phenyl, a benzyl, a chloride, a bromide, or an iodide.

Particularly desirable metallocene compounds useful for the process of the present invention include the following compounds and their optical isomers, if applicable (not shown):

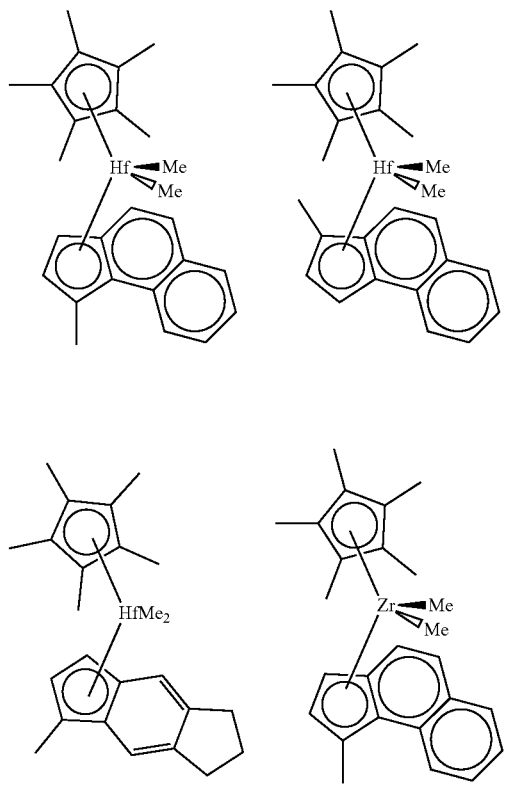

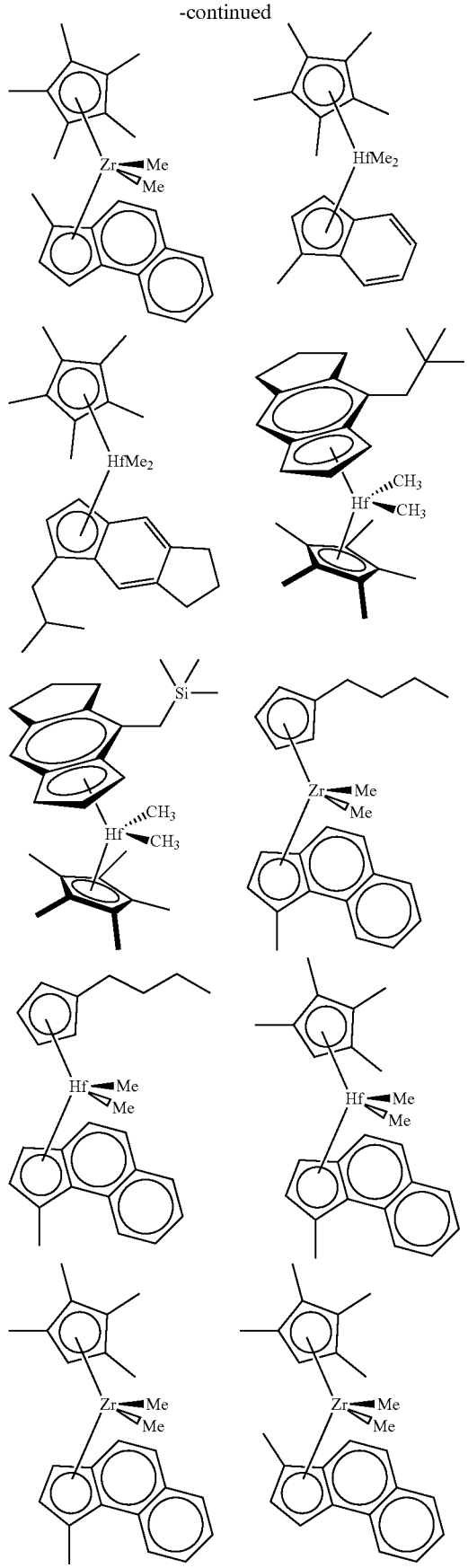
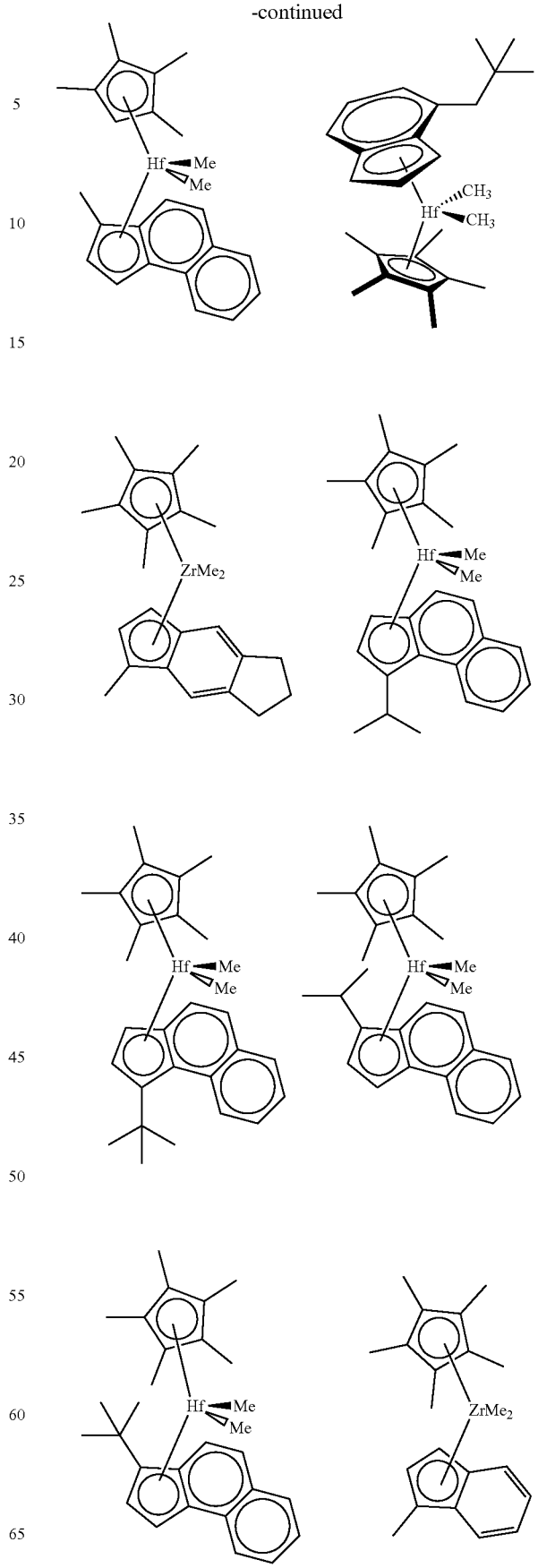

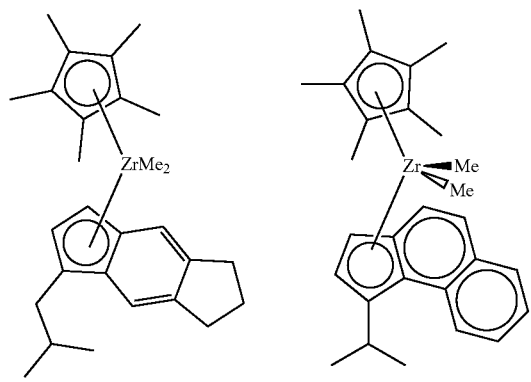
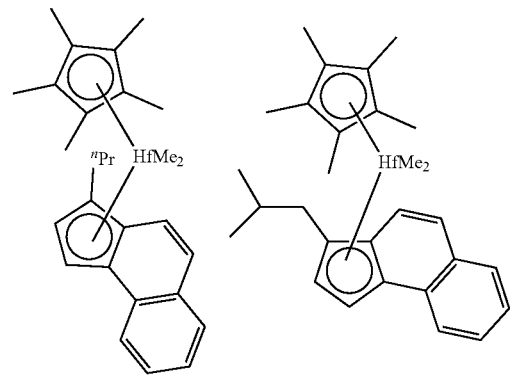
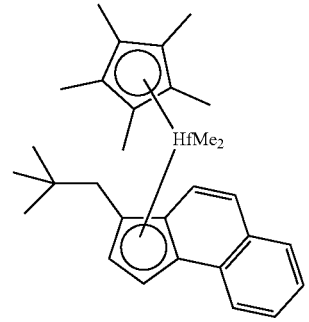
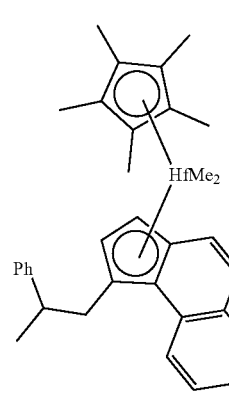
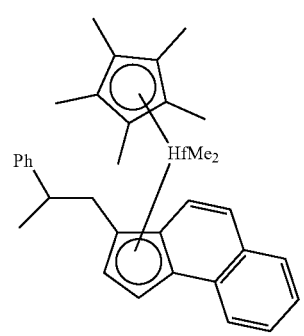

-continued

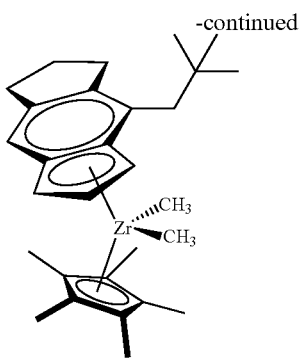

Metallocene compounds generally can be synthesized by using typical chemical reagents (e.g., halides of hafnium, zirconium, titanium) and intermediates (such as ligands containing one or two substituted or unsubstituted Cp rings, substituted or unsubstituted annelated Cp ring such as indenyl rings or benzindenyl rings, and the like) that are commercially available, and following typical reaction schemes exemplified in various synthesis descriptions, e.g., as described in the example sections of U.S. Provisional Application Nos. 62/477,683 and 62/477,706, both filed Mar. 28, 2017, the contents of each of which are hereby incorporated by reference.

III.2 Activators and Activation of the Metallocene Compound

An additional component of a catalyst system described herein may be an activator. The metallocene compounds, when activated by a commonly known activator such as non-coordinating anion activator, form active catalysts for the polymerization or oligomerization of olefins. Activators that may be used include Lewis acid activators such as triphenylboron, tris-perfluorophenylboron, tris-perfluorophenylaluminum and the like and or ionic activators such as N,N-dimethylanilinium tetrakis(perfluorophenyl)borate, N,N-dimethylanilinium tetrakis(perfluoronaphthyl)borate, triphenylcarbonium tetrakis(perfluorophenyl)borate, triphenylcarbonium tetrakis(perfluoronaphthyl)borate, N,N-dimethylanilinium tetrakis(perfluorophenyl)aluminate, N,N-dimethylanilinium tetrakis(perfluoronaphthyl)aluminate, and the like.

A co-activator is a compound capable of alkylating the transition metal complex, such that when used in combination with an activator, an active catalyst is formed. Co-activators can include alumoxanes such as methylalumoxane, modified alumoxanes such as modified methylalumoxane, and aluminum alkyls such trimethylaluminum, tri-isobutylaluminum, triethylaluminum, and tri-isopropylaluminum, tri-n-hexylaluminum, tri-n-octylaluminum, tri-n-decylaluminum or tri-n-dodecylaluminum. Co-activators are typically used in combination with Lewis acid activators and ionic activators when the pre-catalyst is not a dihydrocarbyl or dihydride complex. Sometimes co-activators are also used as scavengers to deactivate impurities in feed or reactors.

U.S. Pat. No. 9,409,834 (e.g., at line 39, column 21 to line 44, column 26) provides a detailed description of the activators and coactivators that may be used with the metallocene compound in the catalyst system of the present invention. The relevant portions of this patent are incorporated herein by reference in their entirety.

Additional information of activators and co-activators that may be used with the metallocene compounds in the catalyst system of the present invention can be found in U.S. Patent Application Publication No. 2013/0023633 (e.g., at paragraph [0178] page 16 to paragraph [0214], page 22). The relevant portions of this reference are incorporated herein by reference in their entirety.

III.3 Scavenger

A scavenger can be an additional component of a catalyst system described herein. A scavenger is a compound typically added to facilitate oligomerization or polymerization by scavenging impurities. Some scavengers may also act as activators and may be referred to as co-activators. A co-activator which is not a scavenger may also be used in conjunction with an activator in order to form an active catalyst with a transition metal compound. In some embodiments, a co-activator can be pre-mixed with the transition metal compound to form an alkylated transition metal compound, also referred to as an alkylated catalyst compound or alkylated metallocene. To the extent scavengers facilitate the metallocene compound in performing the intended catalytic function, scavengers, if used, are sometimes considered as a part of the catalyst system.

U.S. Pat. No. 9,409,834 (e.g., at line 37, column 33 to line 61, column 34) provides detailed description of scavengers useful in the process of the present invention for making PAO. The relevant portions in this patent on scavengers, their identities, quantity, and manner of use are incorporated herein in their entirety.

IV. Process for Making PAO

The process for making a PAO of the present invention includes a step of contacting a feed comprising a $C_6$-$C_{32}$ alpha-olefin (preferably $C_6$-$C_{30}$, particularly $C_6$-$C_{24}$, $C_6$-$C_{18}$, $C_8$-$C_{18}$, or $C_6$-$C_{12}$) with a catalyst system comprising a metallocene compound described above in a polymerization reactor under polymerization conditions to effect a polymerization reaction to obtain a polymerization reaction mixture comprising vinylidenes, tri-substituted vinylenes, optionally di-substituted vinylenes, and optionally vinyls; and obtaining an unsaturated PAO product from the polymerization reaction mixture, wherein the unsaturated PAO product comprises vinylidenes, tri-substituted vinylenes, optionally di-substituted vinylenes, and optionally vinyls.

IV.1 Monomer(s)

The alpha-olefin feed for making the PAO materials of the present invention may comprise one or more of $C_6$-$C_{32}$ alpha-olefins (preferably $C_6$-$C_{24}$, particularly $C_6$-$C_{18}$, $C_8$-$C_{18}$, or $C_6$-$C_{12}$). Thus, the feed may comprise ethylene, propylene, $C_4$ alpha-olefins, and $C_5$ alpha-olefins. In certain embodiments, each of ethylene, propylene, $C_4$ alpha-olefins (1-butene and 2-methyl-1-propene), and $C_5$ alpha-olefins (1-pentene and various isomers of methyl-1-butene) is supplied to the polymerization reactor, each independently at no higher than c1 mol %, based on the total moles of the alpha-olefins supplied to the polymerization reactor, where c1 can be 25, 20, 10, 5, 4, 3, 2, 1, 0.5, 0.1, or 0.01, for each monomer; additionally or alternatively, any combination of $C_2$-$C_5$ alpha-olefins (including two or more, three or more, or all four of ethylene, propylene, $C_4$ alpha-olefins, and $C_5$ alpha-olefins) are supplied to the polymerization reactor collectively at no higher than c1 mol %, based on the total moles of the alpha-olefins supplied to the polymerization reactor. Preferably, the alpha-olefin feed is substantially free of ethylene, propylene, $C_4$ alpha-olefins, and $C_5$ alpha-olefins (or completely free of intentionally added $C_2$-$C_5$ alpha-olefins, allowing for impurities present in other feed components). In preferable embodiments, substantially all alpha-olefins in the feed are $C_6$-$C_{30}$ (e.g., $C_6$-$C_{24}$, particularly $C_6$-$C_{18}$, $C_8$-$C_{18}$, or $C_6$-$C_{12}$) alpha-olefins. "Substantially all" means at least 90 mol % (e.g., at least 92 mol %, at least 94 mol %, at least 95 mol %, at least 96 mol %, at least 98 mol %, at least 99%, at least 99.5 mol %, or completely all, allowing for some impurities present in feed components), based on the total moles of the alpha-olefins present in the feed. Preferably, any combination of $C_2$-$C_5$ alpha-olefins are collectively present in the alpha-olefin feed at no higher than c1 mol %, (where c1 can be 25, 20, 10, 5, 4, 3, 2, 1, 0.5, 0.1, or 0.01) based on the total moles of the alpha-olefins supplied to the polymerization reactor.

In some preferred embodiments, at least a portion (e.g., at least 80 mol %, at least 85 mol %, at least 90 mol %, at least 95 mol %, at least 96 mol %, at least 98 mol %, at least 99%, at least 99.5 mol %, or completely all, allowing for some impurities present in feed components) of the alpha-olefins present in the feed are linear alpha-olefins (LAOs), i.e., those without a branch attached to the carbon backbone thereof. Non-limiting examples of LAOs are 1-butene, 1-pentene, 1-hexene, 1-heptene, 1-octene, 1-nonene, 1-decene, 1-dodecene, 1-tetradecene, 1-hexadecene, 1-octadecene, 1-icocene, $C_{22}$, $C_{24}$, $C_{26}$, $C_{28}$, $C_{30}$ and $C_{32}$ LAOs. Without being bound by theory, PAO products made from such LAOs by using the process of the present invention can tend to have fewer branches and pendant groups, leading to generally more uniform PAO molecular structures, and hence typically better performance for applications such as lubricant base stocks, lubricant additives, and the like.

Where a single alpha-olefin is fed to the polymerization reactor, the thus obtained PAO is a homopolymer. Homopolymers can have substantially uniform molecular structure, and accordingly desirable physical and rheological properties such as viscosity index. A homopolymer can tend to have pendant groups attached to the carbon backbone with highly uniform length.

In certain situations, a mixture of two, three, or even more alpha-olefins in the feed may be desired to produce a copolymer PAO product. To that end, alpha-olefins with the following combinations can be particularly advantageous: $C_6/C_8$, $C_6/C_{10}$, $C_6/C_{12}$, $C_6/C_{14}$, $C_6/C_{16}$, $C_8/C_{10}$, $C_8/C_{12}$, $C_8/C_{14}$, $C_8/C_{16}$, $C_{10}/C_{12}$, $C_{10}/C_{14}$, $C_{10}/C_{16}$, $C_{10}/C_{18}$, $C_{12}/C_{14}$, $C_{12}/C_{16}$, $C_{12}/C_{18}$, $C_{12}/C_{20}$, $C_6/C_8/C_{10}$, $C_6/C_8/C_{12}$, $C_6/C_8/C_{14}$, $C_6/C_{10}/C_{12}$, $C_6/C_{10}/C_{14}$, $C_8/C_{10}/C_{12}$, $C_8/C_{10}/C_{14}$, $C_8/C_{12}/C_{14}$, $C_{10}/C_{12}/C_{16}$, $C_{10}/C_{12}/C_{18}$, $C_{10}/C_{14}/C_{16}$, $C_{10}/C_{14}/C_{18}$, and the like. Desirably, at least one of the alpha-olefins in the mixture feed can be an LAO. In particular, substantially all of the alpha-olefins in the mixture feed can be LAOs.

Preferred alpha-olefin monomers are mono-olefins containing one C=C bond per monomer molecule, though those olefins containing two or more C=C bonds per monomer molecule can be used as well.

Preferred monomers useful herein include substituted or unsubstituted $C_6$ to $C_{32}$ alpha olefins, or $C_6$ to $C_{20}$ alpha olefins, or $C_6$ to $C_{14}$ alpha olefins, or hexene, heptene, octene, nonene, decene, undecene, dodecene, tetradecene and isomers thereof. Preferably, the polyalphaolefin prepared herein comprises 50 mol % or more (preferably 60 mol % or more, preferably 70 mol % or more, preferably 80 mol % or more, preferably 90 mol % or more, preferably 99 mol % or more) of one or more $C_6$ to $C_{32}$ (preferably $C_6$ to $C_{20}$, preferably $C_8$ to $C_{18}$) alpha-olefin monomers.

Useful $C_6$ to $C_{32}$ alpha-olefin monomers include hexene, heptene, octene, nonene, decene, undecene, dodecene, tetradecene, substituted derivatives thereof, and isomers thereof.

Preferably, the monomers comprise $C_6$ to $C_{20}$ alpha-olefins, or $C_6$ to $C_{14}$ alpha-olefins, and/or $C_8$ to $C_{12}$ alpha-olefins.

Preferred olefin monomers include one (alternately two, alternately three) or more of hexene, heptene, octene, nonene, decene, dodecene, and tetradecene.

In an embodiment the PAO is a homopolymer of any $C_8$ to $C_{12}$ alpha-olefin, i.e., the PAO is a homopolymer of 1-hexene, 1-heptene, 1-octene, 1-nonene, 1-decene, 1-undecene, 1-dodecene or 1-tetradecene. Preferably, the PAO is a homopolymer of decene. In another embodiment the PAO is a copolymer comprising decene and one or more of any of the monomers listed above.

In an embodiment, the PAO comprises two or more monomers, or three or more monomers, or four or more monomers, or five or more monomers. For example, a $C_8$, $C_{10}$, $C_{12}$-linear alpha-olefin mixture, or a $C_6$, $C_7$, $C_8$, $C_9$, $C_{10}$, $C_{11}$, $C_{12}$, $C_{13}$, $C_{14}$-linear alpha-olefin mixture, or a $C_6$, $C_8$, $C_{10}$, $C_{12}$, $C_{14}$, $C_{16}$, $C_{18}$-linear alpha-olefin mixture can be used as a feed.

In an alternate embodiment, the PAO comprises less than 50 mol % of $C_2$, $C_3$, and $C_4$ monomers, or less than 40 mol %, or less than 30 mol %, or less than 20 mol %, or less than 10 mol %, or less than 5 mol %, or less than 3 mol %, or 0 mol %. Specifically, in an alternate embodiment, the PAO comprises less than 50 mol % of ethylene, propylene and butene, or less than 40 mol %, or less than 30 mol %, or less than 20 mol %, or less than 10 mol %, or less than 5 mol %, or less than 3 mol %, or 0 mol %. In another embodiment, the PAO comprises less than 40 mol %, or less than 20 mol %, or less than 10 mol %, or less than 5 mol %, or less than 3 mol %, or 0 mol % of ethylene.

In an alternate embodiment, the PAO comprises less than 25 mol % of $C_2$, $C_3$, and $C_4$ monomers, or less than 20 mol %, or less than 15 mol %, or less than 10 mol %, or less than 5 mol %, or less than 1 mol %, or 0 mol %. Specifically, in an alternate embodiment, the PAO comprises less than 25 mol % of ethylene, propylene and butene, or less than 20 mol %, or less than 15 mol %, or less than 10 mol %, or less than 5 mol %, or less than 1 mol %, or 0 mol %. In another embodiment, the PAO comprises less than 25 mol %, or less than 20 mol %, or less than 10 mol %, or less than 5 mol %, or less than 1 mol %, or 0 mol % of ethylene.

In another embodiment, the PAO comprises less than 40 mol % of propylene. In another embodiment, the PAO comprises less than 40 mol % of butene. In another embodiment, the PAO comprises less than 10 mol % of ethylene. In another embodiment, the PAO comprises less than 10 mol % of propylene. In another embodiment, the PAO comprises less than 10 mol % of butene.

In another embodiment, the PAO comprises less than 25 mol % of propylene. In another embodiment, the PAO comprises less than 25 mol % of butene. In another embodiment, the PAO comprises less than 5 mol % of ethylene. In another embodiment, the PAO comprises less than 5 mol % of propylene. In another embodiment, the PAO comprises less than 5 mol % of butene. In another embodiment, the PAO comprises less than 1 mol % of ethylene. In another embodiment, the PAO comprises less than 1 mol % of propylene. In another embodiment, the PAO comprises less than 1 mol % of butene.

The alpha-olefins used herein can be produced directly from ethylene growth process as practiced by several commercial production processes, or they can be produced from Fischer-Tropsch hydrocarbon synthesis from $CO/H_2$ syngas, or from metathesis of internal olefins with ethylene, or from cracking of petroleum or Fischer-Tropsch synthetic wax at high temperature, or any other alpha-olefin synthesis routes. An exemplary feed for this invention can be at least 80 wt % alpha-olefin (preferably linear alpha olefin), preferably at least 90 wt % alpha-olefin (preferably linear alpha olefin), or approximately 100% alpha-olefin (preferably linear alpha olefin). However, alpha-olefin mixtures can also be used as feeds in this invention, especially if the other components are internal-olefins, branched olefins, paraffins, cyclic paraffins, aromatics (such as toluene and or xylenes). These components may have diluent effects and are believed to not have a substantial detrimental effect on the polymerization of alpha-olefins. In other words, the process described herein can selectively convert alpha-olefins in a mixture and leave the other components largely, if not completely, unreacted. This can be particularly useful when ethylene is not present in the mixture. This technology can be used to separate out alpha-olefins from a mixture by selectively reacting them with polymerization or oligomerization catalyst systems, effectively if not completely eliminating the need to separate alpha-olefins from the remainder of the components in a mixed feed stream. This can be economically advantageous, for example, in a process utilizing Fisher-Tropsch synthesis olefin product streams containing alpha-olefins, internal-olefins and branched olefins. Such a mixture can be fed to oligomerization technology as described herein and to selectively react away the alpha-olefin. No separate step to isolate the alpha-olefin may be needed. Another example of the utility of this process involves alpha-olefins produced by the metathesis of internal olefins with ethylene, which may contain some internal olefins. This mixed olefin base stock feed can be reacted as-is in the polymerization/oligomerization process of the present invention, which selectively converts the alpha-olefins into lube products. Thus, one can use the alpha-olefin for the base stock synthesis without having to separate the alpha-olefin from internal olefin. This can bring a significant improvement in process economics. The feed olefins can be the mixture of olefins produced from other linear alpha-olefin process containing $C_4$ to $C_{20}$ alpha-olefins as described in Chapter 3 "Routes to Alpha-Olefins" of the book Alpha Olefins Applications Handbook, Edited by G. R. Lappin and J. D. Sauer, published by Marcel Dekker, Inc. N.Y. 1989.

IV.2 Feed Purification

Olefin feed and or solvents may be treated to remove catalyst poisons, such as peroxides, oxygen, or nitrogen-containing organic compounds or acetylenic compounds before being supplied to the polymerization reactor. For example, the treatment of the linear alpha-olefin with an activated 13A molecular sieve and a de-oxygenate catalyst (i.e., a reduced copper catalyst) can increase catalyst productivity (expressed in terms of quantity of PAO produced per micromole of the metallocene compound used) more than 10-fold. Alternatively, the feed olefins and or solvents may be treated with an activated molecular sieve, such as 3 Å, 4 Å, 8 Å, or 13 Å molecular sieve, and/or in combination with an activated alumina or an activated de-oxygenate catalyst. Such treatment can desirably increase catalyst productivity 2- to 10-fold or more.

IV.3 Polymerization Reaction

Many polymerization/oligomerization processes and reactor types used for metallocene-catalyzed polymerization or oligomerization such as solution, slurry, and bulk polymerization or oligomerization processed can be used in this invention. If a solid or supported catalyst is used, a slurry or continuous fixed bed or plug flow process may be suitable. Preferably, the monomers are contacted with the metallocene compound and the activator in the solution phase, bulk phase, or slurry phase, for example in a continuous stirred tank reactor or a continuous tubular reactor. In some embodiments, the temperature in any reactor used herein can be from −10° C. to 250° C., e.g., from 30° C. to 220° C., preferably from 50° C. to 180° C., from 60° C. to 170° C., or from 70° C. to 150° C. In some embodiments, the pressure in any reactor used herein can be from 0.1 to 100 atmospheres, e.g., from 0.5 to 75 atmospheres or from 1 to 50 atmospheres. Alternatively, the pressure is any reactor used herein can be from 1 to 50,000 atmospheres, e.g., from 1 to 25,000 atmospheres. Additionally or alternatively, the monomer(s), metallocene and activator can be contacted for a residence time of 1 second to 100 h, e.g., 30 seconds to 50 h, 2 minutes to 6 h, or 1 minute to 4 h. Additionally or alternatively, solvent or diluent may be present in the reactor and may include butanes, pentanes, hexanes, heptanes, octanes, nonanes, decanes, undecanes, dodecanes, tridecanes, tetradecanes, pentadecanes, hexadecanes, toluene, o-xylene, m-xylene, p-xylene, mixed xylenes, ethylbenzene, propylbenzenes such as isopropylbenzene, butylbenzenes such as n-butylbenzene or t-butylbenzene, cumene, or a combination thereof, preferable solvents can include toluene, xylenes, ethylbenzene, normal paraffins (such as NORPAR® solvents available from ExxonMobil Chemical Company in Houston, Tex.), isoparaffin solvents (such as ISOPAR® solvents available from ExxonMobil Chemical Company in Houston, Tex.), and combinations thereof. These solvents or diluents may typically be pre-treated in same manners as the feed olefins.

Regardless of the type of reactor or process, it is typically desirable that the average activity level of the catalyst system be maintained at or above a sufficiently high level, so as to attain a minimum reasonable yield of oligomeric product, relative to monomeric reactant(s). For example, in some embodiments, the catalytic reaction can have an average activity level of at least 800 g/s·mol, e.g., at least 900 g/s·mol, at least 1000 g/s·mol, at least 1100 g/s·mol, at least 1200 g/s·mol, at least 1300 g/s·mol, at least 1400 g/s·mol, at least 1500 g/s·mol, at least 1700 g/s·mol, at least 1900 g/s·mol, at least 2100 g/s·mol, at least 2500 g/s·mol, or at least 2800 g/s·mol; although average activity levels are not often characterized as being "too high," it is theoretically possible for the average activity level to be so high that control of the reaction product may be difficult to achieve in practice, such that the average catalytic reaction activity level can optionally be less than 1000 kg/s·mol, e.g., less than 500 kg/s·mol, in some embodiments. Additionally or alternatively, in some embodiments, the catalytic reaction can provide a minimum reasonable yield (grams of oligomer per grams of monomer feed) of at least 18%, e.g., at least 19%, at least 20%, at least 22%, at least 24%, at least 27%, at least 30%, at least 33%, at least 36%, at least 38%, or at least 40%, based on a reaction time of ~1 h (~3600 s); although reasonable catalytic yield is not often characterized as being "too high," with a maximum of approximately 100% in a 1-h reaction time, it is theoretically possible for relatively high yields, particularly high yields in relatively short reaction times, to detrimentally affect the ability to control the reaction product, e.g., such that a maximum reasonable yield may optionally be approximately 100% in a reaction time of ~1 minute or less, e.g., approximately 100% in a reaction time of ~10 minutes or less, approximately 100% in a reaction time of ~30 minutes or less, approximately 100% in a reaction time of ~1 h or less, approximately 95% in a reaction time of ~1 h or less, or approximately 90% in a reaction time of ~1 h or less.

In some embodiments, it can be desirable to attain both relatively low product molecular weight and relatively high product vinylidene content. However, in many metallocene reactions where a vinylidene bond is a significant unsaturation product (at least 30 mol %, relative to the total number of moles of vinyls, vinylidenes, di-substituted vinylenes, and tri-substituted vinylenes), increasing reaction temperature can cause a decrease (or at least no increase) in both molecular weight and vinylidene content. Because reaction temperature can be one of the most ubiquitous ways to control product characterization parameters for a given catalyst system, it can often be a challenge to attain a product having both relatively low molecular weight and relatively high vinylidene content in many conventional systems. Thus, in some preferred embodiments of the invention, the combination of the reaction/polymerization/oligomerization conditions with certain metallocene catalyst systems can advantageously result in both decreasing molecular weight and increasing vinylidene content with increasing reaction temperature, thereby allowing heightened control of desired parameters without having to sacrifice one too much to attain the other. In such preferred embodiments, e.g., by carefully selecting the elements of the metallocene catalyst system, the average activity level of the catalyst system be can be further advantageously maintained at or above a sufficiently high level, so as to attain a minimum reasonable yield of oligomeric product, relative to monomeric reactant(s).

Typically, one or more metallocene compounds, one or more activators, and one or more monomers are contacted to produce polymer or oligomer. These catalysts may be supported and, as such, may be particularly useful in the known slurry, solution, or bulk operating modes conducted in single, series, or parallel reactors. If the catalyst, activator, or co-activator is a soluble compound, the reaction can be carried out in a solution mode. Even if one of the components is not completely soluble in the reaction medium or in the feed solution, either at the beginning of the reaction or during or at later stages of the reaction, a solution or slurry type operation may still be applicable. In any instance, the catalyst system components, dissolved or suspended insolvents, such as toluene or other conveniently available aromatic solvents, or in aliphatic solvent, or in the feed alpha-olefin stream, can be fed into the reactor under inert atmosphere (usually nitrogen or argon blanketed atmosphere) to allow the polymerization or oligomerization to take place.

The polymerization or oligomerization can be run in a batch mode, where all the components are added into a reactor and allowed to react to a pre-designed degree of conversion, either to partial conversion or full conversion. Subsequently, the catalyst can be deactivated by any possible means, such as exposure to air or water, or by addition of alcohols or solvents containing deactivating agents.

The polymerization or oligomerization can additionally or alternatively be carried out in a semi-continuous operation, where feeds and catalyst system components can be continuously and/or simultaneously added to the reactor so as to maintain a constant ratio of catalyst system components to feed olefin(s). When all feeds and catalyst system components are added, the reaction may be allowed to proceed to a pre-determined stage. The reaction can then be discontinued by catalyst deactivation in the same manner as described for batch operation.

The polymerization or oligomerization can additionally or alternatively be carried out in a continuous operation, where feeds and catalyst system components can be continuously and/or simultaneously added to the reactor so to maintain a constant ratio of catalyst system and feed olefins. The reaction product can be continuously withdrawn from the reactor, as in a typical continuous stirred tank reactor (CSTR) operation. The residence times of the reactants can be controlled by a pre-determined degree of conversion. The withdrawn product can then typically be quenched in the separate reactor in a similar manner as other operation. In some embodiments, any of the processes to prepare PAOs described herein are continuous processes, which can include the steps of a) continuously introducing a feed stream comprising at least 10 mol % of the one or more $C_6$ to $C_{24}$ alpha-olefins into a reactor, b) continuously introducing the metallocene compound and the activator into the reactor, and c) continuously withdrawing the PAO from the reactor. Additionally or alternatively, the continuous process can include the step of maintaining a partial pressure of hydrogen in the reactor of 200 psig (~1.4 MPag) or less, based upon the total pressure of the reactor, e.g., 150 psig (~1.0 MPag) or less, 100 psig (~690 kPag) or less, 50 psig (~350 kPag) or less, 25 psig (~170 kPag) or less, or 10 psig (~69 kPag) or less. Additionally or alternatively the hydrogen, if present in the reactor, in the feed, or in both, at a concentration of 1000 ppm or less by weight, e.g., 750 wppm or less, 500 wppm or less, 250 wppm or less, 100 wppm or less, 50 wppm or less, 25 wppm or less, 10 wppm or less, or 5 wppm or less.

Preferred reactors can range in size from 2 mL and up. Usually, it is preferable to use reactors larger than one liter in volume for commercial production. The production facility may have one single reactor, or several reactors, arranged in series or in parallel or in both to maximize productivity, product properties, and general process efficiency. The reactors and associated equipment are usually pre-treated to ensure proper reaction rates and catalyst performance. The reaction is usually conducted under inert atmosphere, where the catalyst system and feed components may be out of contact with any catalyst deactivator or poison, e.g., polar oxygen, nitrogen, sulfur, and/or acetylenic compounds.

One or more reactors in series or in parallel may be used in the present invention. The metallocene compound, activator and when required, co-activator, may be delivered as a solution or slurry in a solvent or in the alpha-olefin feed stream, either separately to the reactor, activated in-line just prior to the reactor, or pre-activated and pumped as an activated solution or slurry to the reactor. Polymerizations/oligomerization can be carried out in either single reactor operation, in which monomer, or several monomers, catalyst/activator/co-activator, optional scavenger, and optional modifiers may be added continuously to a single reactor or in series reactor operation, in which the above components can be added to each of two or more reactors connected in series. The catalyst system components can be added to the first reactor in the series. The catalyst system component may alternatively be added to both reactors, with one component being added to first reaction and another component to other reactors. In some embodiments, the metallocene compound can be activated in the reactor in the presence of olefin. Alternatively, the metallocene compound (such as a dichloride form of the metallocene compound) may be pre-treated with an alkylaluminum reagent, especially triisobutylaluminum, tri-n-hexylaluminum, and/or tri-n-octylaluminum, followed by charging into the reactor containing other catalyst system component and the feed olefins, or followed by pre-activation with the other catalyst system component to give the fully activated catalyst, which can then be fed into the reactor containing feed olefins. In another alternative, the pre-catalyst metallocene can be mixed with the activator and/or the co-activator, and this activated catalyst can then be charged into reactor, together with feed olefin stream containing some scavenger or co-activator. In another alternative, the whole or part of the co-activator can be pre-mixed with the feed olefins and charged into the reactor at the same time as the other catalyst solution containing metallocene and activators and/or co-activator.

The catalyst compositions can be used individually or can be mixed with other known polymerization catalysts to prepare polymer or oligomer blends. Monomer and catalyst selection can allow polymer or oligomer blend preparation under conditions analogous to those using individual catalysts. Polymers having increased PDI are available from polymers made with mixed catalyst systems and can thus be achieved. Mixed catalyst can comprise two or more metallocene compounds and or two or more activators.

The PAOs described herein can additionally or alternatively be produced in homogeneous solution processes. Generally, this involves polymerization or oligomerization in a continuous reactor in which the polymer formed and the starting monomer and catalyst materials supplied may be agitated to reduce or avoid concentration or temperature gradients. Temperature control in the reactor can generally be obtained by balancing the heat of polymerization and with reactor cooling by reactor jackets or cooling coils or a cooled side-stream of reactant to cool the contents of the reactor, auto refrigeration, pre-chilled feeds, vaporization of liquid medium (diluent, monomers, or solvent) or combinations of the above. Adiabatic reactors with pre-chilled feeds may additionally or alternatively be used. The reactor temperature may vary with the catalyst used and the product desired. Higher temperatures can tend to give lower molecular weights, and lower temperatures can tend to give higher molecular weights; however, this is not a fixed rule. In general, the reactor temperature preferably can vary between about 0° C. and about 300° C., e.g., from about 10° C. to about 230° C. or from about 25° C. to about 200° C. Usually, it is important to control the reaction temperature as pre-determined. In order to produce fluids with narrow polydispersity, such as to promote the highest possible shear stability, it can be useful to control the reaction temperature to obtain minimum of temperature fluctuation in the reactor or over the course of the reaction time. If multiple reactors are used in series or in parallel, it may be useful to keep the temperature constant in a pre-determined value, e.g., to minimize any broadening of molecular weight distribution. In order to produce a product with broader molecular weight distribution, one can adjust the reaction temperature swing or fluctuation, or, as in series operation, the second reactor temperature may be higher than the first reactor temperature.

In parallel reactor operation, the temperatures of the two reactors may be independent. Or one can use more than one type of metallocene catalyst.

The pressure in any reactor used herein can vary from about 0.1 atmosphere to about 100 atmospheres (about 1.5 psia to about 1500 psia), e.g., from about 0.5 atm to about 80 atm (~7 psia to ~1200 psia) or from about 1.0 atm to about 50 atm (~15 psia to ~750 psia). The reaction can be carried out under an atmosphere of nitrogen or with some hydrogen. Sometimes a small amount of hydrogen may be added to the reactor to improve catalyst performance. When present, the amount of hydrogen can be kept at such a level to improve catalyst productivity, but preferably not induce too much (preferably any significant) hydrogenation of olefins, especially the feed alpha-olefins (the reaction of alpha-olefins into saturated paraffins can be very detrimental to the efficiency of the process). The amount of hydrogen partial pressure is thus preferred to be kept low, e.g., less than 50 psi (350 kPa), less than 25 psi (170 kPa), less than 10 psi (69 kPa), or less than 5 psi (35 kPa); additionally or alternatively, the concentration of hydrogen in the reactant phase, in the reactor and/or feed, can be less than 10,000 ppm (by wt.), e.g., less than 1000 ppm, less than 500 ppm, less than 100 ppm, less than 50 ppm, less than 25 ppm, or less than 10 ppm.

The reaction time or reactor residence time can depend on the catalyst used, the amount of catalyst used, and the desired alpha-olefin conversion level. Different metallocene compounds typically have different activities. Usually, a higher degree of alkyl substitution on the Cp ring, or bridging can improve catalyst productivity. High amounts of catalyst loading can tend to give higher alpha-olefin conversion at shorter reaction times. However, high amount of catalyst usage can make the production process uneconomical and difficult to manage the reaction heat or to control the reaction temperature. Therefore, it can be useful to choose a catalyst with maximum catalyst productivity to minimize the amount of metallocene and activator needed. When the catalyst system is a metallocene plus methylalumoxane, the range of methylalumoxane used can be in the range of 0.1 milligram/gram (mg/g) to 500 mg/g of alpha-olefin feed, e.g., from 0.05 mg/g to 10 mg/g. Furthermore, the molar ratios of the aluminum to metallocene (Al/M molar ratio) can range from 2 to 4000, e.g., from 10 to 2000, from 50 to 1000, or from 100 to 500. When the catalyst system is a metallocene plus a Lewis Acid or an ionic promoter with NCA component, the metallocene use can be in the range of 0.01 microgram/gram (mcg/g) to 500 mcg/g of metallocene component relative to alpha-olefin feed, e.g., from 0.1 mcg/g to 100 mcg/g, and/or the molar ratio of the NCA activator to metallocene can be in the range from 0.1 to 10, e.g., from 0.5 to 5 or from 0.5 to 3. If a co-activator of alkylaluminum compound is used, the molar ratio of the Al to metallocene can be in the range from 1 to 1000, e.g., from 2 to 500 or from 4 to 400.

Typically, it can be preferable to have the highest possible alpha-olefin conversion (close to 100%) of feed alpha-olefin in shortest possible reaction time. However, in CSTR operation, sometimes it can be beneficial to run the reaction at an optimum alpha-olefin conversion, which can be less than 100% alpha-olefin conversion, but preferably close to 100%. There are also occasions, when partial alpha-olefin conversion can be more desirable, e.g., when a narrow product PDI is desirable, because partial conversion can avoid a PDI broadening effect. If the reaction is conducted to less than 100% conversion of the alpha-olefin, the unreacted starting material after separation from other product and solvents/ diluents can be simply removed, or may be recycled to increase the total process efficiency. Conversion, also called alpha-olefin conversion, is determined by dividing the amount (grams) of isolated PAO recovered from the polymerization mixture (after the polymerization has been stopped) by the amount (grams) of alpha-olefin introduced into the reactor. (When reported in %, conversion=(grams isolated PAO/grams alpha-olefin used)×100). Preferably the conversion for the polymerization reactions described herein is 20% or more, alternatively 40% or more, alternatively 60% or more, alternatively 70% or more, alternately 80% or more, alternately 90% or more, alternately 95% or more. Isolated PAO is the PAO product obtained after solvent, unreacted monomer and other volatiles (such as dimer) have been removed (such as by vacuum flash).

Desirable residence times for any process described herein can be from 1 minute to 20 h, e.g., from 5 minutes to 10 h.

Each of these processes may also be employed in single reactor, parallel or series reactor configurations. The process can be carried out in a continuous stirred tank reactor or plug flow reactor, or more than one reactor operated in series or parallel. These reactors may or may not have internal cooling and the monomer feed may or may not be refrigerated. See the general invention of U.S. Pat. No. 5,705,577 for general process conditions.

When a solid supported catalyst is used, a slurry polymerization/oligomerization process generally operates in the similar temperature, pressure, and residence time range as described previously. In a slurry polymerization or oligomerization, a suspension of solid catalyst, promoters, monomer and comonomers are added. The suspension including diluent is intermittently or continuously removed from the reactor. The catalyst is then separated from the product by filtration, centrifuge, or settlement. The fluid is then distilled to remove solvent, any unreacted components and light product. A portion or all of the solvent and unreacted component or light components can be recycled for reuse.

If the catalyst used is un-supported or is a solution catalyst, when the reaction is complete or when the product is withdrawn from the reactor (such as in a CSTR), the product may still contain soluble, suspended, or mixed catalyst system components. These components can preferably be deactivated and/or removed. Any of the usual catalyst deactivation methods or aqueous wash methods can be used to remove the catalyst system component. Typically, the reaction can be deactivated by addition of stoichiometric amount or excess of air, moisture, alcohol, isopropanol, etc. The mixture can then be washed with dilute sodium hydroxide or with water to remove catalyst system components. The residual organic layer may then be subjected to distillation to remove solvent, which can optionally be recycled for reuse. The distillation can further remove any light reaction product, e.g., from $C_{18}$ and less. These light components can be used as diluent for further reaction or can be used as olefinic raw material for other chemical synthesis, as these light olefin by-products may have vinylidene unsaturation, most suitable for further functionalization to convert in high performance fluids. Additionally or alternatively, these light olefin products can be hydrogenated to be used as high quality paraffinic solvents.

Polymerization or oligomerization in absence of hydrogen may be advantageous to provide polymers or oligomers with high degree of unsaturated double bonds. These double bonds can be easily converted into functionalized fluids with multiple performance features. Examples for converting oligomers and/or polymers can be found in preparation of ashless dispersants, e.g., by reacting the polymers with maleic anhydride to give PAO-succinic anhydride which can then reacted with amines, alcohols, and/or polyether alcohols to convert into dispersants, such as disclosed in the book "Lubricant Additives: Chemistry and Application," ed. By Leslie R. Rudnick, p. 143-170.

Desirably, in the process of the present invention, due to the structure features of the metallocene compound, the polymerization reaction mixture exiting the polymerization reactor can typically comprise oligomers including vinylidenes, tri-substituted vinylenes, optionally di-substituted vinylenes, and optionally vinyls, optionally residual olefin monomer feed, optionally solvents, and components derived from the catalyst system.

The polymerization reaction mixture can then be quenched, e.g., by the addition of a quenching agent such as water, $CO_2$, methanol, ethanol, mixtures thereof, and the like. Subsequently, the polymerization reaction mixture can be separated to remove the residual monomer, which can be recycled to the polymerization reactor. Monomer removal can be carried out by means such as flashing under vacuum, distillation, or extraction. The resultant mixture can comprise an unsaturated PAO product including vinylidenes, tri-substituted vinylenes, optionally di-substituted vinylenes, and optionally vinyls.

Without being bound by theory, it is believed that, a non-coordinating anion with a large molecular size (e.g., dimethylanilinium tetrakisperfluoronaphthylborate) can tend to result in higher selectivity toward vinyls and a lower selectivity toward vinylidenes, as compared to non-coordinating anions with a small molecular size (e.g., dimethylanilinium tetrakisperfluorophenylborate) when used as the activator for the same metallocene compound of the present invention.

The unsaturated PAO product obtained immediately after monomer removal can contain dimers, trimers, tetramers, pentamers, and even oligomers with a higher degree of polymerization. Extraction or fractionation may be carried out to separate the product into multiple fractions with differing boiling point ranges, corresponding to differing molecular weight range and differing degree of polymerization. For example, dimers can be separated out as a low-viscosity, low boiling point fraction as one grade of product, and the residual material may be used as another unsaturated PAO product grade.

IV.6 Hydrogenation

At least a portion of the unsaturated PAO product can be hydrogenated to obtain an at least partly saturated PAO product. The unsaturated PAO product may be treated to reduce heteroatom-containing compounds to less than 600 ppm by wt. Thereafter, in some embodiments, the treated product can then be contacted with hydrogen and a hydrogenation catalyst to produce an at least partly saturated, hydrogenated PAO product, e.g., at a temperature from 25° C. to 350° C. (e.g., 100° C. to 300° C.), for a time period from 5 minutes to 100 h (e.g., from 5 minutes to 24 h), at a hydrogen pressure of from 25 psig to 2500 psig (~170 kPag to ~17 MPag), such as from 100 psig to 2000 psig (~690 kPag to ~14 MPag). Further information on hydrogenation of unsaturated PAO products can be found in U.S. Pat. No. 5,573,657 and "Lubricant Base Oil Hydrogen Refining Processes" (page 119 to 152 of Lubricant Base Oil and Wax Processing, by Avilino Sequeira, Jr., Marcel Dekker, Inc., NY, 1994).

This hydrogenation process can be accomplished, e.g., in a slurry reactor, in a batch operation, or in a continuous stirred tank reactor (CSTR), where the catalyst in 0.001 wt % to 20 wt % of the unsaturated PAO feed (e.g., from 0.01 wt % to 10 wt %), hydrogen, and the uPAOs can be continuously added to the reactor to allow for certain residence time, e.g., 5 minutes to 10 h, to allow desired (e.g., substantially complete) hydrogenation of the unsaturated olefins. The amount of catalyst added may usually be very small, just to compensate for catalyst deactivation. The catalyst and hydrogenated PAO can be continuously withdrawn from the reactor. The product mixture can be filtered, centrifuged, or settled to remove the solid hydrogenation catalyst. The catalyst can be regenerated and reused, if desired. The hydrogenated PAO can be used as-is or further distilled or fractionated to a desired level. In some cases, when the hydrogenation catalyst show little or no catalyst deactivation over long term operation, the stir tank hydrogenation process can be carried out in a manner where a fixed amount of catalyst is maintained in the reactor, such as from 0.1 wt % to 10% of the total reactant, with mostly (or only) hydrogen and PAO feed continuously added at certain feed rate, and with predominantly (or only) hydrogenated PAO was withdrawn from the reactor.

The hydrogenation process can additionally or alternatively be accomplished by a fixed bed process, in which the solid catalyst can be packed inside a tubular reactor and heated to reactor temperature. Hydrogen and PAO feed can be fed through the reactor simultaneously from the top or bottom or counter-current, e.g., to maximize the contact between hydrogen, PAO, and catalyst and to allow superior heat management. The feed rate of the PAO and hydrogen can be adjusted to give proper residence time, e.g., to allow desired (typically substantially complete) hydrogenation of the unsaturated PAOs in the feed. The hydrogenated PAO fluid can be used as-is or further distilled or fractionated to a desired level. Usually, the hydrogenated PAO product can have a bromine number of 2.0 or less.

IV.7 Functionalization

At least a portion of the unsaturated PAO product can be reacted with a chemical reagent to obtain an at least partly functionalized PAO product. However, due to the individual nature of functionalization reactions, the specificity of potential side products or by-products to be avoided, the breadth of potentially desired functionality, and thus the breadth of potential reaction conditions available or sufficient to attain desired functionality, it can be difficult to specify an appropriately set of conditions, reactors, chemical reagents, and/or catalysts/additives/etc. to encompass them all. Nevertheless, conventional functionalization techniques, as well as their reaction parameters, are known to those skilled in the chemical arts, allowing partially or completely functionalized PAO products sporting any one or more of a variety of functional groups to be readily attainable. In the case of substantially or completely functionalized PAO products, in some embodiments, the bromine number may be 2.0 or less.

V. Lubricant Base Stock

The unsaturated PAO products and the hydrogenated PAO products of the present invention, advantageously obtainable by using the processes of the present invention, can be used as a base stock for lubricating oil compositions. Preferably the hydrogenated PAO product having a bromine number no greater than 2.0 is used as a lubricating oil base stock. The base stock can be at any viscosity grade useful for any particular lubricating oil composition. The base stocks of the present invention can be blended with each other, other API Group I, II, III, IV, or V base stocks, lubricating additive packages, and/or the like, to form a lubricating oil composition. "Lubricating oil," "lubricating oil composition," and "lubricant" are used herein interchangeably. The lubricants can include internal combustion engine oils, gas turbine oils, automobile drive line fluids, power transfer fluids (e.g., hydraulic oil), processing oils, heat transfer oils (e.g., transformer oils), industrial lubricants, gear box lubricants, and the like, as well as combinations thereof.

VI. Additional Embodiments

Additionally or alternatively, the present invention can include one or more of the following embodiments:

Embodiment 1. A process for making a poly alpha-olefin, PAO, the process comprising:

contacting a feed comprising a $C_6$-$C_{32}$ alpha-olefin with a catalyst system comprising a metallocene compound in a polymerization reactor under polymerization conditions to effect a polymerization reaction to obtain a polymerization reaction mixture comprising vinylidenes, tri-substituted vinylenes, optionally di-substituted vinylenes, and optionally vinyls; and obtaining an unsaturated PAO product from the polymerization reaction mixture, wherein the unsaturated PAO product comprises vinylidenes, tri-substituted vinylenes, optionally di-substituted vinylenes, optionally vinyls, preferably wherein the conversion is 60% or more, and wherein the metallocene compound is represented by formula (F-MC):

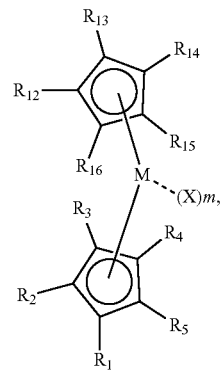

(F-MC)

wherein:

each $R^1$, $R^2$, and $R^3$ is, independently, hydrogen or a substituted or unsubstituted linear, branched linear, or cyclic $C_1$-$C_{20}$ hydrocarbyl or silylcarbyl group;

$R^4$ and $R^5$ are each independently a substituted or unsubstituted linear, branched linear, or cyclic $C_1$-$C_{30}$ hydrocarbyl or silylcarbyl group where $R^4$ and $R^5$, taken together with the carbon atoms in the first cyclopentadienyl ring to which they are directly connected, collectively form one or more substituted or unsubstituted rings annelated to the first cyclopentadienyl ring;

$R^{12}$, $R^{13}$, $R^{14}$, $R^{15}$, and $R^{16}$ are each independently a hydrogen, or a substituted or unsubstituted linear, branched linear, or cyclic $C_1$-$C_{20}$ hydrocarbyl, silylcarbyl, or germanyl group, and optionally at least three of $R^{12}$, $R^{13}$, $R^{14}$, $R^{15}$, and $R^{16}$ are not hydrogen;

M is a group 3, 4 or 5 transition metal having an integer coordination number of v; and each X is independently a halogen, a hydride, an amide, an alkoxide, a sulfide, a phosphide, a diene, an amine, a phosphine, an ether, or a $C_1$-$C_{20}$ substituted or unsubstituted linear, branched, or cyclic hydrocarbyl group, or optionally two or more X moieties may together form a fused ring or ring system; and m is an integer equal to v-2.

Embodiment 2. A process for making a poly alpha-olefin, PAO, the process comprising: contacting a feed containing a $C_6$-$C_{32}$ alpha-olefin with a catalyst system comprising a metallocene compound in a polymerization reactor under polymerization conditions to effect a polymerization reaction to obtain a polymerization reaction mixture comprising vinylidenes, tri-substituted vinylenes, and optionally di-substituted vinylenes, and optionally vinyls; and obtaining an unsaturated PAO product from the polymerization reaction mixture, wherein the polymerization reaction exhibits a selectivity toward greater than or equal to about 80 mol % vinylidenes, preferably 90 mol % vinylidenes, more preferably 96.5 mol % vinylidenes, based on total moles of vinyls, vinylidenes, di-substituted vinylenes, and tri-substituted vinylenes in the unsaturated PAO product;

wherein the metallocene compound is represented by formula (I):

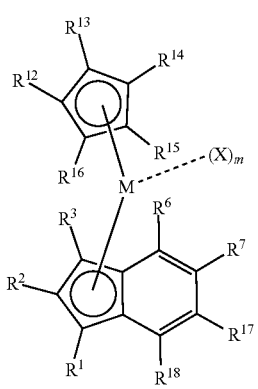

(I)

wherein:

each $R^1$, $R^2$, and $R^3$ is, independently, hydrogen or a substituted or unsubstituted linear, branched linear, or cyclic $C_1$-$C_{20}$ hydrocarbyl group, wherein a first one of $R^1$, $R^2$, and $R^3$ is a substituted or unsubstituted linear, branched linear, or cyclic $C_1$-$C_{20}$ hydrocarbyl group; a second one of $R^1$, $R^2$, and $R^3$ is hydrogen; and a third one of $R^1$, $R^2$, and $R^3$ is hydrogen, a substituted or unsubstituted linear, branched linear, or cyclic $C_1$-$C_{20}$ hydrocarbyl group;

$R^6$, $R^7$, $R^{17}$, and $R^{18}$ are each independently hydrogen; a substituted or unsubstituted linear, branched linear, or cyclic $C_1$-$C_{30}$ hydrocarbyl group; or $R^6$ and $R^7$, $R^7$ and $R^{17}$, or $R^{17}$ and $R^{18}$, taken together with the carbon atoms in the indenyl ring to which they are directly connected, collectively form one or more substituted or unsubstituted rings annelated to the indenyl ring;

$R^{12}$, $R^{13}$, $R^{14}$, and $R^{15}$ are each independently a substituted or unsubstituted linear, branched linear, or cyclic $C_1$-$C_{20}$ hydrocarbyl group;

$R^{16}$ is a substituted or unsubstituted linear, branched linear, or cyclic $C_1$-$C_{20}$ hydrocarbyl group or silylcarbyl group;

each X is independently a halogen, a hydride, an amide, an alkoxide, a sulfide, a phosphide, a diene, an amine, a phosphine, an ether, a $C_1$-$C_{20}$ substituted or unsubstituted linear, branched linear, or cyclic hydrocarbyl group, or two or more X moieties together form a fused ring or ring system;

M is a group 3, 4, or 5 transition metal having an integer coordination number of v, such as 3, 4, or 5; and m is an integer equal to v-2, such as 1, 2 or 3.

Embodiment 3. The process according to embodiment 1 or 2, wherein $R^2$ is hydrogen.

Embodiment 4. The process according to embodiment 1, 2, or 3 wherein one of $R^1$ and $R^3$ is a substituted or unsubstituted linear, branched linear, or cyclic $C_1$-$C_6$ hydrocarbyl group, and the other one of $R^1$ and $R^3$ is a hydrogen.

Embodiment 4.5. The process of embodiment 1, 2, 3, or 4, wherein the conversion is 10% (preferably 40%) or more and the polymerization reaction exhibits a selectivity toward greater than or equal to about 80 mol % vinylidenes, preferably 90 mol % vinylidenes, more preferably 96.5 mol % vinylidenes, based on total moles of vinyls, vinylidenes, di-substituted vinylenes, and tri-substituted vinylenes in the unsaturated PAO product.

Embodiment 4.6. The process of any of embodiments 1 to 4.5, wherein $R^2$ is hydrogen and one of $R^1$ and $R^3$ is a substituted or unsubstituted linear, branched linear, or cyclic $C_1$-$C_6$ hydrocarbyl group, and the other one of $R^1$ and $R^3$ is a hydrogen.

Embodiment 5. The process according to any one of embodiments 1 through 4.6, wherein $C_2$ to $C_5$ alpha olefins are absent from the feed.

Embodiment 6. The process according to any one of embodiments 1 through 5 wherein: one of $R^1$ and $R^3$ comprise an alpha Group 14 atom directly attached to the indenyl ring, a beta Group 14 atom attached to the alpha atom, and two or more, preferably three, substituted or unsubstituted linear, branched linear, or cyclic $C_1$-$C_8$ hydrocarbyl groups attached to the beta atom.

Embodiment 7. The process according to any one of embodiments 1 through 6, wherein the metallocene compound is represented by formula (II):

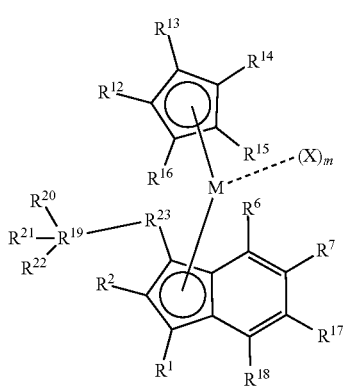

(II)

wherein:

$R^1$ and $R^2$ are hydrogen;

$R^{23}$ and $R^{19}$ comprise Group 14 atoms, such as C, Si, or Ge;

$R^{20}$, $R^{21}$, and $R^{22}$ are independently hydrogen or a substituted or unsubstituted linear, branched linear, or cyclic $C_1$-$C_{20}$ hydrocarbyl group and at least two of $R^{20}$, $R^{21}$, and $R^{22}$ are independently a substituted or unsubstituted linear, branched linear, or cyclic $C_1$-$C_{20}$ hydrocarbyl group, wherein at least two of $R^{20}$, $R^{21}$, and $R^{22}$ are a substituted or unsubstituted linear, branched linear, or cyclic $C_1$-$C_{20}$ hydrocarbyl group;

$R^6$, $R^7$, $R^{17}$, and $R^{18}$ are each independently hydrogen; a substituted or unsubstituted linear, branched linear, or cyclic $C_1$-$C_{30}$ hydrocarbyl group; or $R^6$ and $R^7$, $R^7$ and $R^{17}$, or $R^{17}$ and $R^{18}$, taken together with the carbon atoms in the indenyl ring to which they are directly connected, collectively form one or more substituted or unsubstituted rings annelated to the indenyl ring;

$R^{12}$, $R^{13}$, $R^{14}$, $R^{15}$, and $R^{16}$ are each independently a substituted or unsubstituted linear, branched linear, or cyclic $C_1$-$C_8$ hydrocarbyl group;

each X is independently a halogen, a hydride, an amide, an alkoxide, a sulfide, a phosphide, a diene, an amine, a phosphine, an ether, or a $C_1$-$C_{20}$ substituted or unsubstituted linear, branched linear, or cyclic hydrocarbyl group, or two or more X moieties together form a fused ring or ring system;

M is a group 4 transition metal having an integer coordination number of v; and m is an integer equal to v-2.

Embodiment 8. The process according to any one of Embodiments 1 through 7, wherein $R^6$ and $R^7$, or $R^7$ and $R^{17}$, or $R^{17}$ and $R^{18}$, taken together with the respective carbon atoms in the indenyl ring to which they are directly connected, form a ring annelated to the indenyl ring.

Embodiment 9. The process according to embodiment 8, wherein the ring annelated to the indenyl ring comprises one or more saturated carbon atoms.

Embodiment 10. The process according to any one of embodiments 1 through 9, wherein at least four of $R^{12}$, $R^{13}$, $R^{14}$, $R^{15}$, and $R^{16}$ are each independently a substituted or unsubstituted linear, branched linear, or cyclic $C_1$-$C_8$ hydrocarbyl group, preferably methyl or ethyl.

Embodiment 11. The process according to any one of embodiments 1 through 10, wherein each $R^{12}$, $R^{13}$, $R^{14}$, $R^{15}$, and $R^{16}$ are independently a substituted or unsubstituted linear, branched linear, or cyclic $C_1$-$C_8$ hydrocarbyl group, preferably $R^{16}$ is a substituted or unsubstituted linear, branched linear, or cyclic $C_1$-$C_8$ hydrocarbyl group, preferably methyl or ethyl.

Embodiment 12. The process according to any one of embodiments 1 through 11, wherein:
  i) at least three of $R^{12}$, $R^{13}$, $R^{14}$, $R^{15}$, and $R^{16}$ if present are not hydrogen;
  ii) two or more of $R^{12}$, $R^{13}$, $R^{14}$, $R^{15}$ and $R^{16}$ if present together form a fused ring or ring system;
  iii) at least two of $R^6$, $R^7$, $R^{17}$, and $R^{18}$ are hydrogen;
  iv) each X is independently a halogen or a substituted or unsubstituted linear, branched linear, or cyclic $C_1$-$C_6$ hydrocarbyl group;
  v) M comprises Zr or Hf;
  or a combination thereof.

Embodiment 13. The process according to any one of embodiments 1 through 12, wherein $R^{12}$, $R^{13}$, $R^{14}$, $R^{15}$, and $R^{16}$ are each independently a substituted or unsubstituted linear, branched linear, or cyclic $C_1$-$C_8$ hydrocarbyl group, preferably methyl or ethyl.

Embodiment 14. The process according to any one of embodiments 1 through 13, wherein the metallocene compound is represented by formula (I-B), (III-B), (IV-B), (VI), (VIII), (IX), (X), (XI), (XII), (XV), (XVII), (XVIII), or (XIX):

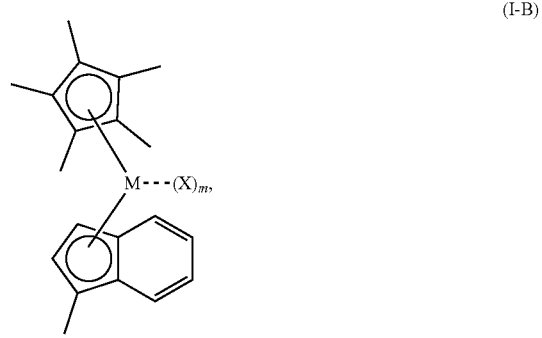

(I-B)

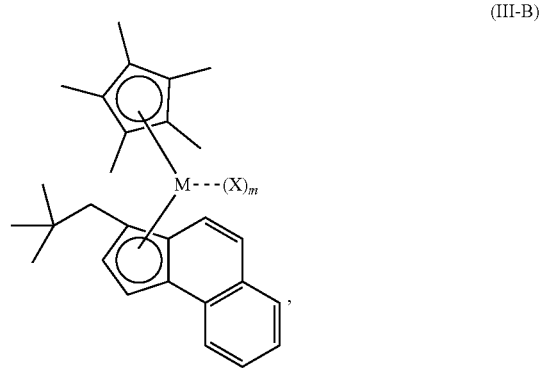

(III-B)

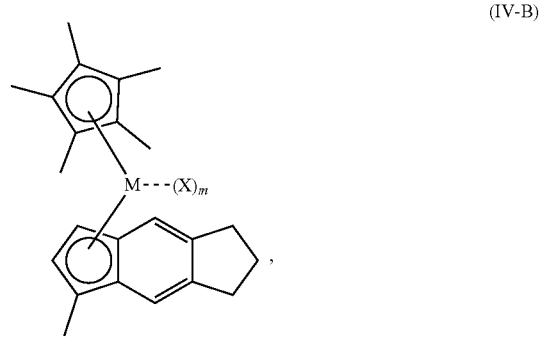

(IV-B)

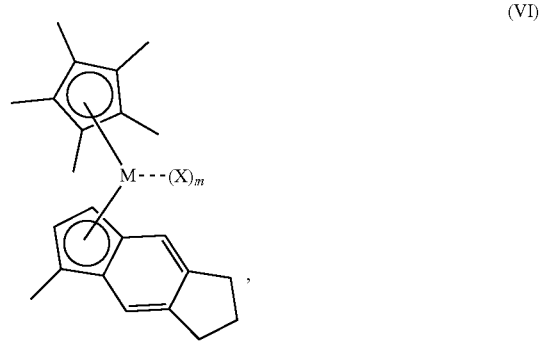

(VI)

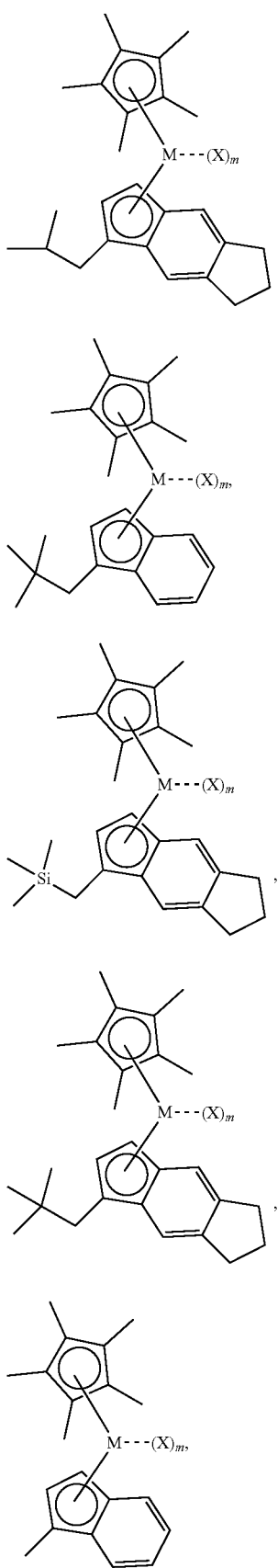

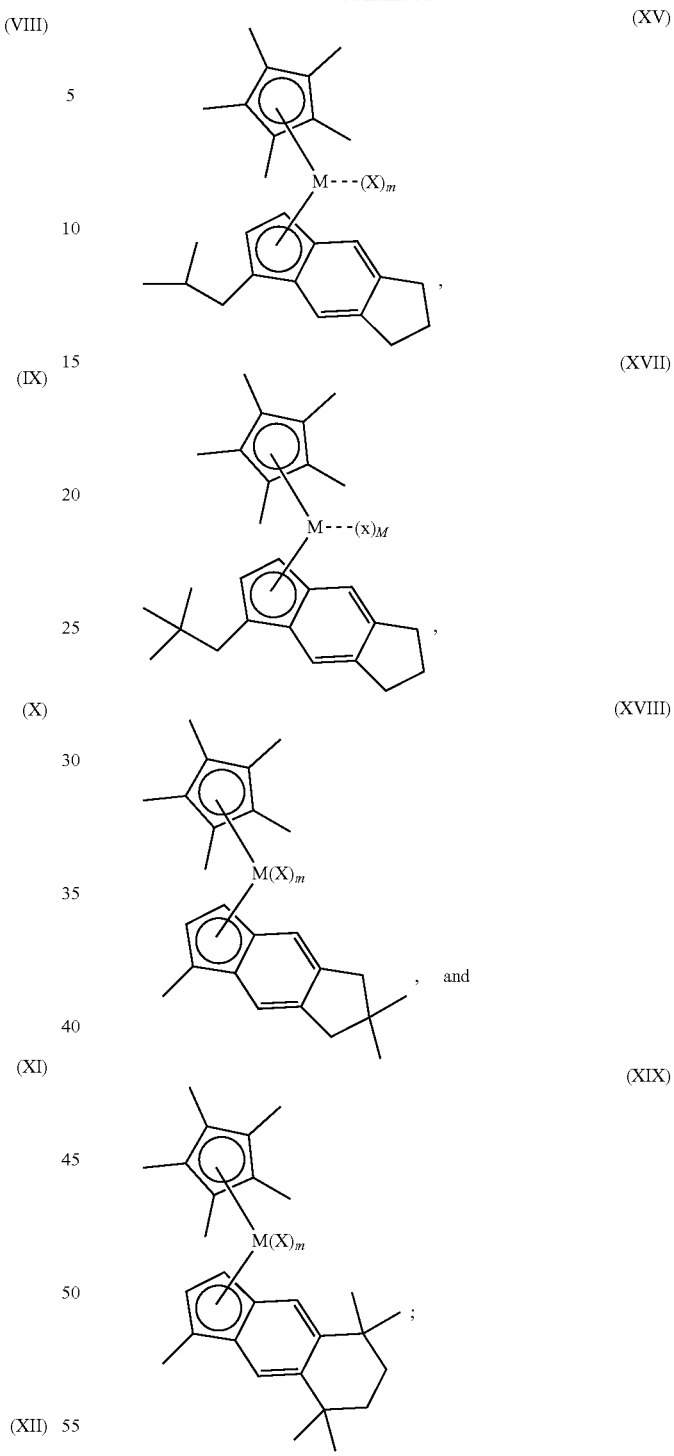

wherein each X is independently a halogen, a hydride, an amide, an alkoxide, a sulfide, a phosphide, a diene, an amine, a phosphine, an ether, or a $C_1$-$C_{20}$ substituted or unsubstituted linear, branched linear, or cyclic hydrocarbyl group, or two or more X moieties may together form a fused ring or ring system; M is Hf or Zr; and m is 2.

Embodiment 15. The process according to any one of embodiments 1 through 14 wherein the metallocene is not represented by formula (I-B).

Embodiment 16. The process according to any one of embodiments 1 through 15, wherein the polymerization reaction exhibits a selectivity toward a combination of greater than or equal to about 96.5 mol % vinylidenes, from 0.5 mol % to 3.5 mol % tri-substituted vinylenes, less than or equal to about 1.5 mol % di-substituted vinylenes, and less than or equal to about 1.5 mol % vinyls, based on total moles of vinyls, vinylidenes, di-substituted vinylenes, and tri-substituted vinylenes in the unsaturated PAO product.

Embodiment 17. The process according to any one of embodiments 1 through 16, wherein the polymerization reaction exhibits a selectivity toward a combination of vinylidenes of equal to or greater than 97.0 mol %, preferably equal to or greater than 97.9 mol %; tri-substituted vinylenes of less than 2.1 mol %; di-substituted vinylenes of 0.5 mol % or less; and vinyls of 1.0 mol % or less, based on total moles of vinyls, vinylidenes, di-substituted vinylenes, and tri-substituted vinylenes in the unsaturated PAO product.

Embodiment 18. The process according to any one of embodiments 1 through 17, wherein the polymerization reaction exhibits a selectivity towards a combination of vinylidenes and tri-substituted vinylenes of collectively greater than 98.0 mol %, preferably greater than 98.5 mol %, and a combination of di-substituted vinylenes and vinyls of collectively less than 2.0 mol %, preferably less than 1.5 mol %, based on total moles of vinyls, vinylidenes, di-substituted vinylenes, and tri-substituted vinylenes in the unsaturated PAO product.

Embodiment 19. The process according to any one of embodiments 1 through 18, wherein the polymerization reaction results in the unsaturated PAO product having a number average molecular weight (Mn) of 1500 g/mol or less, preferably from 300 to 800 g/mol, as measured by $^1$H NMR.

Embodiment 20. The process according to any one of embodiments 1 through 19, wherein the catalyst system further comprises a non-coordinating anion type activator, preferably wherein the non-coordinating anion type activator comprises: N,N-dimethylanilinium tetrakis(perfluorophenyl)borate, N,N-dimethylanilinium tetrakis(perfluoro-naphthyl)borate, triphenylcarbonium tetrakis(perfluorophenyl)borate, triphenylcarbonium tetrakis(perfluoronaphthyl)borate, N,N-dimethylanilinium tetrakis(perfluorophenyl)aluminate, N,N-dimethylanilinium tetrakis(perfluoronaphthyl)aluminate, or combinations thereof.

Embodiment 21. The process according to any one of embodiments 1 through 20, wherein:

the polymerization conditions comprise a reaction temperature from 40° C. to 150° C.;

an average activity level of at least 1200 g/s·mol;

the polymerization reaction mixture exhibits a yield of at least 10%;

or a combination thereof.

Embodiment 22. The process according to any one of embodiments 1 through 21, further comprising:

a) contacting the unsaturated PAO product with hydrogen to convert at least a portion of the unsaturated PAO product to a hydrogenated PAO product;

b) contacting the unsaturated PAO product with a chemical reagent to convert at least a portion of the unsaturated PAO product to a functionalized PAO product; or a combination thereof.

Embodiment 23. The process according to any one of embodiments 1 through 22, wherein:

the feed comprises $C_6$-$C_{24}$ alpha-olefin;

wherein any combination of $C_2$-$C_5$ alpha-olefins are collectively present in the alpha-olefin feed at no higher than 25 mol %, based on the total moles of the alpha-olefins supplied to the polymerization reactor, preferably wherein the alpha-olefin feed is substantially free of ethylene, propylene, $C_4$ alpha-olefins, and $C_5$ alpha-olefins;

or a combination thereof.

Embodiment 24. An unsaturated poly alpha-olefin (PAO) product produced according to any one of embodiments 1 through 23.

Embodiment 25. An unsaturated poly alpha-olefin (PAO) product comprising greater than or equal to about 80 mol % vinylidenes, preferably 90 mol % vinylidenes, more preferably 96.5 mol % vinylidenes, based on total moles of vinyls, vinylidenes, di-substituted vinylenes, and tri-substituted vinylenes contained therein and having an Mn of less than 5000 g/mol as determined by $^1$H NMR.

Embodiment 26. The unsaturated poly alpha-olefin (PAO) product of embodiment 24 or embodiment 25, comprising:

96.5 mol % to 99.9 mol % of vinylidenes;

0.1 mol % to 3.5 mol % of ti-substituted vinylenes;

3.0 mol % or less of di-substituted vinylenes;

3.0 mol % or less of vinyl groups; based on total moles of vinylidenes, tri-substituted vinylenes, di-substituted vinylenes, and vinylidenes contained therein; and a number average molecular weight (Mn) of 1500 g/mol or less as measured by $^1$H NMR.

Embodiment 27. The unsaturated poly alpha-olefin (PAO) product according to any one of embodiments 24 through 26, comprising:

less than or equal to about 1.0 mol % di-substituted vinylenes, when present;

less than or equal to about 1.0 mol % vinyl groups when present; and a number average molecular weight (Mn) of 1000 g/mol or less as measured by $^1$H NMR.

Embodiment 28. The unsaturated poly alpha-olefin (PAO) product according to any one of embodiments 24 through 27, comprising from 98 mol % to 99.5 mol % of a combination of vinylidenes and tri-substituted vinylenes; 0.5 mol % to 2 mol % of a combination of di-substituted vinylenes and vinyl groups; and a number average molecular weight (Mn) of 800 g/mol or less as measured by $^1$HNMR.

Embodiment 29. A catalyst compound suitable to produce an unsaturated PAO product according to any one of embodiments 24 through 28.

Embodiment 30. A catalyst compound suitable to produce an unsaturated PAO product from $C_6$-$C_{32}$ alpha-olefin under polymerization conditions, comprising:

a polymerization selectivity suitable to form an unsaturated PAO product comprising:

greater than or equal to about 80 mol % vinylidenes, preferably 90 mol % vinylidenes, more preferably 96.5 mol % vinylidenes, based on total moles of vinyls, vinylidenes, di-substituted vinylenes, and tri-substituted vinylenes in the unsaturated PAO product; represented by the formula (F-MC2):

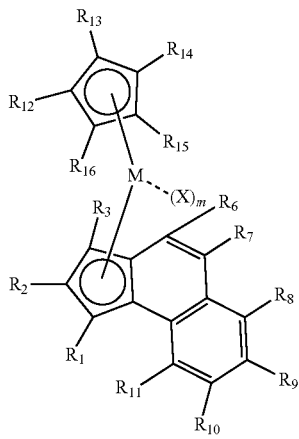

(F-MC2)

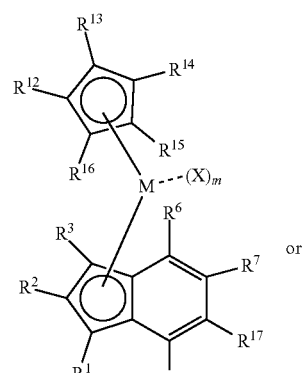

(I)

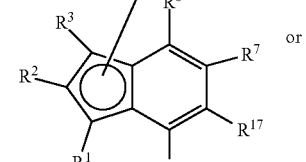

or

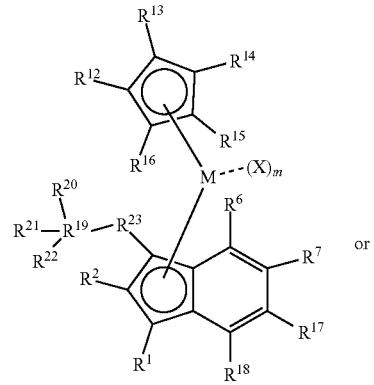

(II)

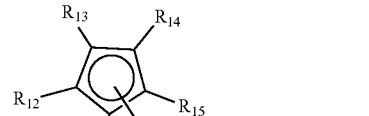

or

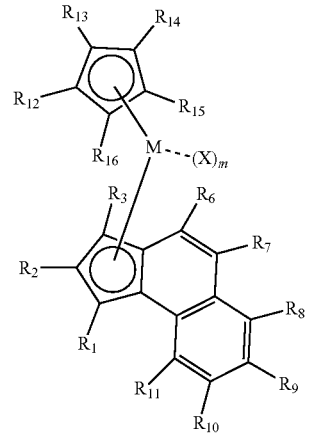

(F-MC2)

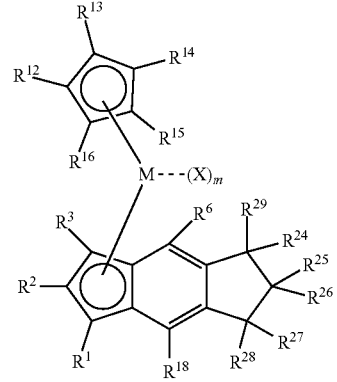

or (IV)

in which one of $R^1$, $R^2$, and $R^3$ is an alpha Group 14 atom directly attached to the indenyl ring, and a beta Group 14 atom attached to the alpha atom, and two or more, preferably three, substituted or unsubstituted linear, branched linear, or cyclic $C_1$-$C_8$ hydrocarbyl groups attached to the beta atom, and either:

(i) two of $R^1$, $R^2$, and $R^3$ are each hydrogen, or (ii) one of $R^1$, $R^2$, and $R^3$ is hydrogen and one of $R^1$, $R^2$, and $R^3$, taken together with $R^{16}$ is a bridging group connecting the first and second cyclopentadienyl rings;

$R^6$, $R^7$, $R^8$, $R^9$, $R^{10}$, and $R^{11}$ are each independently a hydrogen or a substituted or unsubstituted linear, branched linear, or cyclic $C_1$-$C_{20}$ hydrocarbyl group;

$R^{12}$, $R^{13}$, $R^{14}$, and $R^{15}$ are each independently a hydrogen, or a substituted or unsubstituted linear, branched linear, or cyclic $C_1$-$C_{20}$ hydrocarbyl group;

$R^{16}$ is a hydrogen, a substituted or unsubstituted linear, branched linear, or cyclic $C_1$-$C_{20}$ hydrocarbyl group or silylcarbyl group;

each X is independently a halogen, a hydride, an amide, an alkoxide, a sulfide, a phosphide, a diene, an amine, a phosphine, an ether, or a $C_1$-$C_{20}$ substituted or unsubstituted linear, branched linear, or cyclic hydrocarbyl group, or two or more X moieties together form a fused ring or ring system;

M is a group 3, 4 or 5 transition metal having an integer coordination number of v; and m is an integer equal to v-2.

Embodiment 31. The catalyst compound according to embodiments 29 or 30, wherein the polymerization selectivity is suitable to form an unsaturated PAO product comprising:

96.5 mol % to 99.9 mol % of vinylidenes;

0.1 mol % to 3.5 mol % of tri-substituted vinylenes;

2.0 mol % or less of di-substituted vinylenes;

2.0 mol % or less of vinyl groups;

based on total moles of vinyls, vinylidenes, di-substituted vinylenes, and tri-substituted vinylenes in the unsaturated PAO product; and a number average molecular weight (Mn) of 1500 g/mol or less as measured by $^1$H NMR.

Embodiment 32. The catalyst compound according to any one of embodiments 29 through 31, represented by formula (I), (II), (F-MC2), or (IV):

wherein:
  i) according to formula (I):
    a first one of $R^1$ or $R^3$ is a substituted or unsubstituted linear, branched linear, or cyclic $C_1$-$C_{20}$ hydrocarbyl group;
    a second one of $R^1$, $R^2$, and $R^3$ is a hydrogen;
    the third one of $R^1$, $R^2$, and $R^3$ is a hydrogen connecting the indenyl and cyclopentadienyl rings;
    $R^6$, $R^7$, $R^{17}$, and $R^{18}$ are each independently hydrogen, a substituted or unsubstituted linear, branched linear, or cyclic $C_1$-$C_{30}$ hydrocarbyl group; and
    $R^{12}$, $R^{13}$, $R^{14}$, $R^{15}$, and $R^{16}$ are each independently a substituted or unsubstituted linear, branched linear, or cyclic $C_1$-$C_{20}$ hydrocarbyl group or $R^{16}$ may be a substituted or unsubstituted linear, branched linear, or cyclic $C_1$-$C_{20}$, preferably $C_1$-$C_8$, hydrocarbyl group silylcarbyl group; or
  ii) according to formula (II):
    $R^1$ and $R^2$ are hydrogen;
    $R^{23}$ and $R^{19}$ comprise Group 14 atoms, such as C, Si, or Ge (preferably $R^{23}$ is carbon and $R^{19}$ is carbon or silicon);
    $R^{20}$, $R^{21}$, and $R^{22}$ are independently hydrogen or a substituted or unsubstituted linear, branched linear, or cyclic $C_1$-$C_{20}$ hydrocarbyl group, wherein at least two of $R^{20}$, $R^{21}$, and $R^{22}$ are a substituted or unsubstituted linear, branched linear, or cyclic $C_1$-$C_{20}$ hydrocarbyl group;
    $R^6$, $R^7$, $R^{17}$, and $R^{18}$ are each independently hydrogen, a substituted or unsubstituted linear, branched linear, or cyclic $C_1$-$C_{30}$ hydrocarbyl group, or two of $R^6$, $R^7$, $R^{17}$, and $R^{18}$ taken together with the carbon atoms in the indenyl ring to which they are directly connected, collectively form one or more substituted or unsubstituted rings annelated to the indenyl ring; and
    $R^{12}$, $R^{13}$, $R^{14}$, $R^{15}$, and $R^{16}$ are each independently a substituted or unsubstituted linear, branched linear, or cyclic $C_1$-$C_{20}$ hydrocarbyl group; or
  iii) according to formula (F-MC2):
    one of $R^1$ and $R^3$ is a substituted or unsubstituted linear, branched linear, or cyclic $C_1$-$C_{20}$ hydrocarbyl group;
    two of $R^1$, $R^2$, and $R^3$ are each hydrogen;
    $R^6$, $R^7$, $R^8$, $R^9$, $R^{10}$, and $R^{11}$ are each independently hydrogen, a substituted or unsubstituted linear, branched linear, or cyclic $C_1$-$C_{30}$ hydrocarbyl group, or two of $R^6$, $R^7$, $R^8$, $R^9$, $R^{10}$, and $R^{11}$ taken together with the carbon atoms in the benz-indenyl ring to which they are directly connected, collectively form one or more substituted or unsubstituted rings annelated to the benz-indenyl ring; and
    $R^{12}$, $R^{13}$, $R^{14}$, $R^{15}$, and $R^{16}$ are each independently a substituted or unsubstituted linear, branched linear, or cyclic $C_1$-$C_{20}$ hydrocarbyl group; or
  iv) according to formula (IV):
    one of $R^1$ and $R^3$ is a substituted or unsubstituted linear, branched linear, or cyclic $C_1$-$C_{20}$ hydrocarbyl group;
    two of $R^1$, $R^2$, and $R^3$ are each hydrogen;
    $R^6$, $R^{18}$, $R^{29}$, $R^{24}$, $R^{25}$, $R^{26}$, and $R^{27}$ are each independently hydrogen, a substituted or unsubstituted linear, branched linear, or cyclic $C_1$-$C_{30}$ hydrocarbyl group, or two of $R^6$, $R^{18}$, $R^{29}$, $R^{24}$, $R^{25}$, $R^{26}$, and $R^{27}$ taken together with the carbon atoms in the cyclopentan-indenyl ring to which they are directly connected, collectively form one or more substituted or unsubstituted rings annelated to the cyclopentan-indenyl ring; and
    $R^{12}$, $R^{13}$, $R^{14}$, $R^{15}$ and $R^{16}$ are each independently a substituted or unsubstituted linear, branched linear, or cyclic $C_1$-$C_{20}$ hydrocarbyl group;
  wherein in the formulae (I), (II), (III), (IV):
    each X is independently a halogen, a hydride, an amide, an alkoxide, a sulfide, a phosphide, a diene, an amine, a phosphine, an ether, a $C_1$-$C_{20}$ substituted or unsubstituted linear, branched linear, or cyclic hydrocarbyl group, or two or more X moieties together form a fused ring or ring system;
    M is a transition metal having an integer coordination number of v; and
    m is an integer equal to v-2.

Embodiment 33. The catalyst compound according to any one of embodiments 29 through 32, comprising a polymerization selectivity suitable to form an unsaturated PAO product comprising:
  greater than or equal to about 96.5 mol % vinylidenes;
  less than or equal to about 3.5 mol % tri-substituted vinylenes;
  less than or equal to about 1.0 mol % di-substituted vinylenes, when present;
  less than or equal to about 1.0 mol % vinyl groups when present; based on total moles of vinyls, vinylidenes, di-substituted vinylenes, and tri-substituted vinylenes in the unsaturated PAO product; and
  a number average molecular weight (Mn) of 1500 g/mol or less as measured by $^1$H NMR.

Embodiment 34. The catalyst compound according to any one of embodiments 29 through 33, represented by formula (III-B), (IV-B), (VI), (VIII), (IX), (X), (XI), (XII), (XV), (XVII), (XVIII), or (XIX):

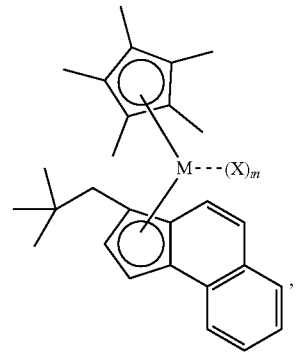
(III-B)

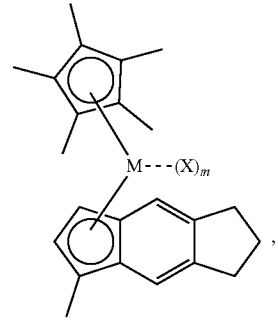
(IV-B)

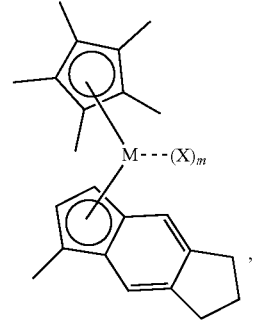
(VI)

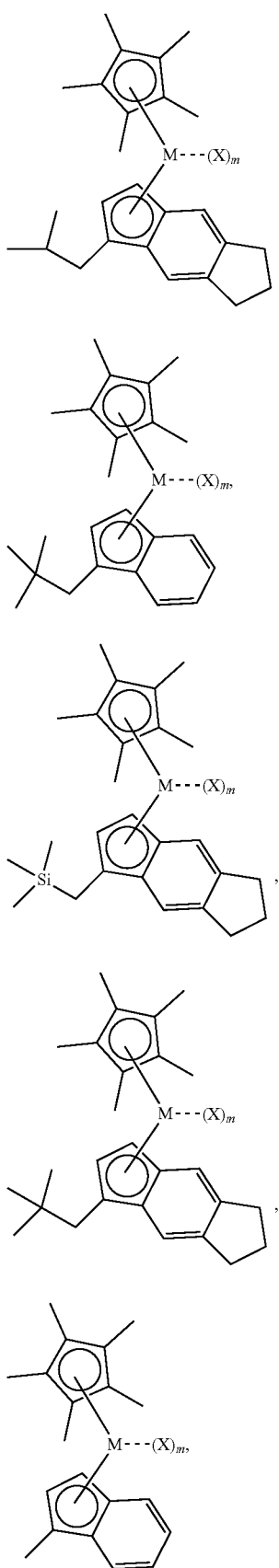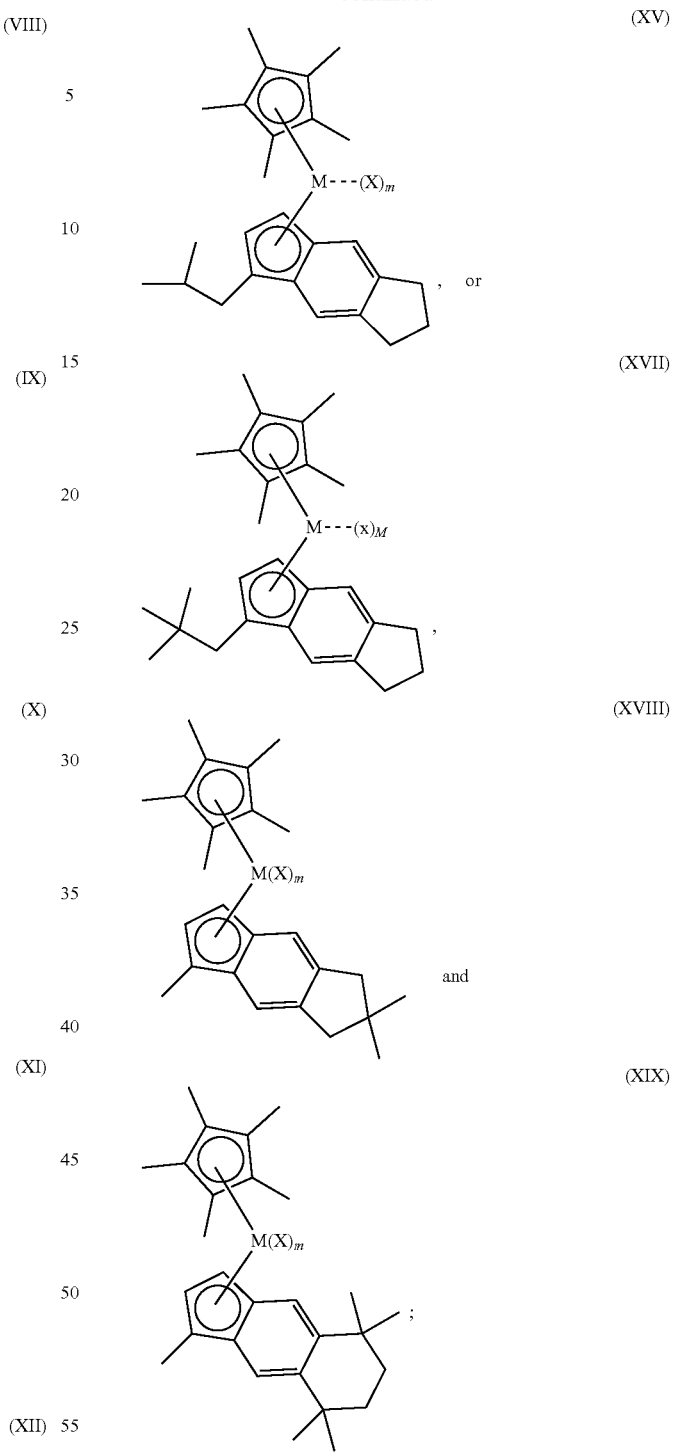

wherein each X is independently a halogen, a hydride, an amide, an alkoxide, a sulfide, a phosphide, a diene, an amine, a phosphine, an ether, or a $C_1$-$C_{20}$ substituted or unsubstituted linear, branched linear, or cyclic hydrocarbyl group, or two or more X moieties may together form a fused ring or ring system;

M is a group 3, 4 or 5 transition metal having an integer coordination number of v; and m is an integer equal to v-2.

This invention further relates to:
1. A process for making a poly alpha-olefin, PAO, the process comprising:

contacting a feed comprising a $C_6$-$C_{32}$ alpha-olefin with a catalyst system comprising a metallocene compound in a polymerization reactor under polymerization conditions to effect a polymerization reaction to obtain a polymerization reaction mixture comprising vinylidenes, tri-substituted vinylenes, optionally di-substituted vinylenes, and optionally vinyls; and obtaining an unsaturated PAO product from the polymerization reaction mixture, wherein the unsaturated PAO product comprises vinylidenes, tri-substituted vinylenes, optionally di-substituted vinylenes, optionally vinyls, wherein the metallocene compound is represented by formula (F-MC):

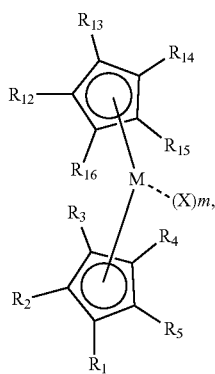

(F-MC)

wherein:

each $R^1$, $R^2$, and $R^3$ is, independently, hydrogen or a substituted or unsubstituted linear, branched linear, or cyclic $C_1$-$C_{20}$ hydrocarbyl or silylcarbyl group;

$R^4$ and $R^5$ are each independently a substituted or unsubstituted linear, branched linear, or cyclic $C_1$-$C_{30}$ hydrocarbyl or silylcarbyl group where $R^4$ and $R^5$, taken together with the carbon atoms in the first cyclopentadienyl ring to which they are directly connected, collectively form one or more substituted or unsubstituted rings annelated to the first cyclopentadienyl ring;

$R^{12}$, $R^{13}$, $R^{14}$, $R^{15}$, and $R^{16}$ are each independently a hydrogen, or a substituted or unsubstituted linear, branched linear, or cyclic $C_1$-$C_{20}$ hydrocarbyl, silylcarbyl, or germanyl group, and optionally at least three of $R^{12}$, $R^{13}$, $R^{14}$, $R^{15}$, and $R^{16}$ are not hydrogen;

M is a group 3, 4 or 5 transition metal having an integer coordination number of v;

each X is independently a halogen, a hydride, an amide, an alkoxide, a sulfide, a phosphide, a diene, an amine, a phosphine, an ether, or a $C_1$-$C_{20}$ substituted or unsubstituted linear, branched, or cyclic hydrocarbyl group, or optionally two or more X moieties may together form a fused ring or ring system; and m is an integer equal to v-2.

2. The process of paragraph 1 wherein: the process comprises obtaining an unsaturated PAO product from the polymerization reaction mixture, wherein the polymerization reaction exhibits a selectivity toward greater than or equal to about 80 mol % vinylidenes, preferably 90 mol % vinylidenes, more preferably 96.5 mol % vinylidenes, based on total moles of vinyls, vinylidenes, di-substituted vinylenes, and tri-substituted vinylenes in the unsaturated PAO product; and wherein the metallocene compound is represented by formula (I):

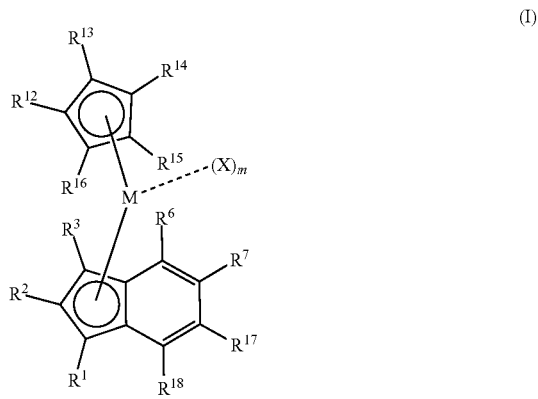

(I)

wherein:

each $R^1$, $R^2$, and $R^3$ is, independently, hydrogen or a substituted or unsubstituted linear, branched linear, or cyclic $C_1$-$C_{20}$ hydrocarbyl group, wherein a first one of $R^1$, $R^2$, and $R^3$ is a substituted or unsubstituted linear, branched linear, or cyclic $C_1$-$C_{20}$ hydrocarbyl group; a second one of $R^1$, $R^2$, and $R^3$ is hydrogen; and a third one of $R^1$, $R^2$, and $R^3$ is hydrogen, a substituted or unsubstituted linear, branched linear, or cyclic $C_1$-$C_{20}$ hydrocarbyl group;

$R^6$, $R^7$, $R^{17}$, and $R^{18}$ are each independently hydrogen; a substituted or unsubstituted linear, branched linear, or cyclic $C_1$-$C_{30}$ hydrocarbyl group; or $R^6$ and $R^7$, $R^7$ and $R^{17}$, or $R^{17}$ and $R^{18}$, taken together with the carbon atoms in the indenyl ring to which they are directly connected, collectively form one or more substituted or unsubstituted rings annelated to the indenyl ring;

$R^{12}$, $R^{13}$, $R^{14}$, and $R^{15}$ are each independently a substituted or unsubstituted linear, branched linear, or cyclic $C_1$-$C_{20}$ hydrocarbyl group;

$R^{16}$ is a substituted or unsubstituted linear, branched linear, or cyclic $C_1$-$C_{20}$ hydrocarbyl group or silylcarbyl group;

each X is independently a halogen, a hydride, an amide, an alkoxide, a sulfide, a phosphide, a diene, an amine, a phosphine, an ether, a $C_1$-$C_{20}$ substituted or unsubstituted linear, branched linear, or cyclic hydrocarbyl group, or two or more X moieties together form a fused ring or ring system;

M is a group 3, 4 or 5 transition metal having an integer coordination number of v; and m is an integer equal to v-2.

3. The process of paragraph 1, wherein the conversion is 10% or more and the polymerization reaction exhibits a selectivity toward greater than or equal to about 80 mol % vinylidenes, preferably 90 mol % vinylidenes, more preferably 96.5 mol % vinylidenes, based on total moles of vinyls, vinylidenes, di-substituted vinylenes, and tri-substituted vinylenes in the unsaturated PAO product.

4. The process of paragraph 2, where in the conversion is 40% or more.

5. The process of paragraph 1 or 2, wherein $R^2$ is hydrogen.

6. The process of paragraph 1 or 2, wherein $R^2$ is hydrogen and at least one of $R^1$ and $R^3$ is not hydrogen.

7. The process of paragraph 1 or 2, wherein $R^2$ is hydrogen and one of $R^1$ and $R^3$ is a substituted or unsubstituted linear, branched linear, or cyclic $C_1$-$C_6$ hydrocarbyl group, and the other one of $R^1$ and $R^3$ is a hydrogen.

8. The process of any paragraphs 1 to 7, wherein: one of $R^1$ and $R^3$ comprise an alpha Group 14 atom directly attached to the indenyl ring, a beta Group 14 atom attached to the alpha atom, and two or more, preferably three, substituted or unsubstituted linear, branched linear, or cyclic $C_1$-$C_8$ hydrocarbyl groups attached to the beta atom.

9. The process of any paragraphs 1, 2, 3, or 4, wherein the metallocene compound is represented by formula (II):

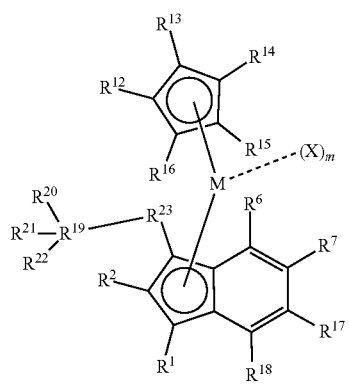

(II)

wherein:

$R^1$ and $R^2$ are hydrogen;

$R^{23}$ and $R^{19}$ comprise Group 14 atoms, preferably C, Ge, or Si;

$R^{20}$, $R^{21}$, and $R^{22}$ are independently hydrogen or a substituted or unsubstituted linear, branched linear, or cyclic $C_1$-$C_{20}$ hydrocarbyl group and at least two of $R^{20}$, $R^{21}$, and $R^{22}$ are independently a substituted or unsubstituted linear, branched linear, or cyclic $C_1$-$C_{20}$ hydrocarbyl group, wherein at least two of $R^{20}$, $R^{21}$, and $R^{22}$ are a substituted or unsubstituted linear, branched linear, or cyclic $C_1$-$C_{20}$ hydrocarbyl group;

$R^6$, $R^7$, $R^{17}$, and $R^{18}$ are each independently hydrogen; a substituted or unsubstituted linear, branched linear, or cyclic $C_1$-$C_{30}$ hydrocarbyl group; or $R^6$ and $R^7$, $R^7$ and $R^{17}$, or $R^{17}$ and $R^{18}$, taken together with the carbon atoms in the indenyl ring to which they are directly connected, collectively form one or more substituted or unsubstituted rings annelated to the indenyl ring;

$R^{12}$, $R^{13}$, $R^{14}$, $R^{15}$, and $R^{16}$ are each independently a substituted or unsubstituted linear, branched linear, or cyclic $C_1$-$C_8$ hydrocarbyl group;

each X is independently a halogen, a hydride, an amide, an alkoxide, a sulfide, a phosphide, a diene, an amine, a phosphine, an ether, or a $C_1$-$C_{20}$ substituted or unsubstituted linear, branched linear, or cyclic hydrocarbyl group, or two or more X moieties together form a fused ring or ring system;

M is a group 3, 4 or 5 transition metal having an integer coordination number of v; and m is an integer equal to v-2.

10. The process of any paragraphs 2 to 9 wherein $R^6$ and $R^7$, or $R^7$ and $R^{17}$, or $R^{17}$ and $R^{18}$, taken together with the respective carbon atoms in the indenyl ring to which they are directly connected, form a ring annelated to the indenyl ring.

11. The process of paragraph 10 wherein the ring annelated to the indenyl ring comprises one or more saturated carbon atoms.

12. The process of any of paragraphs 1 to 11 wherein at least four of $R^{12}$, $R^{13}$, $R^{14}$, $R^{15}$, and $R^{16}$ are each independently a substituted or unsubstituted linear, branched linear, or cyclic $C_1$-$C_8$ hydrocarbyl group, preferably methyl or ethyl.

13. The process of paragraph 12, wherein each $R^{12}$, $R^{13}$, $R^{14}$, $R^{15}$, and $R^{16}$ are independently a substituted or unsubstituted linear, branched linear, or cyclic $C_1$-$C_8$ hydrocarbyl group, preferably $R^{16}$ is a substituted or unsubstituted linear, branched linear, or cyclic $C_1$-$C_8$ hydrocarbyl group, preferably methyl or ethyl.

14. The process of any of paragraphs 1 to 13 wherein:

i) at least three of $R^{12}$, $R^{13}$, $R^{14}$, $R^{15}$, and $R^{16}$ are independently a substituted or unsubstituted linear, branched linear, or cyclic $C_1$-$C_8$ hydrocarbyl group;

ii) two or more of $R^{12}$, $R^{13}$, $R^{14}$, $R^{15}$ and $R^{16}$ if present together form a fused ring or ring system;

iii) at least two of $R^6$, $R^7$, $R^{17}$, and $R^{18}$ are hydrogen;

iv) each X is independently a halogen or a substituted or unsubstituted linear, branched linear, or cyclic $C_1$-$C_6$ hydrocarbyl group;

v) M comprises Zr or Hf;

or a combination thereof.

15. The process of any of paragraphs 1 to 14, wherein $R^{12}$, $R^{13}$, $R^{14}$, $R^{15}$, and $R^{16}$ are each independently a substituted or unsubstituted linear, branched linear, or cyclic $C_1$-$C_8$ hydrocarbyl group, preferably methyl or ethyl.

16. The process of any of paragraphs 1 to 15, wherein the metallocene compound is represented by formula (I-B), (III-B), (IV-B), (VI), (VIII), (IX), (X), (XI), (XII), (XV), (XVII), (XVIII), or (XIX):

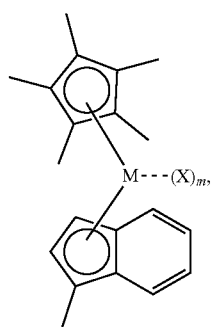

(I-B)

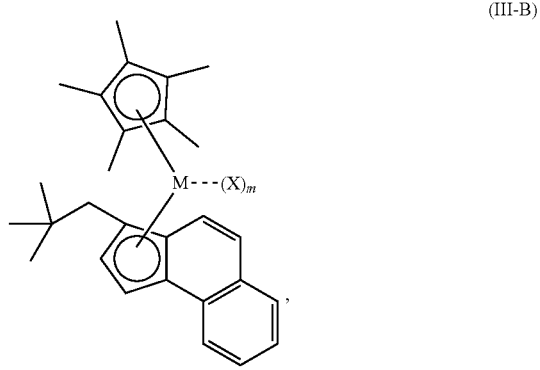

(III-B)

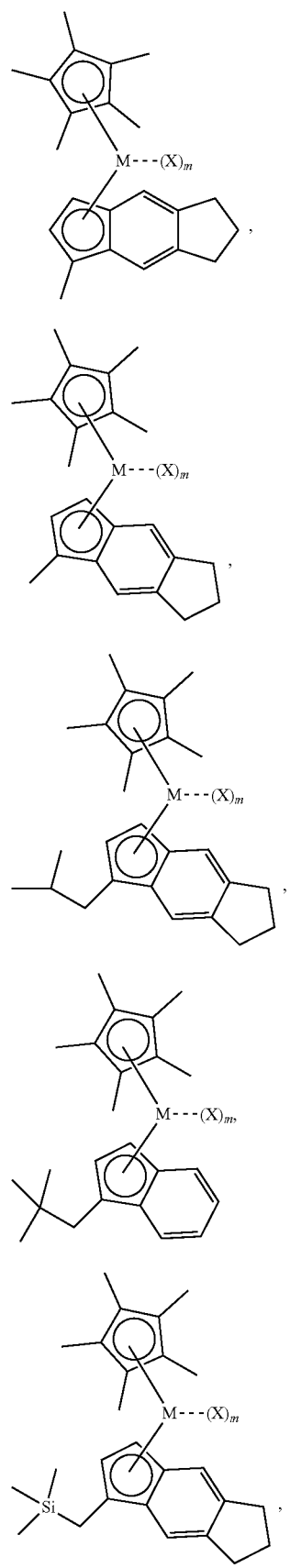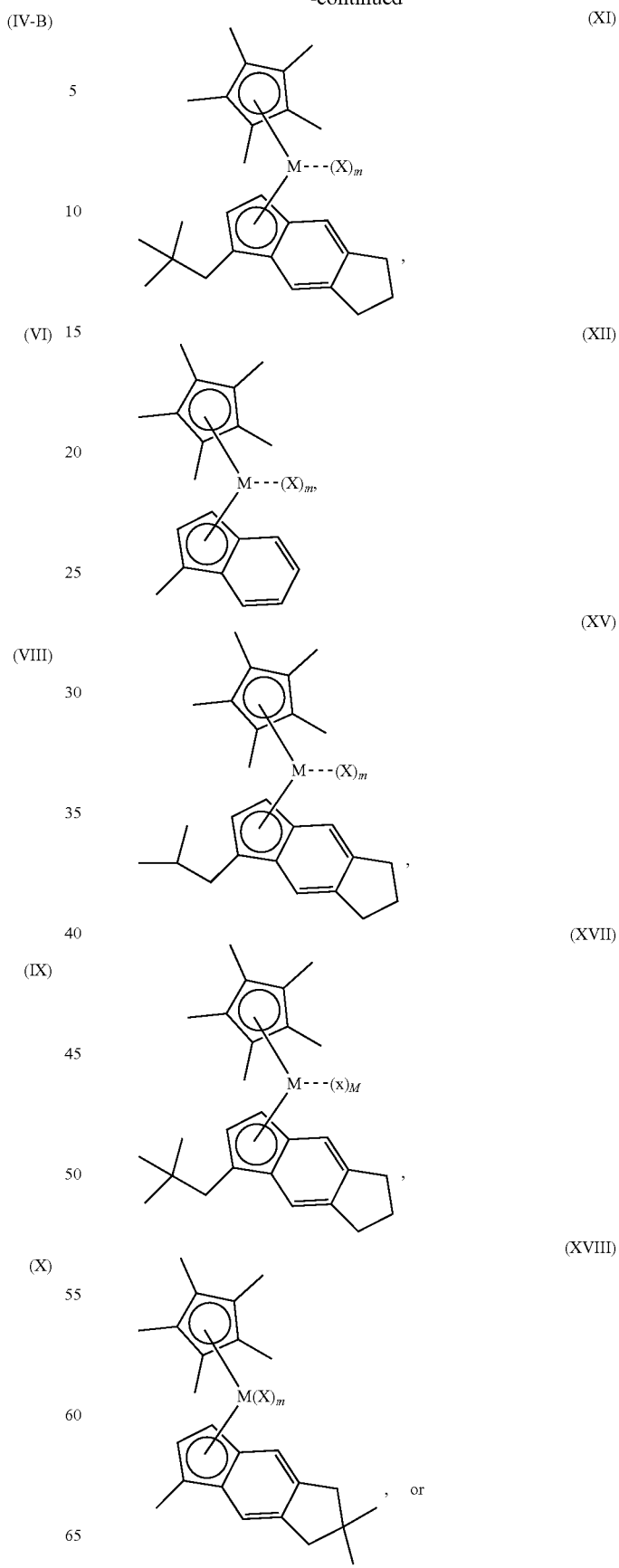

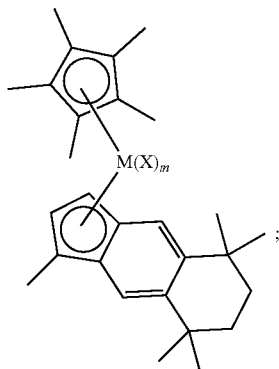

(XIX)

wherein each X is independently a halogen, a hydride, an amide, an alkoxide, a sulfide, a phosphide, a diene, an amine, a phosphine, an ether, or a $C_1$-$C_{20}$ substituted or unsubstituted linear, branched linear, or cyclic hydrocarbyl group, or two or more X moieties may together form a fused ring or ring system;

M is Hf or Zr; and m is 2.

17. The process of paragraph 16 wherein the metallocene is not represented by formula (I-B).

18. The process of any of paragraphs 1 to 17, wherein the polymerization reaction exhibits a selectivity toward a combination of greater than or equal to about 96.5 mol % vinylidenes, from 0.5 mol % to 3.5 mol % tri-substituted vinylenes, less than or equal to about 1.5 mol % di-substituted vinylenes, and less than or equal to about 1.5 mol % vinyls, based on total moles of vinyls, vinylidenes, di-substituted vinylenes, and tri-substituted vinylenes in the unsaturated PAO product.

19. The process of any of paragraphs 1 to 18, wherein the polymerization reaction exhibits a selectivity toward a combination of vinylidenes of equal to or greater than 97.0 mol %, preferably equal to or greater than 97.9 mol %; tri-substituted vinylenes of less than 2.1 mol %; di-substituted vinylenes of 0.5 mol % or less; and vinyls of 1.0 mol % or less, based on total moles of vinyls, vinylidenes, di-substituted vinylenes, and tri-substituted vinylenes in the unsaturated PAO product.

20. The process of any of paragraphs 1 to 19, wherein the polymerization reaction exhibits a selectivity towards a combination of vinylidenes and tri-substituted vinylenes of collectively greater than 98.0 mol %, preferably greater than 98.5 mol %, and a combination of di-substituted vinylenes and vinyls of collectively less than 2.0 mol %, preferably less than 1.5 mol %, based on total moles of vinyls, vinylidenes, di-substituted vinylenes, and tri-substituted vinylenes in the unsaturated PAO product.

21. The process of paragraph 1, wherein the polymerization reaction results in the unsaturated PAO product having a number average molecular weight (Mn) of 1500 g/mol or less, preferably from 300 to 800 g/mol, as measured by $^1$H NMR.

22. The process of any of paragraphs 1 to 21, wherein the catalyst system further comprises a non-coordinating anion type activator, preferably wherein the non-coordinating anion type activator comprises: N,N-dimethylanilinium tetrakis(perfluorophenyl)borate, N,N-dimethylanilinium tetrakis(perfluoronaphthyl)borate, triphenylcarbonium tetrakis(perfluorophenyl)borate, triphenylcarbonium tetrakis(perfluoronaphthyl)borate, N,N-dimethylanilinium tetrakis(perfluorophenyl)aluminate, N,N-dimethylanilinium tetrakis(perfluoronaphthyl)aluminate, or combinations thereof.

23. The process of any of paragraphs 1 to 22, wherein: the polymerization conditions comprise a reaction temperature from 40° C. to 150° C.; an average activity level of at least 1200 g/s·mol; the polymerization reaction mixture exhibits a yield of at least 10%; or a combination thereof.

24. The process of any of paragraphs 1 to 23, further comprising:
a) contacting the unsaturated PAO product with hydrogen to convert at least a portion of the unsaturated PAO product to a hydrogenated PAO product;
b) contacting the unsaturated PAO product with a chemical reagent to convert at least a portion of the unsaturated PAO product to a functionalized PAO product;
or a combination thereof.

25. The process of any of paragraphs 1 to 24, wherein any combination of $C_2$-$C_5$ alpha-olefins are collectively present in the alpha-olefin feed at no higher than 25 mol %, based on the total moles of the alpha-olefins supplied to the polymerization reactor, preferably wherein the alpha-olefin feed is substantially free of ethylene, propylene, $C_4$ alpha-olefins, and $C_5$ alpha-olefins; or a combination thereof.

26. An unsaturated poly alpha-olefin (PAO) product comprising greater than or equal to about 80 mol % vinylidenes, preferably 90 mol % vinylidenes, more preferably 96.5 mol % vinylidenes, based on total moles of vinyls, vinylidenes, di-substituted vinylenes, and tri-substituted vinylenes contained therein and having an Mn of less than 5000 g/mol as determined by $^1$H NMR.

27. An unsaturated poly alpha-olefin (PAO) product comprising:
96.5 mol % to 99.9 mol % of vinylidenes;
0.1 mol % to 3.5 mol % of tri-substituted vinylenes;
3.0 mol % or less of di-substituted vinylenes;
3.0 mol % or less of vinyl groups; based on total moles of vinylidenes, tri-substituted vinylenes, di-substituted vinylenes, and vinylidenes contained therein; and
a number average molecular weight (Mn) of 1500 g/mol or less as measured by $^1$H NMR.

28. An unsaturated poly alpha-olefin (PAO) product comprising greater than or equal to about 80 mol % vinylidenes, preferably 90 mol % vinylidenes, more preferably 96.5 mol % vinylidenes, based on total moles of vinyls, vinylidenes, di-substituted vinylenes, and tri-substituted vinylenes contained therein, and
less than or equal to about 1.0 mol % di-substituted vinylenes, when present;
less than or equal to about 1.0 mol % vinyl groups when present; and
a number average molecular weight (Mn) of 1000 g/mol or less as measured by $^1$H NMR.

29. An unsaturated poly alpha-olefin (PAO) product comprising greater than or equal to about 80 mol % vinylidenes, preferably 90 mol % vinylidenes, more preferably 96.5 mol % vinylidenes, based on total moles of vinyls, vinylidenes, di-substituted vinylenes, and tri-substituted vinylenes contained therein, and from 98 mol % to 99.5 mol % of a combination of vinylidenes and tri-substituted vinylenes; 0.5 mol % to 2 mol % of a combination of di-substituted vinylenes and vinyl groups, and a number average molecular weight (Mn) of 800 g/mol or less as measured by $^1$HNMR.

30. A catalyst compound suitable to produce an unsaturated PAO product from $C_6$-$C_{32}$ alpha-olefin under polymerization conditions, comprising:

a polymerization selectivity suitable to form an unsaturated PAO product comprising:

greater than or equal to about 80 mol % vinylidenes, preferably 90 mol % vinylidenes, more preferably 96.5 mol % vinylidenes, based on total moles of vinyls, vinylidenes, di-substituted vinylenes, and tri-substituted vinylenes in the unsaturated PAO product; represented by the formula (F-MC2):

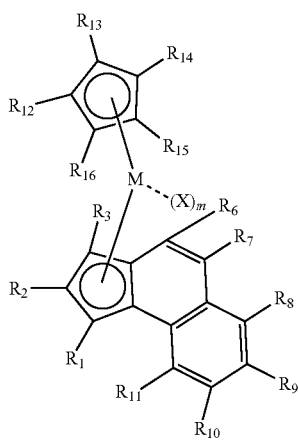

(F-MC2)

in which one of $R^1$, $R^2$, and $R^3$ is an alpha Group 14 atom directly attached to the indenyl ring, and a beta Group 14 atom attached to the alpha atom, and two or more, preferably three, substituted or unsubstituted linear, branched linear, or cyclic $C_1$-$C_8$ hydrocarbyl groups attached to the beta atom, and two of $R^1$, $R^2$, and $R^3$ are each hydrogen;

$R^6$, $R^7$, $R^8$, $R^9$, $R^{10}$, and $R^{11}$ are each independently a hydrogen or a substituted or unsubstituted linear, branched linear, or cyclic $C_1$-$C_{20}$ hydrocarbyl group;

$R^{12}$, $R^{13}$, $R^{14}$, and $R^{15}$ are each independently a hydrogen, or a substituted or unsubstituted linear, branched linear, or cyclic $C_1$-$C_{20}$ hydrocarbyl group;

$R^{16}$ is a hydrogen, a substituted or unsubstituted linear, branched linear, or cyclic $C_1$-$C_{20}$ hydrocarbyl group or silylcarbyl group;

each X is independently a halogen, a hydride, an amide, an alkoxide, a sulfide, a phosphide, a diene, an amine, a phosphine, an ether, or a $C_1$-$C_{20}$ substituted or unsubstituted linear, branched linear, or cyclic hydrocarbyl group, or two or more X moieties together form a fused ring or ring system;

M is a group 3, 4 or 5 transition metal having an integer coordination number of v; and m is an integer equal to v-2.

31. The catalyst compound of paragraph 30, wherein the polymerization selectivity is suitable to form an unsaturated PAO product comprising:

96.5 mol % to 99.9 mol % of vinylidenes;
0.1 mol % to 3.5 mol % of ti-substituted vinylenes;
2.0 mol % or less of di-substituted vinylenes;
2.0 mol % or less of vinyl groups;
based on total moles of vinyls, vinylidenes, di-substituted vinylenes, and tri-substituted vinylenes in the unsaturated PAO product; and a number average molecular weight (Mn) of 1500 g/mol or less as measured by $^1$H NMR.

32. A catalyst compound represented by formula (I), (II), (F-MC2), or (IV):

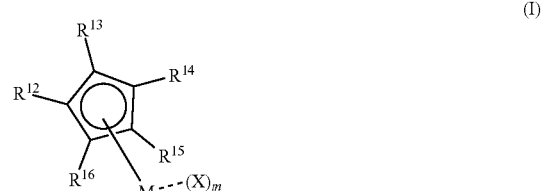

(I)

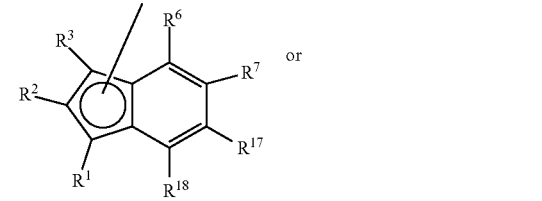

(II)

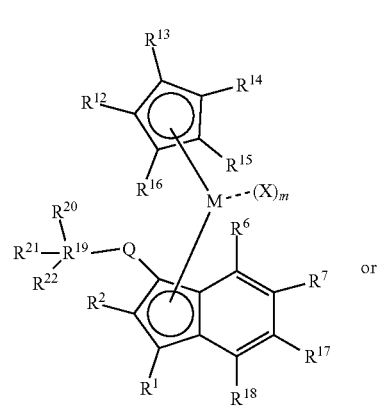

(F-MC2)

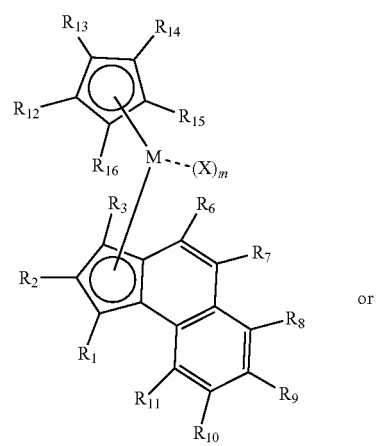

(IV)

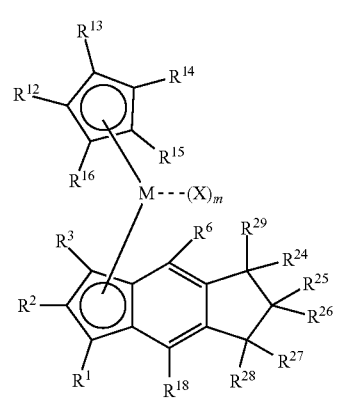

wherein:
i) according to formula (I):
a first one of $R^1$ or $R^3$ is a substituted or unsubstituted linear, branched linear, or cyclic $C_1$-$C_{20}$ hydrocarbyl group;
a second one of $R^1$, $R^2$, and $R^3$ is a hydrogen;
the third one of $R^1$, $R^2$, and $R^3$ is a hydrogen;
$R^6$, $R^7$, $R^{17}$, and $R^{18}$ are each independently hydrogen, a substituted or unsubstituted linear, branched linear, or cyclic $C_1$-$C_{30}$ hydrocarbyl group; and
$R^{12}$, $R^{13}$, $R^{14}$, $R^{15}$, and $R^{16}$ are each independently a substituted or unsubstituted linear, branched linear, or cyclic $C_1$-$C_{20}$ hydrocarbyl group or silylcarbyl group or $R^{16}$ may be a substituted or unsubstituted linear, branched linear, or cyclic $C_1$-$C_{20}$, preferably $C_1$-$C_8$, hydrocarbyl group or silylcarbyl group; or
ii) according to formula (II):
$R^1$ and $R^2$ are hydrogen;
Q and $R^{19}$ comprise Group 14 atoms, preferably C or Si (preferably Q is carbon and $R^{19}$ is carbon or silicon);
$R^{20}$, $R^{21}$, and $R^{22}$ are independently hydrogen or a substituted or unsubstituted linear, branched linear, or cyclic $C_1$-$C_{20}$ hydrocarbyl group, wherein at least two of $R^{20}$, $R^{21}$, and $R^{22}$ are a substituted or unsubstituted linear, branched linear, or cyclic $C_1$-$C_{20}$ hydrocarbyl group;
$R^6$, $R^7$, $R^{17}$, and $R^{18}$ are each independently hydrogen, a substituted or unsubstituted linear, branched linear, or cyclic $C_1$-$C_{30}$ hydrocarbyl group, or two of $R^6$, $R^7$, $R^{17}$, and $R^{18}$ taken together with the carbon atoms in the indenyl ring to which they are directly connected, collectively form one or more substituted or unsubstituted rings annelated to the indenyl ring; and
$R^{12}$, $R^{13}$, $R^{14}$, $R^{15}$, and $R^{16}$ are each independently a substituted or unsubstituted linear, branched linear, or cyclic $C_1$-$C_{20}$ hydrocarbyl group; or
iii) according to formula (F-MC2):
one of $R^1$ and $R^3$ is a substituted or unsubstituted linear, branched linear, or cyclic $C_1$-$C_{20}$ hydrocarbyl group;
two of $R^1$, $R^2$, and $R^3$ are each hydrogen;
$R^6$, $R^7$, $R^8$, $R^9$, $R^{10}$, and $R^{11}$ are each independently hydrogen, a substituted or unsubstituted linear, branched linear, or cyclic $C_1$-$C_{30}$ hydrocarbyl group, or two of $R^6$, $R^7$, $R^8$, $R^9$, $R^{10}$, and $R^{11}$ taken together with the carbon atoms in the benz-indenyl ring to which they are directly connected, collectively form one or more substituted or unsubstituted rings annelated to the benz-indenyl ring; and
$R^{12}$, $R^{13}$, $R^{14}$, $R^{15}$ and $R^{16}$ are each independently a substituted or unsubstituted linear, branched linear, or cyclic $C_1$-$C_{20}$ hydrocarbyl group; or
iv) according to formula (IV):
one of $R^1$ and $R^3$ is a substituted or unsubstituted linear, branched linear, or cyclic $C_1$-$C_{20}$ hydrocarbyl group;
two of $R^1$, $R^2$, and $R^3$ are each hydrogen;
$R^6$, $R^{18}$, $R^{29}$, $R^{24}$, $R^{25}$, $R^{26}$, and $R^{27}$ are each independently hydrogen, a substituted or unsubstituted linear, branched linear, or cyclic $C_1$-$C_{30}$ hydrocarbyl group, or two of $R^6$, $R^{18}$, $R^{29}$, $R^{24}$, $R^{25}$, $R^{26}$, and $R^{27}$ taken together with the carbon atoms in the cyclopentan-indenyl ring to which they are directly connected, collectively form one or more substituted or unsubstituted rings annelated to the cyclopentan-indenyl ring; and
$R^{12}$, $R^{13}$, $R^{14}$, $R^{15}$ and $R^{16}$ are each independently a substituted or unsubstituted linear, branched linear, or cyclic $C_1$-$C_{20}$ hydrocarbyl group;

wherein in the formulae (I), (II), (III), and (IV):
each X is independently a halogen, a hydride, an amide, an alkoxide, a sulfide, a phosphide, a diene, an amine, a phosphine, an ether, a $C_1$-$C_{20}$ substituted or unsubstituted linear, branched linear, or cyclic hydrocarbyl group, or two or more X moieties together form a fused ring or ring system;
M is a group 3, 4 or 5 transition metal having an integer coordination number of v; and
m is an integer equal to v-2.

33. The catalyst compound according to paragraph 31, comprising a polymerization selectivity suitable to form an unsaturated PAO product comprising:
greater than or equal to about 96.5 mol % vinylidenes;
less than or equal to about 3.5 mol % tri-substituted vinylenes;
less than or equal to about 1.0 mol % di-substituted vinylenes, when present;
less than or equal to about 1.0 mol % vinyl groups when present; based on total moles of vinyls, vinylidenes, di-substituted vinylenes, and tri-substituted vinylenes in the unsaturated PAO product; and
a number average molecular weight (Mn) of 1500 g/mol or less as measured by $^1$H NMR.

34. The catalyst compound of paragraph 32, represented by formula (III-B), (IV-B), (VI), (VIII), (IX), (X), (XI), (XII), (XV), (XVII), (XVIII), or (XIX):

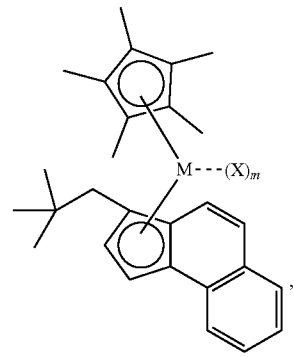

(III-B)

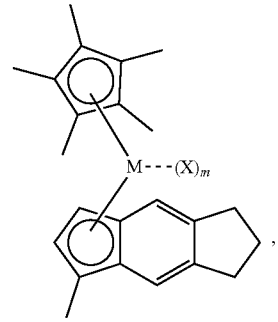

(IV-B)

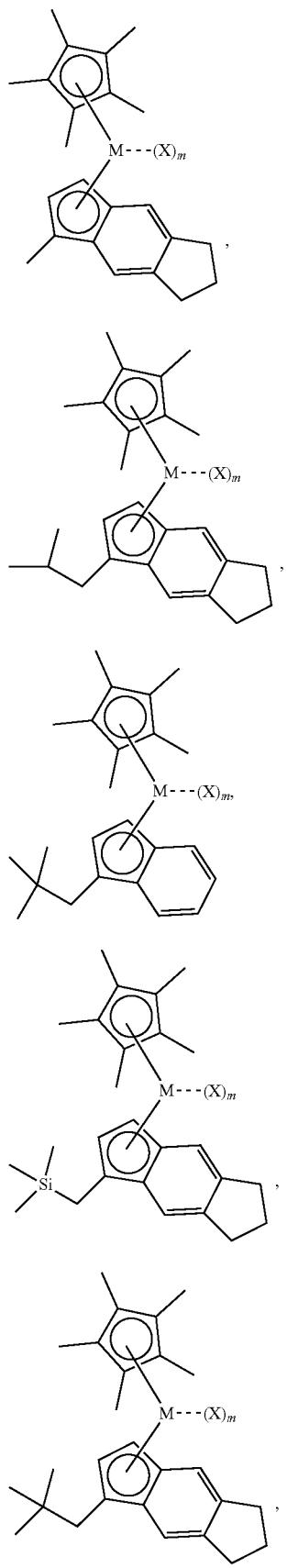
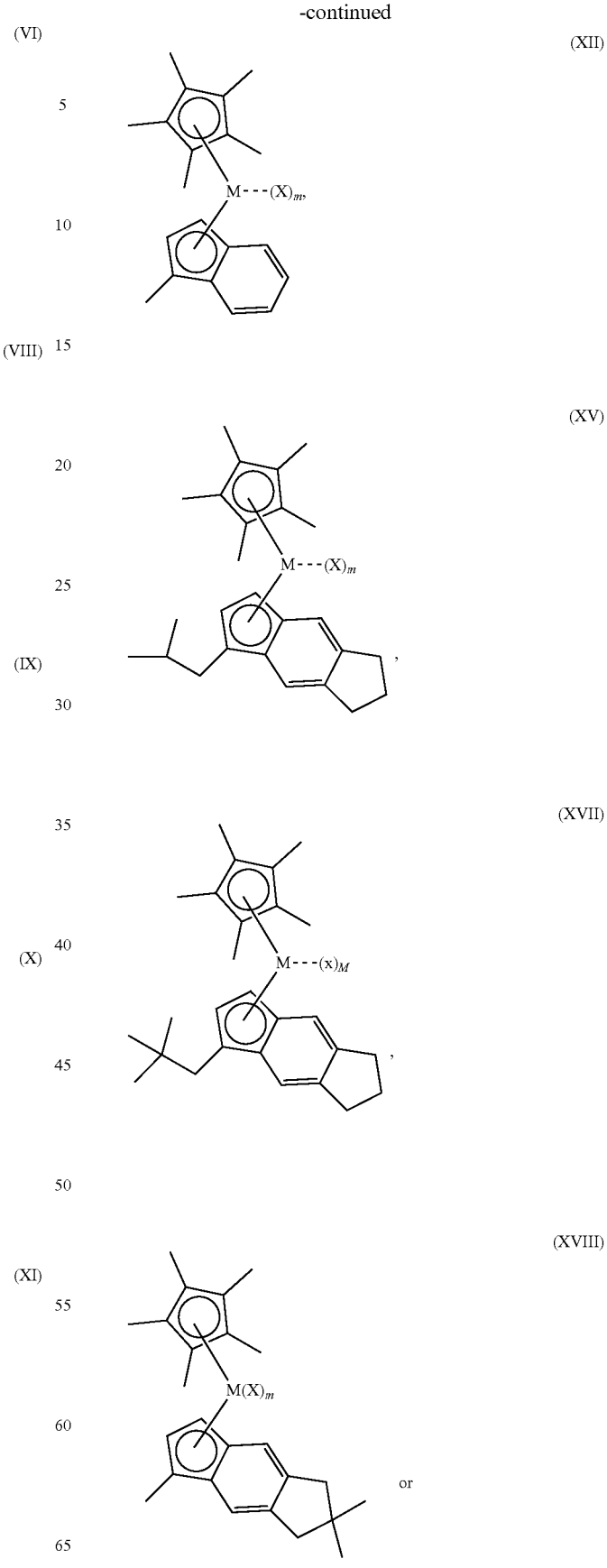

-continued

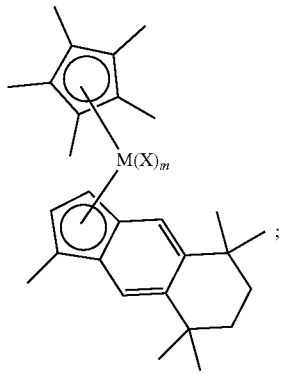

(XIX)

wherein each X is independently a halogen, a hydride, an amide, an alkoxide, a sulfide, a phosphide, a diene, an amine, a phosphine, an ether, or a $C_1$-$C_{20}$ substituted or unsubstituted linear, branched linear, or cyclic hydrocarbyl group, or two or more X moieties may together form a fused ring or ring system;

M is a group 3, 4 or 5 transition metal having an integer coordination number of v; and m is an integer equal to v-2.

Examples

All reactions were done in a nitrogen purged box unless otherwise stated.

Synthesis of Pentamethylcyclopentadienyl(1-methylbenz[e]indenyl) HfMe$_2$ (1A)

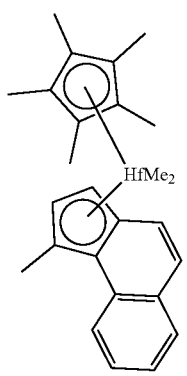

(1A)

To a solution of CeCl$_3$ (12.2 g, 49.4 mmol) in THF (10 ml) was added 1.6M MeLi diethyl ether solution (31 ml, 49.4 mmol). The mixture was stirred at −35° C. for 30 minutes. Then 2,3-dihydro-1H-cyclopenta[a]naphthalen-1-one (6.0 g, 32.9 mmol) in THF (20 ml) was added into the reaction mixture. The color of the reaction mixture changed from yellow to black after stirring for 3 hr. The reaction mixture was allowed to stir at room temperature for 16 h. The reaction was taken out of the nitrogen purged box and quenched with 5 ml of saturated NH$_4$Cl aqueous solution (stirred for 10 min). The solids were precipitated with water and the top clear solution was decanted into a clean beaker. The solids were washed with Et$_2$O. The organic phases were combined and dried with MgSO$_4$. Solvents were then removed under vacuum. The crude product was isolated as a dark oil which was dissolved into 50 ml of CH$_2$Cl$_2$. To the reaction mixture was added catalytic amount of p-toluenesulfonic acid (50 mg). The reaction was stirred at room temperature for 30 min. then washed with saturated NaHCO$_3$ (aq) followed by saturated brine. The organic phase was separated and dried over MgSO$_4$. Solvents were removed and the crude product was purified by column flash chromatograph. Product was eluted out by 10% CH$_2$Cl$_2$ in hexane. Solvents were then removed and 1-methylbenz[e]indene was isolated as white solid (2.7 g).

To the solution of 1-methylbenz[e]indene (2.7 g, 15 mmol) in Et$_2$O (30 ml) was slowly added 11M nBu Li (1.37 ml, 15 mmol). The reaction was stirred at room temperature for 30 min. The lithiated product was slowly crushed out as a white solid. 20 ml of hexane was added, then filtered to collect the product as a white solid (2.7 g). The lithiated product (1.4 g, 7.5 mmol) was mixed with CpMe$_5$HfCl$_3$ (3.15 g, 7.5 mmol) in Et$_2$O (15 ml) and stirred overnight. Et$_2$O was then removed by a stream of nitrogen and the crude product was reslurried into hexane for 15 min. The product was isolated by filtration as a mixture of LiCl and was used for the next step with no further purification.

The crude hafnocene dichloride (4.4 g, 7 mmol) was slurried into toluene (30 ml) and MeMgI (4.9 ml, 3 M in Et$_2$O) was then added and the reaction was stirred at 70° C. for 16 h. The reaction was cooled to room temperature and 1,4-dioxane (2 ml) was added. The mixture was stirred for 15 min and solids were removed by filtration on CELITE and was washed by Et$_2$O. Volatiles were then removed under vacuo. Final product (C$_{26}$H$_{32}$Hf) was isolated as a solid (3.35 g), which was analyzed by $^1$H NMR (CD$_2$Cl$_2$, 400 MHz): δ 8.28 (d, J=8.2 Hz, 1H), 7.70 (dd, J=7.9, 1.6 Hz, 1H), 7.46 (dd, J=8.3, 7.1 Hz, 1H), 7.41-7.30 (m, 2H), 7.00 (d, J=9.0 Hz, 1H), 5.43 (d, J=2.8 Hz, 1H), 5.34 (d, J=2.9 Hz, 1H), 2.45 (s, 3H), 1.82 (s, 15H), −1.19 (s, 3H), −2.23 (s, 3H).

Synthesis of Pentamethylcyclopentadienyl(3-methylbenz[e]indenyl) HfMe$_2$ (B)

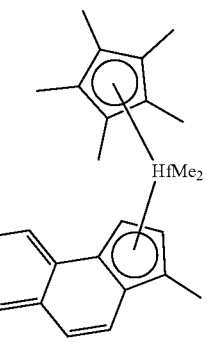

(B)

To a solution of a mixture of 1-methylbenz[e]indenyl Lithium and 3-methylbenz[e]indenyl Lithium (0.46 g, 2.5 mmol, ratio=3:2) in Et$_2$O (15 ml) was added CpMe$_5$HfCl$_3$ (1.05 g, 2.5 mmol). Then it was stirred at room temperature for 16 h. Solids were filtered off and washed by Et$_2$O. The solid that was filtered off was shown to be 90% 1-methylbenz[e]indenyl CpMe$_5$HfCl$_2$ by NMR. Thereafter, Et$_2$O solution was collected and removed. The Crude product was isolated as a white solid and NMR showed that it contained 90% 3-methylbenz[e]indenyl CpMe$_5$HfCl$_2$ and 10% 1-methylbenz[e]indenyl CpMe$_5$HfCl$_2$. This product was reslurried back into a small amount of Et₂O and stirred at 40° C. for 20 min. The solution was slowly cooled back to RT, then to −35° C. and left at −35° C. for 30 min. The solution was then filtered to collect pure 3-methylbenz[e]indenyl CpMe₅HfCl₂ (0.35 g, 0.69 mmol), which was then slurried into toluene (5 ml), MeMgI (0.46 ml, 3 M in Et₂O) was added, and the reaction was stirred at 70° C. for 16 h. The reaction was cooled to room temperature and 1, 4-dioxane was added. The mixture was stirred for 15 min and solids were removed by filtration on CELITE and were washed by Et₂O. Volatiles were then removed under vacuum. The crude product was reslurried into small amount of hexane. Final product ($C_{26}H_{32}Hf$) was isolated by filtration as a solid (0.13 g), which was analyzed by $^1H$ NMR (CD₂Cl₂, 400 MHz): δ 7.79 (d, J=7.7, 1H), 7.69 (d, J=7.9, 1H), 7.58-7.48 (m, 2H), 7.43 (dt, J=22.1, 7.2, 2H), 5.91 (d, J=3.0 Hz, 1H), 5.46 (d, J=2.9 Hz, 1H), 2.25 (s, 3H), 1.89 (s, 15H), −1.04 (s, 3H), −2.43 (s, 3H).

1:1 Mixtures of Pentamethylcyclopentadienyl(1-methylbenz[e]indenyl) HfMe₂ and Pentamethylcyclopentadienyl(3-methylbenz[e]indenyl) HfMe₂ (1A/B=1/1)

The compound was obtained by mixing two pure isomers in 1:1 ratio.

Synthesis of Tetramethylcyclopentadienyl(1-methylbenz[e]indenyl) HfMe₂ (J)

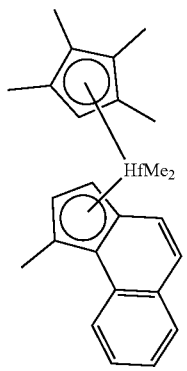

(J)

To a solution of 1-methylbenz[e]indenyl Lithium (0.5 g, 2.7 mmol) in in Et₂O (15 ml) was added CpHMe₄ HfCl₃ (1.09 g, 2.7 mmol). The solution was stirred overnight at room temperature. The dichloride product (1.34 g, 2.3 mmol) was collected by filtration and was washed by Et₂O. It was then slurried into toluene (15 ml). MeMgI (1.5 ml, 3 M in Et₂O) was added and the reaction was stirred at 70° C. for 16 h. The reaction was cooled to room temperature and 1,4-dioxane was added. The mixture was stirred for 15 min and solids were removed by filtration on CELITE and was washed by Et₂O. Volatiles were then removed under vacuum. The crude product was reslurried into small amount of toluene, heated to 70° C. to dissolve the solids, then slowly cooled down to −35° C., and left at −35° C. for 3 h. Pure product recrystallized out of toluene. Final product ($C_{25}H_{30}Hf$) was isolated by filtration as a solid (0.83 g), which was analyzed by 1H NMR (CD₂Cl₂, 400 MHz): δ 8.35 (d, J=8.2 Hz, 1H), 7.81-7.76 (m, 1H), 7.55 (dd, J=8.3, 7.1, 1H), 7.49-7.38 (m, 2H), 7.17 (d, J=9.0 Hz, 1H), 5.74- 5.66 (m, 2H), 5.28 (s, 1H), 2.62 (s, 3H), 1.91 (s, 3H), 1.90 (s, 3H), 1.86 (s, 3H), 1.80 (s, 3H), −1.09 (s, 3H), −1.90 (s, 3H).

Synthesis of Pentamethyleyclopentadienyl(benz[e]indenyl) HfMe₂ (E)

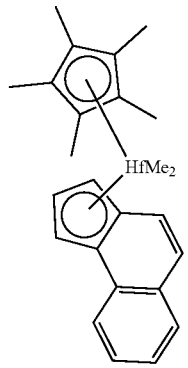

(E)

To a solution of benz[e]indene (8.78 g, 52 mmol) in Et₂O (20 ml) was slowly added 11M nBu Li (4.74 ml, 52 mmol). The reaction was stirred at room temperature for 30 min. Lithiated product slowly precipitated out as a white solid. 20 ml of hexane was added, then filtered to collect the product as a white solid (8.7 g). The lithiated product (0.38 g, 2.19 mmol) and CpMe₅HfCl₃ (0.92 g, 2.19 mmol) were mixed in Et₂O (30 ml) and stirred overnight. The crude product (1.04 g) was isolated by filtration as a mixture with LiCl and was used for the next step with no further purification. The crude hafnocene dichloride (1.04 g, 1.5 mmol) was slurried into toluene (10 ml), MeMgI (1.2 ml, 3 M in Et₂O) was then added, and the reaction was stirred at 70° C. for 16 h. The reaction was cooled to room temperature and 1,4-dioxane was added. The mixture was stirred for 15 min and solids were removed by filtration on CELITE and was washed by Et₂O. Volatiles were then removed under vacuum. Final product ($C_{27}H_{36}Hf$) was isolated as a pale yellow solid (0.85 g), which was analyzed by 1H NMR (CD₂Cl₂, 400 MHz): δ 7.97 (dd, J=8.0, 1.4, 1H), 7.83-7.76 (m, 1H), 7.57-7.34 (m, 4H), 6.46 (ddd, J=3.1, 2.1, 0.9 Hz, 1H), 6.03 (dd, J=3.2, 2.0 Hz, 1H), 5.71 (t, J=3.2 Hz, 1H), 1.90 (s, 15H), −1.52 (s, 3H), −1.69 (s, 3H).

Synthesis of Dimethylsilyl tetramethyleyclopentadienyl(3-benz[e]indenyl) HfMe₂ (K)

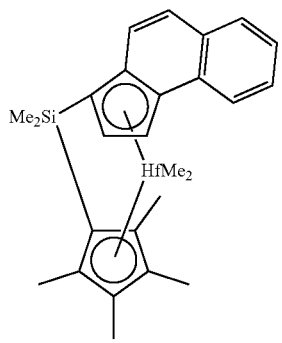

(K)

To a solution of AgOTf (0.6 g, 2 mmol) in toluene (5 ml) was added Me$_2$SiClCpMe$_4$H (0.5 g, 2 mmol). The reaction was stirred for 10 min, and the solids were removed by filtration. The toluene was then removed under vacuum. The product (0.71 g) was isolated as a clear oil and was used for the next step with no further purification. The triflate derivative (0.71 g, 2 mmol) was mixed with benz[e]indenyl lithium (0.37 g, 2 mmol) in Et$_2$O (15 ml) and stirred for 20 min. After the Et$_2$O was removed under vacuo, the crude product was reslurried into hexane and then filtered through a pad of silica gel. The silica gel was washed by hexane followed by 5 ml of Et$_2$O. All solvents were removed under vacuum. Product was isolated as a yellow oil, which was used with no further purification. The yellow oil (0.68 g, 2 mmol) was dissolved into 10 ml of Et$_2$O and 11 M nBu Li (0.37 ml, 4 mmol) was slowly added while the reaction stored at room temperature for 20 min. After addition of 20 ml of hexane, the lithiated product was slowly precipitated out as a white solid which was collected by filtration. The lithiated product (0.78 g, 2 mmol) and HfCl$_4$ (0.53 g, 2 mmol) were then mixed in Et$_2$O (15 ml) and stirred for 2 h. The crude product was collected by filtration and washed by Et$_2$O. The crude product was slurried into dichloromethane (10 ml) and filtered to collect pure product as a yellow solid. Dichloromethane was used to extract the crude product twice. After solvent was removed, 0.25 g dichloride product isolated, which was slurried into toluene (10 ml). MeMgI (0.28 ml, 3 M in Et$_2$O) was then added and the reaction was stirred at 80° C. for 16 h. The reaction was cooled to room temperature and 1, 4-dioxane was added. The mixture was stirred for 15 min and solids were removed by filtration on CELITE and was washed by Et$_2$O. Volatiles were then removed under vacuum. Final product (C$_{26}$H$_{32}$HfSi) was isolated as a pale yellow solid (0.2 g), which was analyzed by 1H NMR (CD$_2$Cl$_2$, 400 MHz): δ 8.24 (d, J=7.8 Hz, 1H), 7.81 (dd, J=7.9, 1.4 Hz, 1H), 7.63-7.58 (m, 2H), 7.50 (ddd, J=8.3, 7.1, 1.3 Hz, 1H), 7.36 (s, 2H), 5.82 (d, J=3.2 Hz, 1H), 1.98 (s, 3H), 1.95 (s, 3H), 1.87 (s, 3H), 1.84 (s, 3H), 1.00 (s, 3H), 0.81 (s, 3H), −0.73 (s, 3H), −2.20 (s, 3H).

Synthesis of n-Butylcyclopentadienyl(1-methylbenz[e]indenyl) ZrMe$_2$ (L)

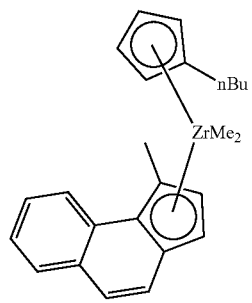

To a solution of 1-methylbenz[e]indenyl Lithium (0.26 g, 1.4 mmol) in Et$_2$O (15 ml) was added n-Butylcyclopentadienyl ZrCl$_3$ (0.46 g, 1.4 mmol). The solution was stirred overnight at room temperature. All solvents were then removed under vacuum. The solids were then slurried in a small amount of toluene. The mixture was heated to 70° C. to allow the solids to dissolve, then slowly cooled to −35° C. and allowed to stand at −35° C. for 2 h. Product (0.35 g) was collected by filtration. The zirconocene dichloride (0.35 g, 0.7 mmol) was slurried into toluene (5 ml), MeMgI (0.46 ml, 3 M in Et$_2$O) was then added, and the reaction was stirred at 70° C. for 16 h. The reaction was cooled to room temperature and sufficient 1,4-dioxane was added. The mixture was stirred for 15 min and solids were removed by filtration on CELITE and was washed by Et$_2$O. Volatiles were then removed under vacuum. Final product (C$_{25}$H$_{30}$Zr) was isolated as an oil (0.18 g), which was analyzed by $^1$H NMR (CD$_2$Cl$_2$, 400 MHz): δ 8.33 (d, J=8.2, 1H), 7.78 (dd, J=7.9, 1.5 Hz, 1H), 7.56 (ddd, J=8.3, 7.1, 1.5 Hz, 1H), 7.46 (ddd, J=7.9, 7.1, 1.3 Hz, 1H), 7.36 (d, J=9.0 Hz, 1H), 7.24 (d, J=9.0 Hz, 1H), 6.09 (q, J=3.2 Hz, 2H), 5.79-5.64 (m, 2H), 5.57 (td, J=2.9, 2.2 Hz, 2H), 2.69 (s, 3H), 2.29 (dd, J=8.5, 6.9 Hz, 2H), 1.53-1.40 (m, 2H), 1.38-1.23 (m, 2H), 0.89 (t, J=7.3 Hz, 3H), −0.70 (s, 3H), −1.17 (s, 3H).

Synthesis of Pentamethyleyclopentadienyl(1-propylbenz[e]indenyl) HfMe$_2$ (C)

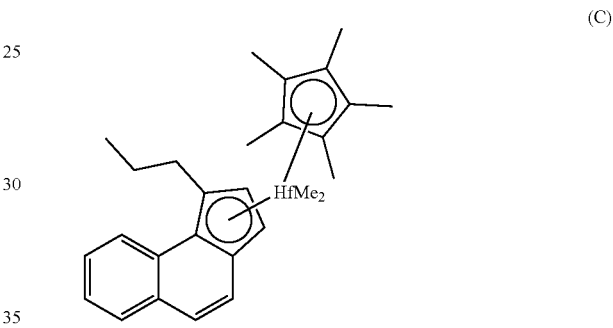

To a solution of mixture of 1-propylbenz[e]indenyl Lithium and 3-propylbenz[e]indenyl Lithium (0.59 g, 2.75 mmol, ratio=2:1) in Et$_2$O (20 ml) was added CpMe5HfCl3 (1.16 g, 2.75 mmol). Then it was stirred at room temperature for 16 h. The solids were filtered off and washed by Et$_2$O. After removal of solvent, the crude product was slurried in hexane (15 ml) and stirred for 30 min. The solid product was collected by filtration and was reslurried into Et$_2$O (30 ml). The solution was heated to 40° C. and cooled to room temperature. The solid product was collected by filtration. $^1$HNMR study showed that the ratio of two isomer was 1:0.07. The solids were then reslurried into 2.5 ml toluene and heated to 70° C. to dissolve the solids, then slowly cooled to −35° C., and allowed to stand −35° C. for 16 h. Pure product (0.3 g) was isolated by filtration. The pure hafnocene dichloride (0.3 g, 0.56 mmol) was slurried into toluene (10 ml), MeMgI (0.37 ml, 3 M in Et$_2$O) was then added, and the reaction was stirred at 70° C. for 16 h. The reaction was cooled to room temperature and 1,4-dioxane (1 ml) was added. The mixture was stirred for 15 min and solids were removed by filtration on CELITE and was washed by Et$_2$O. Volatiles were then removed under vacuum. Final product (C$_{28}$H$_{36}$Hf) was isolated as a solid (0.29 g), which was analyzed by $^1$H NMR (C$_6$D$_6$, 500 MHz): δ 8.49 (d, J=8.2 Hz, 1H), 7.66 (d, J=7.8 Hz, 1H), 7.46-7.36 (m, 2H), 7.27 (dd, J=8.0, 7.0 Hz, 1H), 6.97 (d, J=9.0 Hz, 1H), 5.32 (d, J=2.8 Hz, 1H), 5.25 (d, J=2.9 Hz, 1H), 3.34 (ddd, J=14.6, 9.6, 4.8 Hz, 1H), 2.55 (ddd, J=14.6, 9.7, 6.8 Hz, 1H), 1.83-1.71 (m, 16H), 1.66-1.48 (m, 1H), 0.95 (t, J=7.3 Hz, 3H), −0.62 (s, 3H), −1.70 (s, 3H).

Synthesis of Pentamethyleyclopentadienyl(3-neopentylbenz[e]indenyl) HfMe₂ (2)

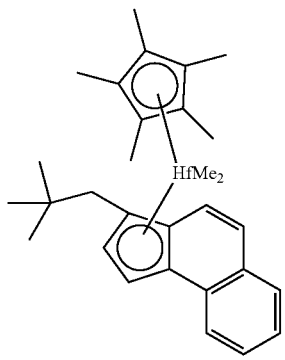

(2)

Benz[e]indenyl lithium (0.50 g, 3 mmol) was mixed with neopentylOMs (0.48 g, 3 mmol) in THF (15 ml) and stirred at 75° C. for 2 days. THF was removed under vacuo and the crude product was reslurried into pentane. The solids were removed by filtration. Then the crude product was eluted on silica gel by 5% DCM in hexane. Relatively pure product was obtained as a clear oil (0.36 g, 2 mmol). To the solution of the clear oil (0.36 g, 2 mmol) in Et₂O (20 ml) was slowly added 11M nBu Li (0.15 ml) and the reaction was stirred at room temperature for 30 min. Et₂O was removed by a stream of nitrogen. The crude lithiated product was reslurried into 1 ml cold pentane, then pentane was immediately pipetted out. Any solvent residue was removed by vacuum. The product (0.33 g, 1 mml) was mixed with CpMe₅HfCl₃ (0.57 g, 1 mmol) in Et₂O (15 ml) and was stirred overnight. LiCl was removed by filtration. Half of Et₂O was then removed under vacuo and pentane was added. 3-substituted hafnium dichloride (0.15 g, 0.24 mmol) was collected by filtration. The dichloride was reslurried into toluene (15 ml). MeMgI (0.16 ml, 3 M in Et₂O) was added and the reaction was stirred at 75° C. for 48 h. The reaction was cooled to room temperature and 1,4-dioxane was added. The mixture was stirred for 15 min and solids were removed by filtration on CELITE and was washed by Et₂O. Volatiles were then removed under vacuo. The product ($C_{30}NH_{40}Hf$) slowly solidifies at −35° C., which was analyzed by ¹H NMR (CD₂Cl₂, 400 MHz): δ 7.83-7.78 (m, 1H), 7.74-7.70 (m, 1H), 7.59 (d, J=0.8 Hz, 1H), 7.51-7.40 (m, 4H), 5.98 (d, J=2.9, 1H), 5.47 (d, J=2.9 Hz, 1H), 2.89 (d, J=14.1 Hz, 1H), 2.26 (s, 1H), 1.90 (s, 15H), 0.95 (s, 9H), −1.02 (s, 3H), −2.41 (s, 3H).

Synthesis of Pentamethyleyclopentadienyl(1-methylindenyl) HfMe₂ (4)

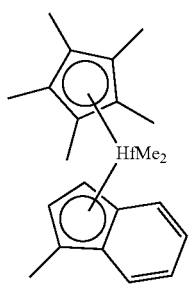

(4)

1-Methylindenyl lithium (0.421 g, 2 mmol) was mixed with CpMe5HfCl3 (0.65 g, 2 mmol) in Et₂O (15 ml) and stirred for 2.5 h. The product was isolated by filtration as a mixture of LiCl and was washed by small amount of Et₂O. It was used for the next step without further purification. The crude hafnium dichloride (0.53 g, 0.95 mmol) was slurried into toluene (20 ml). MeMgI (0.64 ml, 3 M in Et2O) was added and the reaction was stirred at 70° C. for 16 h. The reaction was cooled to room temperature and 1,4-dioxane (0.4 ml) was added. The mixture was stirred for 15 min and solids were removed by filtration on CELITE and was washed by Et₂O. Volatiles were then removed under vacuo. Final product ($C_{22}H_{30}Hf$) was isolated as a solid (0.4 g), which was analyzed by ¹H NMR (CD₂Cl₂, 400 MHz): δ 7.66-7.52 (m, 1H), 7.26-7.07 (m, 3H), 5.45 (dd, J=2.9, 0.8 Hz, 1H), 5.40 (dd, J=2.9, 0.6 Hz, 1H), 2.23 (s, 3H), 1.89 (s, 15H), −1.05 (s, 3H), −2.10 (s, 3H).

Pentamethyleyclopentadienyl(1-methyl-1,5,6,7-tetrahydro-s-indacenyl)HfMe₂ (3) Synthesis

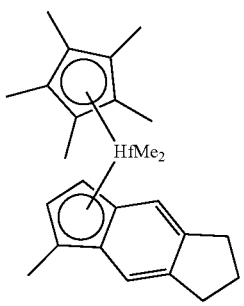

(3)

1-Methyl (1,5,6,7-tetrahydro-s-indacenyl) lithium (0.3 g, 1.6 mmol) was mixed with CpMe₅HfCl₃ (0.7 g, 1.1 mmol) in Et₂O (15 ml) and stir it overnight. Et₂O was then removed by a stream of nitrogen and the crude product was reslurried into pentane for 15 min and was cooled under −35° C. The product was isolated by filtration as a mixture of LiCl and was used for the next step with no further purification. The crude hafnium dichloride (0.78 g, 1.4 mmol) was slurried into toluene (20 ml) and MeMgI (0.94 ml, 3 M in Et₂O) was then added and the reaction was stirred at 70° C. for 16 h. The reaction was cooled to room temperature and 1,4-dioxane was added. The mixture was stirred for 15 min, and the solids were removed by filtration on CELITE and washed by Et₂O. Volatiles were then removed under vacuo. Final product ($C_{25}H_{34}Hf$) was isolated as a solid (0.4 g), which was analyzed by ¹H NMR (CD₂Cl₂, 400 MHz): δ 7.45-7.33 (m, 1H), 7.02-6.92 (m, 1H), 5.32 (dd, J=2.9, 0.9 Hz, 1H), 5.27 (dd, J=2.8, 0.6 Hz, 1H), 2.99-2.86 (m, 4H), 2.19 (s, 3H), 2.11-1.99 (m, 2H), 1.88 (s, 15H), −1.08 (s, 3H), −2.12 (s, 3H).

Synthesis of Pentamethyleyclopentadienyl(1-1,5,6,7-tetrahydro-s-indacenyl)HfMe₂ (5)

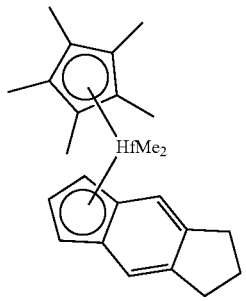

(5)

1,5,6,7-tetrahydro-s-Indacenyl lithium (0.15 g, 0.9 mmol) was mixed with CpMe₅HfCl₃ (0.39 g, 0.9 mmol) in Et₂O (15 ml) and stirred overnight. Et₂O was then removed by a stream of nitrogen and the crude product was reslurried into hexane for 15 min. The product was isolated by filtration as a mixture of LiCl and was used for the next step with no further purification. The crude hafnium dichloride (0.46 g, 0.8 mmol) was slurried into toluene (20 ml), MeMgI (0.57 ml, 3 M in Et₂O) was added and the reaction stirred at 70° C. for 16 h. The reaction was cooled to room temperature and 1,4-dioxane (0.4 ml) was added. The mixture was stirred for 15 min and solids were removed by filtration on CELITE and washed by Et₂O. Volatiles were then removed under vacuo. Final product (C$_{24}$H$_{32}$Hf) was isolated as a solid (0.38 g), which was analyzed by ¹H NMR (CD₂Cl₂, 400 MHz): δ 7.25 (s, 2H), 5.81 (d, J=3.2 Hz, 2H), 5.55 (t, J=3.2 Hz, 1H), 2.94 (t, J=7.3 Hz, 4H), 2.06 (p, J=7.3 Hz, 2H), 1.89 (s, 15H), −1.49 (s, 6H).

Pentamethyleyclopentadienyl(1-methyl-1,5,6,7-tetrahydro-s-indacenyl) ZrMe₂ (6) Synthesis

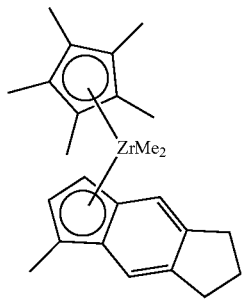

(6)

1-Methyl (1,5,6,7-tetrahydro-s-indacenyl) lithium (0.2 g, 1.1 mmol) was mixed with CpMe₅ZrCl₃ (0.37 g, 1.1 mmol) in Et₂O (15 ml) and stir it overnight. Et₂O was then removed by a stream of nitrogen and the crude product was reslurried into pentane for 15 min. The product was isolated by filtration as a mixture of LiCl and was used for the next step with no further purification.

The crude zirconium dichloride (0.34 g, 0.73 mmol) was slurried into toluene (20 ml), MeMgI (0.48 ml, 3 M in Et2O) was then added, and the reaction was stirred at 70° C. for 16 h. The reaction was cooled to room temperature and 1,4-dioxane (0.4 ml) was added. The mixture was stirred for 15 min and solids were removed by filtration on CELITE and was washed by Et₂O. Volatiles were then removed under vacuo. Final product (C$_{25}$H$_{34}$Zr) was isolated as a solid (0.3 g), which was analyzed by ¹H NMR (CD₂Cl₂, 400 MHz): δ 7.39 (s, 1H), 7.01-6.95 (m, 1H), 5.30 (dd, J=2.9, 0.8 Hz, 1H), 5.26 (dd, J=2.9, 0.6 Hz, 1H), 3.00-2.82 (m, 4H), 2.22 (d, J=0.5 Hz, 3H), 2.04 (p, J=7.4 Hz, 2H), 1.83 (s, 15H), −0.91 (s, 3H), −1.96 (s, 3H).

Synthesis of Pentamethylcyclopentadienyl(1-trimethylsilylmethylbenz[e]indenyl) HfMe₂ (16) and Pentamethylcyclopentadienyl(3-trimethylsilylmethylbenz[e]indenyl) HfMe₂ (7)

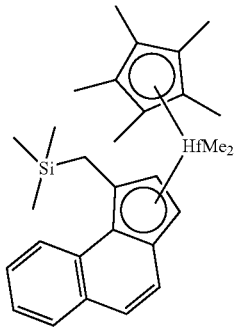

(16)

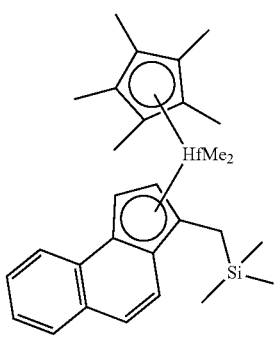

(7)

Benz[e]indenyl lithium (0.3 g, 1.7 mmol) was mixed with TMSCH₂OTf (0.41 g, 1.7 mmol) in THF (8 ml) and stirred at room temperature overnight. THF was removed under vacuo, and the crude product was reslurried into pentane. Solids were removed by filtration. Solvents were removed by a stream of nitrogen. The crude product was isolated as a red oil with a ratio of 1:0.9 1-substituted vs 3-substituted. To the solution of the red oil (0.42 g, 1.7 mmol) in Et₂O (20 ml) was slowly added 11 M nBuLi (1.04 ml). The reaction was stirred at room temperature for 30 min. Et₂O was removed by a stream of nitrogen. The lithiated product was collected as a solid and was used with no further purification. The lithiated product (0.4 g, 2 mmol) was mixed with CpMe₅HfCl₃ (0.65 g, 2 mmol) in Et₂O (15 ml) and stirred for 3 h. The precipitated solid was collected by filtration. The crude Et₂O was saved for 1-substituted product separation. NMR showed that it was the pure 3-substituted product (0.4 g, 0.6 mmol), which was slurried into toluene (6 ml). MeMgI (0.4 ml, 3 M in Et₂O) was then added and the reaction was stirred at 70° C. for 16 h. The reaction was cooled to room temperature and 1,4-dioxane (0.2 ml) was added. The mixture was stirred for 15 min and solids were removed by filtration on CELITE and washed by Et₂O. Volatiles were then removed under vacuo. Pure pentamethylcyclopentadienyl(3-trimethylsilylmethylbenz[e]indenyl)hafnium(IV) dimethyl was isolated as a solid (0.32 g), which was analyzed by ¹H NMR (CD₂Cl₂, 400 MHz): δ 7.80-7.75 (m, 1H), 7.71-7.63 (m, 1H), 7.50-7.30 (m, 4H), 5.87 (d, J=2.9, 1H), 5.27 (d, J=2.8 Hz, 1H), 2.41 (d, J=14.4 Hz, 1H), 1.88 (s, 15H), 1.55 (d, J=14.4 Hz, 1H), -0.02 (s, 9H), -1.03 (s, 3H), -2.45 (s, 3H).

The crude Et₂O solution was allowed to sit at RT for 1 day. Pure 1-substituted product (0.17 g, 0.27 mmol) was slowly crystalized out, and slurried into toluene (6 ml). MeMgI (0.18 ml, 3 M in Et₂O) was then added and the reaction was stirred at 70° C. for 16 h. The reaction was cooled to room temperature and 1,4-dioxane (0.1 ml) was added. The mixture was stirred for 15 min and solids were removed by filtration on CELITE and washed by Et₂O. Volatiles were then removed under vacuo. Pure pentamethylcyclopentadienyl(1-trimethylsilylmethylbenz[e]indenyl)hafnium(IV) dimethyl was isolated as a solid (0.12 g), which was analyzed by ¹H NMR (CD₂Cl₂, 400 MHz): δ 8.42-8.32 (m, 1H), 7.74 (dd, J=7.8, 1.5 Hz, 1H), 7.50 (ddd, J=8.3, 7.1, 1.5 Hz, 1H), 7.45-7.35 (m, 2H), 7.04 (d, J=9.0 Hz, 1H), 5.47 (d, J=2.8 Hz, 1H), 5.23 (d, J=2.8 Hz, 1H), 2.90 (d, J=14.7 Hz, 1H), 1.89 (s, 15H), 1.76 (d, J=14.8 Hz, 1H), -0.06 (s, 9H), -1.04 (s, 3H), -2.22 (s, 3H).

Pentamethylcyclopentadienyl (1-isobutyl-1,5,6,7-tetrahydro-s-indacenyl) HfMe₂ synthesis (8)

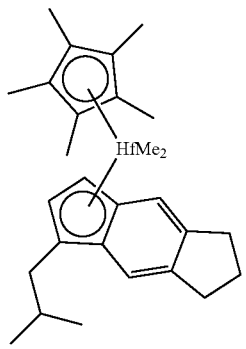

(8)

1-isoButyl-1,5,6,7-tetrahydro-s-indacenyl lithium (0.27 g, 1.2 mmol) was mixed with CpMe₅HfCl₃ (0.52 g, 1.2 mmol) in Et₂O (20 ml) and stirred overnight. Et₂O was then removed by a stream of nitrogen and the crude product was reslurried into pentane for 15 min. The mixture was cooled at -35° C. for 1 h. The product was isolated by filtration as a mixture of LiCl and was used for the next step with no further purification. The crude hafnium dichloride (0.68 g, 1.1 mmol) was slurried into toluene (20 ml) and MeMgI (0.71 ml, 3 M in Et₂O) was then added and the reaction was stirred at 70° C. for 16 h. The reaction was cooled to room temperature and 1,4-dioxane (0.38 ml) was added. The mixture was stirred for 15 min and solids were removed by filtration on CELITE and washed by Et₂O. Volatiles were then removed under vacuo. The product slowly became a solid, to which was added 0.5 ml of pentane. This was swirled and cooled at -35° C. for 3 h, and pentane was pipetted away. Final product (C₂₅H₄₀Hf) was isolated as a solid (0.4 g), which was analyzed by ¹H NMR (CD₂Cl₂, 400 MHz): δ 7.38 (s, 1H), 6.97 (d, J=1.4 Hz, 1H), 5.34 (dd, J=2.9, 0.8 Hz, 1H), 5.27 (d, J=2.9 Hz, 1H), 2.99-2.88 (m, 4H), 2.80 (dd, J=13.5, 5.8 Hz, 1H), 2.04 (p, J=7.3 Hz, 2H), 1.93-1.79 (m, 17H), 0.93 (d, J=6.5 Hz, 3H), 0.85 (d, J=6.4 Hz, 3H), -1.08 (s, 2H), -2.14 (s, 3H).

Synthesis of (neopentyl-indenyl) (pentamethyl-cyclopentadienyl) HfMe₂ (9)

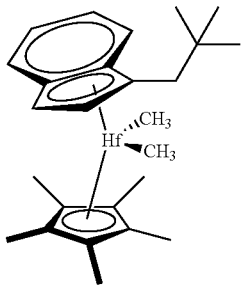

(9)

To a precooled, stirring suspension of (pentamethyl-cyclopentadienyl)hafnium trichloride (0.298 g, 0.709 mmol) in toluene (5 mL), lithium neopentyl-indenide (0.140 g, 0.719 mmol, 1.01 eq) was added with toluene (5 mL). The reaction was stirred at room temperature for 22 h. The reaction was filtered over CELITE. The filtered solid was further extracted with dichloromethane. The dichloromethane and toluene extracts were combined and concentrated under a stream of nitrogen and then under high vacuum to give a pale yellow solid. The solid was stirred in hexane (10 mL) and then filtered. The filtered solid was washed with additional hexane (5 mL). The solid was collected and concentrated under high vacuum to afford the product as an off-white solid (0.296 g, 73%). ¹H NMR (400 MHz, CD₂Cl₂): δ 7.60 (dq, 1H, J=8.4, 1.1 Hz), 7.30 (dt, 1H, J=8.5, 1.1 Hz), 7.24-7.12 (m, 2H), 6.03 (d, 1H, J=2.9 Hz), 5.86 (dd, 1H, J=2.9, 0.8 Hz), 2.99 (d, 1H, J=14.3 Hz), 2.15 (d, 1H, J=14.3 Hz), 2.06 (s, 15H), 0.87 (s, 9H).

To a stirring suspension of (neopentyl-indenyl) (pentamethyl-cyclopentadienyl) hafnium chloride (0.282 g, 0.495 mmol), in toluene (20 mL), methylmagnesium bromide (3.0 M in diethyl ether, 0.33 mL, 0.99 mmol, 2.0 eq) was added. The reaction was heated to 65° C. for 19 h. Then, additional methylmagnesium bromide (3.0 M in diethyl ether, 0.2 mL, 1.2 eq) was added. The reaction was stirred and heated to 65° C. for 1d. The reaction was concentrated under a stream of nitrogen while still hot from the reaction. The reaction was further concentrated under high vacuum. The residue was extracted with hexane (10 mL, then 5 mL) and filtered over CELITE. The combined hexane extracts were concentrated under a stream of nitrogen and then under high vacuum to give an oil, which eventually formed a white solid (0.178 g, 68%). ¹H NMR (400 MHz, C₆D₆): δ 7.64 (dq, 1H, J=8.5, 1.0 Hz), 7.16-7.14 (m, 2H), 7.11-7.06 (m, 1H), 5.35-5.31 (m, 2H), 3.02 (d, 1H, J=14.1 Hz), 2.06 (d, 1H, J=14.1 Hz), 1.76 (s, 15H), 0.95 (s, 9H), -0.58 (s, 3H), -1.57 (s, 3H).

105

Synthesis of (pentamethyl-cyclopentadienyl) ((trimethylsilyl)-methyl-1,5,6,7-tetrahydro-s-indacenyl) HfMe$_2$ (10)

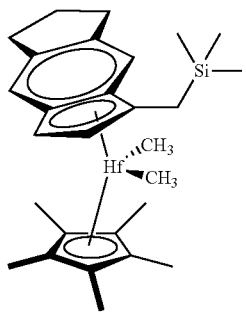

(10)

To a stirring suspension of (pentamethyl-cyclopentadienyl) hafnium trichloride (0.284 g, 0.676 mmol) in toluene (10 mL), lithium (trimethylsilyl)methyl-1,5,6,7-tetrahydro-s-indacenide (0.170 g, 0.684 mmol, 1.01 eq) was added with toluene (5 mL). The reaction was stirred at room temperature for 5 h. The reaction was filtered over CELITE. The filtered solid was further extracted with dichloromethane (2×10 mL). The dichloromethane and toluene extracts were combined and concentrated under a stream of nitrogen and then under high vacuum to give a yellow oil. The oil was stirred in hexane (5 mL), causing a solid to precipitate. The solid was allowed to settle, and the supernatant was discarded. The solid was further washed with hexane (5 mL) and concentrated under high vacuum to afford the product as an off-white solid (0.309 g, 73%). $^1$H NMR (400 MHz, CD$_2$Cl$_2$): δ 7.25 (d, 1H, J=1.8 Hz), 7.04 (d, 1H, J=1.1 Hz), 5.67 (dd, 1H, J=2.8, 0.8 Hz), 5.63 (d, 1H, J=2.8 Hz), 3.06-2.85 (m, 4H), 2.52 (d, 1H, J=14.5 Hz), 2.14-1.95 (m, 2H), 2.03 (s, 15H), 1.78 (d, 1H, J=14.5 Hz), −0.08 (s, 9H).

To a stirring solution of (pentamethyl-cyclopentadienyl) ((trimethylsilyl)-methyl-1,5,6,7-tetrahydro-s-indacenyl) hafnium dichloride (0.309 g, 0.494 mmol) in toluene (20 mL), methylmagnesium bromide (3.0 M in diethyl ether, 0.45 mL, 1.35 mmol, 2.74 eq) was added. The reaction was stirred and heated to 65° C. for 17 h. The reaction was then heated to 80° C. for 1d. Additional methylmagnesium bromide (3.0 M in diethyl ether, 0.45 mL, 1.35 mmol, 2.74 eq) was added, and the reaction was stirred and heated at 80° C. for 16 h. The reaction was concentrated under a stream of nitrogen while still hot from the reaction. The reaction was further concentrated under high vacuum. The residue was extracted with hexane (2×20 mL) and filtered over CELITE. The combined hexane extracts were concentrated under a stream of nitrogen and then under high vacuum to afford the product as an off-white solid (0.208 g, 72%). $^1$H NMR (400 MHz, C$_6$D$_6$): δ 7.43 (s, 1H), 6.99 (d, 1H, J=1.0 Hz), 5.25 (dd, 1H, J=2.8, 0.7 Hz), 5.14 (d, 1H, J=2.8 Hz), 2.99-2.71 (m, 4H), 2.56 (d, 1H, J=14.5 Hz), 1.98-1.72 (m, 2H), 1.80 (s, 15H), 1.68 (d, 1H, J=14.5 Hz), 0.02 (s, 9H), −0.50 (s, 3H), −1.57 (s, 3H).

106

Synthesis of (Neopentyl-1,5,6,7-tetrahydro-s-indacenyl) (pentamethyl-cyclopentadienyl) HfMe$_2$ (11)

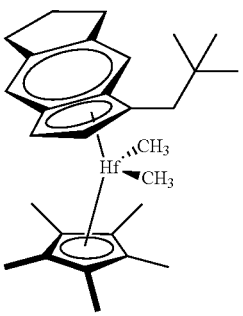

(11)

To a stirring solution of lithium neopentyl-1,5,6,7-tetrahydro-s-indacenide (0.251 g, 1.08 mmol, 1.01 eq) in toluene (5 mL), (pentamethyl-cyclopentadienyl) hafnium trichloride (0.450 g, 1.07 mmol) was added with toluene (10 mL). The reaction was stirred at room temperature for 1d. The reaction was filtered over CELITE. The filtered solid was further extracted with toluene (10 mL) and dichloromethane (10 mL). The dichloromethane and toluene extracts were combined and concentrated under a stream of nitrogen and then under high vacuum at 30° C. to give a pale yellow solid. The solid was washed with hexane (2×5 mL) and concentrated under high vacuum to afford the product as an off-white powder (0.360 g, 55%). $^1$H NMR (400 MHz, CD$_2$Cl$_2$): δ 7.38 (d, 1H, J=0.8 Hz), 7.07 (d, 1H, J=0.9 Hz), 5.88 (d, 1H, J=2.8 Hz), 5.75 (dd, 1H, J=2.8, 0.8 Hz), 3.08-2.85 (m, 5H), 2.16-2.95 (m, 3H), 2.04 (s, 15H), 0.86 (s, 9H).

To a stirring solution of (neopentyl-1,5,6,7-tetrahydro-s-indacenyl) (pentamethyl-cyclopentadienyl) hafnium dichloride (0.360 g, 0.590 mmol) in toluene (20 mL), methylmagnesium bromide (3.0 M in diethyl ether) was added. The reaction was stirred and heated to 80° C. for 2.5 d. The reaction was concentrated under a stream of nitrogen while still hot from the reaction. The reaction was further concentrated under high vacuum. The residue was extracted with hexane (2×20 mL) and filtered over CELITE. The combined hexane extracts were concentrated under a stream of nitrogen and then under high vacuum to afford the product containing hexane (0.14 eq) and toluene (0.05 eq) (0.358 g, 103%). $^1$H NMR (400 MHz, C$_6$D$_6$): δ 7.57 (s, 1H), 7.01 (d, 1H, J=1.2 Hz), 5.31 (dd, 1H, J=2.8, 0.8 Hz), 5.29 (d, 1H, J=2.9 Hz), 3.07 (d, 1H, J=14.0 Hz), 2.99-2.74 (m, 4H), 2.07 (d, 1H, J=14.2 Hz), 1.99-1.81 (m, 2H), 1.79 (s, 15H), 1.00 (s, 9H), −0.53 (s, 3H), −1.57 (s, 3H).

Synthesis of pentamethyleyclopentadienyl(1-methylindenyl) ZrMe₂ (12)

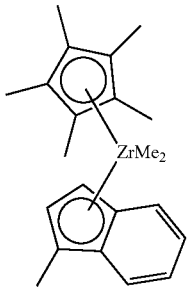

(12)

Pentamethylcyclopentadienyl(1-methylindenyl) ZrMe₂ (12) was synthesized in an analogous fashion of 4 using Me₅CpZrCl₃.

Synthesis of pentamethyleyclopentadienyl(1-1,5,6, 7-tetrahydro-s-indacenyl) ZrMe₂ (13)

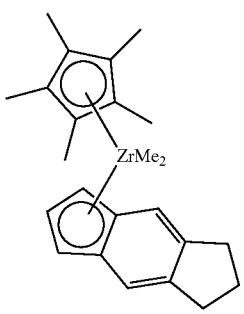

(13)

1,5,6,7-tetrahydro-s-Indacenyl lithium (0.15 g, 0.9 mmol) was mixed with CpMe₅ZrCl₃ (0.31 g, 0.9 mmol) in Et₂O (15 ml) and stirred overnight. Et₂O was then removed by a stream of nitrogen and the crude product was reslurried into hexane for 15 min. The product was isolated by filtration as a mixture of LiCl and was used for the next step with no further purification. The crude zirconocene dichloride (0.34 g, 0.7 mmol) was slurried into toluene (20 ml). MeMgI (0.46 ml, 3 M in Et₂O) was then added and the reaction was stirred at 70° C. for 16 h. The reaction was cooled to room temperature and 1,4-dioxane (0.4 ml) was added. The mixture was stirred for 15 min and solids were removed by filtration on CELITE and washed by Et₂O. Volatiles were then removed under vacuo. Final product ($C_{24}H_{32}Zr$) was isolated as a solid (0.26 g), which was analyzed by ¹H NMR (CD₂Cl₂, 400 MHz): δ 7.27 (s, 2H), 5.86 (d, J=3.2 Hz, 2H), 5.54 (t, J=3.3 Hz, 1H), 2.92 (t, J=7.4 Hz, 4H), 2.06 (p, J=7.3 Hz, 2H), 1.85 (s, 15H), −1.32 (s, 6H).

Synthesis of Pentamethyleyclopentadienyl(2,7-di-tert-butylfluorenyl) HfMe₂ (14)

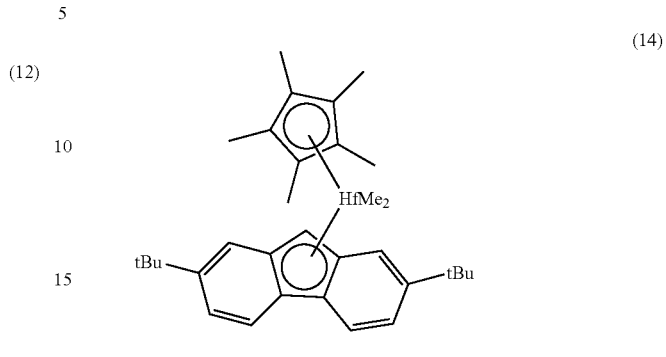

(14)

2,7-di-tert-Butylfluorenyl lithium (0.22 g, 0.7 mmol) was mixed with CpMe₅HfCl₃ (0.28 g, 0.7 mmol) in Et₂O (15 ml) and stir it overnight. Half of Et₂O was then removed by a stream of nitrogen and the crude product was reslurried into pentane for 15 min. The product was isolated by filtration as a mixture of LiCl and was used for the next step with no further purification.

The crude hafnocene dichloride (0.35 g, 0.5 mmol) was slurried into toluene (20 ml). MeMgI (0.33 ml, 3 M in Et₂O) was then added and the reaction was stirred at 70° C. for 16 h. The reaction was cooled to room temperature and 1,4-dioxane (0.4 ml) was added. The mixture was stirred for 15 min and solids were removed by filtration on CELITE and washed by Et₂O. Volatiles were then removed under vacuo. The crude product was dissolved into pentane. Impure solids were removed by filtration on CELITE. Then pentane was removed. The product was isolated as a yellow solid. Final product ($C_{33}H_{46}Hf$) was isolated as a solid (0.26 g), which was analyzed by ¹H NMR (CD₂Cl₂, 400 MHz): δ 7.96 (d, J=8.8 Hz, 2H), 7.52 (dd, J=8.8, 1.7 Hz, 2H), 7.21 (dd, J=1.8, 0.8 Hz, 2H), 5.52 (s, 1H), 1.88 (s, 15H), 1.33 (s, 18H), −2.03 (s, 6H).

Pentamethyleyclopentadienyl(1-isoButyl-1,5,6,7-tetrahydro-s-indacenyl)ZrMe₂ (15) synthesis

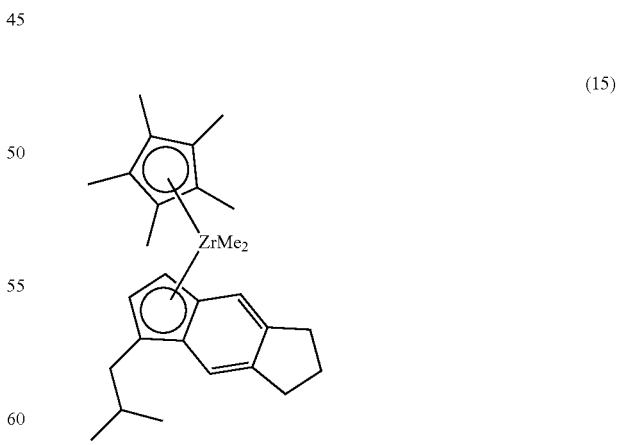

(15)

1-isoButyl-1,5,6,7-tetrahydro-s-indacenyl lithium (0.27 g, 1.2 mmol) was mixed with CpMe₅ZrCl₃ (0.41 g, 1.2 mmol) in Et₂O (20 ml) and stirred overnight. Et₂O was then removed by a stream of nitrogen. The crude product was reslurried into pentane for 15 min and cooled at −35° C. for 1 h. The product was isolated by filtration as a mixture of LiCl and was used for the next step with no further purification.

The crude zirconecene dichloride (0.55 g, 1 mmol) was slurried into toluene (20 ml). MeMgI (0.67 ml, 3 M in Et$_2$O) was added and the reaction was stirred at 70° C. for 16 h. The reaction was cooled to room temperature and 1,4-dioxane (0.35 ml) was added. The mixture was stirred for 15 min and solids were removed by filtration on CELITE and washed by Et$_2$O. Volatiles were then removed under vacuo. The crude product was a dark red oil, to which was added 0.5 ml of pentane. This was swirled and allowed to sit at −35° C. for 3 h. Pentane was pipetted away. Final product (C$_{28}$H$_{40}$Zr) was isolated as colorless crystals (0.3 g), which was analyzed by $^1$H NMR (CD$_2$Cl$_2$, 400 MHz): δ 7.41 (s, 1H), 7.00 (d, J=1.4 Hz, 1H), 5.34 (d, J=2.9, 1H), 5.26 (d, J=2.9 Hz, 1H), 3.04-2.73 (m, 5H), 2.14-1.95 (m, 3H), 1.90-1.80 (m, 16H), 0.96 (d, J=6.6 Hz, 3H), 0.88 (d, J=6.5 Hz, 3H), −0.89 (s, 3H), −1.95 (s, 3H).

Synthesis of (Neopentyl-1,5,6,7-tetrahydro-s-indacenyl) (pentamethyl-cyclopentadienyl) ZrMe$_2$ (17)

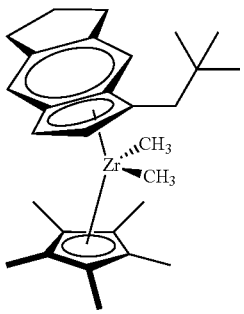

(17)

To a stirring suspension of lithium neopentyl-1,5,6,7-tetrahydro-s-indacenide (0.304 g, 1.309 mmol 1.01 eq) in toluene (30 mL), (pentamethyl-cyclopentadienyl) zirconium trichloride (0.433 g, 1.301 mmol) was added with toluene (20 mL). The reaction was stirred at room temperature for 1 d. The reaction was filtered over CELITE. The filtered solid was further extracted with toluene (10 mL) and dichloromethane (10 mL). The dichloromethane and toluene extracts were combined and concentrated under a stream of nitrogen and then under high vacuum at 30° C. to give a yellow, crystalline solid (0.556 g, 81%). $^1$H NMR (400 MHz, CD$_2$Cl$_2$): δ 7.41 (d, 1H, J=0.9 Hz), 7.09 (d, 1H, J=1.2 Hz), 5.87-5.85 (m, 2H), 3.03-2.84 (m, 5H), 2.17-1.92 (m, 3H), 1.98 (s, 15H), 0.87 (s, 9H).

To a stirring solution of (neopentyl-1,5,6,7-tetrahydro-s-indacenyl) (pentamethyl-cyclopentadienyl) zirconium dichloride (0.556, 1.064 mmol) in toluene (10 mL), MeMgBr (3.0 M in diethyl ether) was added. The reaction was stirred and heated to 80° C. for 2.5 d. The reaction was concentrated under a stream of nitrogen while still hot from the reaction. The reaction was further concentrated under high vacuum. The residue was extracted with hexane (2×10 mL) and filtered over CELITE. The combined hexane extracts were concentrated under a stream of nitrogen and then under high vacuum to afford the product as a white foam (0.440 g, 85%). $^1$H NMR (400 MHz, C$_6$D$_6$): δ 7.58 (d, 1H, J=1.2 Hz), 7.02 (d, 1H, J=1.3 Hz), 5.30 (dd, 1H, J=2.9, 0.7 Hz), 5.26 (d, 1H, J=2.9 Hz), 3.11 (d, 1H, J=14.1 Hz), 2.97-2.73 (m, 4H), 2.14 (d, 1H, J=14.1 Hz), 1.99-1.79 (m, 2H), 1.75 (s, 15H), 1.01 (s, 9H), −0.36 (s, 3H), −1.40 (s, 3H).

Synthesis of (Pentamethylcyclopentadienyl)(3,5,5,8,8-pentamethyl-5,6,7,8-tetrahydro-1H-cyclopenta[b]naphthalenyl)Hafnium(IV) dimethyl (18)

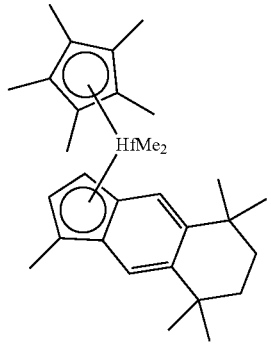

(18)

Mix 3,5,5,8,8-pentamethyl-5,6,7,8-tetrahydro-1H-cyclopenta[b]naphthalenyl Lithium (0.24 g, 1 mmol) with CpMe$_5$HfCl$_3$ (0.41 g, 1 mmol) in Et$_2$O (10 ml) and stir it overnight. Filter off all LiCl. All Et$_2$O was then removed by a stream of nitrogen and the crude product was used for the next step with no further purification. The crude Hafnium dichloride (0.68 g, 1 mmol) was slurried into toluene (15 ml) and MeMgI (0.63 ml, 3 M in Et$_2$O) was then added and the reaction was stirred at 70° C. for 16 hours. The reaction was cooled to room temperature and 1, 4 dioxane was added. The mixture was stirred for 15 min and solids were removed by filtration on celite and was washed by Et$_2$O. All volatiles were then removed under vacuo. The crude product was dissolved into minimum amount of pentane. Let it stay under −35° C. for 2 hr. Pipet out all pentane solution. Final product (C$_{30}$H$_{44}$Hf) was isolated as a solid (0.30 g), which was analyzed by $^1$H NMR (CD$_2$Cl$_2$, 400 MHz): δ 7.51 (s, 1H), 7.13 (s, 1H), 5.29 (q, J=2.8, Hz, 2H), 2.20 (s, 3H), 1.87 (s, 15H), 1.39 (s, 3H), 1.28 (s, 3H), 1.261 (s, 3H), 1.256 (s, 3H), −1.09 (s, 3H), −2.14 (s, 3H).

Synthesis of Pentamethylcyclopentadienyl(2,2,7-trimethyl-1,2,3,5-tetrahydro-s-indacenyl)Hafnium (IV) dimethyl (19)

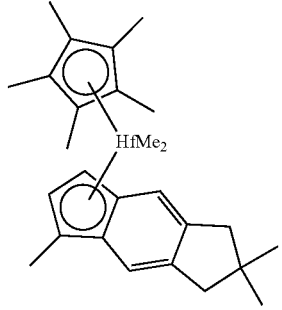

(19)

Mix 2,2,7-trimethyl-1,2,3,5-tetrahydro-s-indacenyl Lithium (0.17 g, 0.8 mmol) with CpMe$_5$HfCl$_3$ (0.34 g, 0.8 mmol) in Et$_2$O (20 ml) and stir it overnight. All Et$_2$O was then removed by a stream of nitrogen and the crude product was reslurried into pentane for 15 min. The product was isolated by filtration as a mixture of LiCl and was used for the next step with no further purification. The crude Hafnium dichloride (0.36 g, 0.6 mmol) was slurried into toluene (15 ml) and MeMgI (0.38 ml, 3 M in Et$_2$O) was then added and the reaction was stirred at 70° C. for 16 hours. The reaction was cooled to room temperature and 1, 4 dioxane was added. The mixture was stirred for 15 min and solids were removed by filtration on celite and was washed by Et$_2$O. All volatiles were then removed under vacuo. Final product (C$_{27}$H$_{38}$Hf) was isolated as a solid (0.29 g), which was analyzed by $^1$H NMR (CD$_2$Cl$_2$, 400 MHz): δ 7.32 (s, 1H), 6.93 (d, J=1.1 Hz, 1H), 5.25 (d, J=2.8 Hz, 2H), 2.76 (d, J=1.5 Hz, 2H), 2.72 (dd, J=4.7, 1.5 Hz, 2H), 2.18 (s, 3H), 1.87 (s, 15H), 1.15 (s, 3H), 1.13 (s, 3H), −1.07 (s, 3H), −2.05 (s Hz, 3H).

Polymerization Examples

Solvents, polymerization grade toluene and/or isohexanes were supplied by ExxonMobil Chemical Co. and were purified by passing through a series of columns: two 500 cc Oxyclear cylinders in series from Labclear (Oakland, Calif.), followed by two 500 cc columns in series packed with dried 3 A molecular sieves (8-12 mesh; Aldrich Chemical Company), and two 500 cc columns in series packed with dried 5 A molecular sieves (8-12 mesh; Aldrich Chemical Company).

1-decene monomer is purchased from Sigma Aldrich and is purified by passing through a basic alumina column and dried over 3A molecular sieves before use. N,N-Dimethylanilinium tetrakis(pentafluorophenyl)borate (BF20) and N,N-dimethylanilinium tetrakisperfluoronaphthylborate were purchased from Albemarle Corporation. All complexes and the activators were added to the reactor as dilute solutions in toluene. The concentrations of the solutions of activator, scavenger, and complexes that were added to the reactor were chosen so that between 40-200 microliters of the solution were added to the reactor to ensure accurate delivery.

Reactor Description and Preparation. Polymerizations were conducted in an inert atmosphere (N2) drybox using autoclaves equipped with an external heater for temperature control, glass inserts (internal volume of reactor=23.5 mL), septum inlets, regulated supply of nitrogen, and equipped with disposable polyether ether ketone mechanical stirrers (800 RPM). The autoclaves were prepared by purging with dry nitrogen at 110° C. or 115° C. for 5 hours and then at 25° C. for 5 hours.

Typical decene polymerizations: The reactor was prepared as described above. Isohexane (enough to bring the total solution volume to 5.0 ml), and 1-decene (2.0 ml) were added via syringe at room temperature and atmospheric pressure. The reactor was then brought to process temperature (60° C., 85° C., or 110° C.). Next, the stirrers where set to 800 RPM and the cells were pressurized to 80 PSI with N2. Scavenger solution (e.g., tri-n-octylaluminum, TNOA) was then added via syringe to the reactor at process conditions. Activator (e.g., BF20) solution was added via syringe to the reactor at process conditions, followed by the pre-catalyst (i.e., MC) solution via syringe to the reactor at process conditions. Reactor temperature was monitored and typically maintained within +/−1° C. Polymerizations were halted by addition of approximately 50 psi 02/Ar (5 mole % O$_2$) gas mixture to the autoclaves for approximately 30 seconds. The polymerizations were quenched after 60 minutes polymerization time. The reactors were cooled and vented. The final PAO was isolated after the solvent, unreacted monomers, and other volatiles were removed in-vacuo. Yields reported include total weight of the non-volatile PAO and residual catalyst. Catalyst activity is reported as grams of PAO per mol transition metal compound per second of reaction time (a/s·mol) and is based on the weight of the isolated PAO.

Characterization of Isolated PAO

The reaction mixture was flashed under vacuum to remove the residual solvent, unreacted monomer and volatile compounds to leave an unsaturated PAO product which is weighed to determine the isolated yield. The unsaturated PAO product was analyzed (as follows) to determine the distributions of vinylidenes ("Vd"), di-substituted vinylenes ("Di"), tri-substituted vinylenes ("Tri"), and vinyls ("Vi"), the catalyst activity level, and physical properties such as number average molecular weight. Conversion percentages of the reactions were calculated from the isolated yield of products and the amount of alpha-olefin used in the reaction. Specifically, conversion=grams isolated PAO/grams alpha-olefin used (when reported in %, conversion=(grams isolated PAO/grams alpha-olefin used)×100).

Proton NMR ($^1$H-NMR) was used to determine the number average molecular weight of the unsaturated PAO and the quantitative breakdown of the olefinic structure types (e.g., vinyl, vinylene, di-substituted vinylene, tri-substituted vinylene, and vinylidene).

Specifically, an NMR instrument of 500 MHz is run under the following conditions: a ~30° flip angle RF pulse, 128 scans, with a relaxation delay of ~5 s between pulses; sample (60-100 mg) dissolved in CDCl$_3$ (deuterated chloroform) in a 5 mm NMR tube; and signal collection temperature at ~25° C. The following approach is taken in determining the concentrations of the various olefins among all of the olefins from an NMR spectrum. First, peaks corresponding to different types of hydrogen atoms in vinyls (T1), vinylidenes (T2), di-substituted vinylenes (T3), and tri-substituted vinylenes (T4) are identified at the peak regions in TABLE A below. Second, areas of each of the above peaks (A1, A2, A3, and A4, respectively) are then integrated. Third, quantities of each type of olefins (Q1, Q2, Q3, and Q4, respectively) in moles are calculated (as A1/2, A2/2, A3/2, and A4, respectively). Fourth, the total quantity of all olefins (Qt) in moles is calculated as the sum total of all four types (Qt=Q1+Q2+Q3+Q4). Finally, the molar concentrations (C1, C2, C3, and C4, respectively, in mol %) of each type of olefin, on the basis of the total molar quantity of all of the olefins, is then calculated (in each case, Ci=100*Qi/Qt).

TABLE A

| Type No. | Olefin Structure | Peak Region (ppm) | Peak Area | Number of Hydrogen Atoms | Quantity of Olefin (mol) | Concentration of Olefin (mol %) |
|---|---|---|---|---|---|---|
| T1 | $CH_2=CH-R^1$ | 4.95-5.10 | A1 | 2 | Q1 = A1/2 | C1 |
| T2 | $CH_2=CR^1R^2$ | 4.65-4.84 | A2 | 2 | Q2 = A2/2 | C2 |
| T3 | $CHR^1=CHR^2$ | 5.31-5.55 | A3 | 2 | Q3 = A3/2 | C3 |
| T4 | $CR^1R^2=CH\,R^3$ | 5.11-5.30 | A4 | 1 | Q4 = A4 | C4 |

The number average molecular weight was determined by:

Mn = Saturated/(vinylene + vinylidene + vinyl + trisubstituted × 2) × 14 + 27 ("Saturated", "vinylene", "vinyl", "trisubstituted" in this equation refer to peak area integration)

1-Decene Polymerizations using N,N-dimethylanilinium tetrakis(perfluorophenyl)borate Activator TABLE I below shows inventive Examples and Comparative Examples 1-36, listing reaction conditions including identity of the metallocene compound (MC), the polymerization temperature, the yield of isolated PAO, the catalyst activity, together with Mn, as measured by $^1$H NMR, and the distributions of the olefins in terms of mole percentages of each type, on the basis of the total moles of the four categories of olefins as determined by $^1$HNMR. Conversion=grams isolated PAO/grams alpha-olefin used (if reported in %, conversion=(grams isolated PAO/grams alpha-olefin used)×100.

Samples having the same catalyst system was repeated at three polymerization temperatures (60° C., 85° C., and 110° C.), with each sample being tested twice at each temperature. The data in TABLE I shows that polymerization using certain inventive metallocene compounds resulted in extraordinarily high selectivity toward vinylidenes (Vd) or toward a combination of vinylidenes and tri-substituted vinylenes (Tri), and in general, a very low selectivity toward di-substituted vinylenes (Di) and toward vinyl (Vi) groups. As such, the uPAO product mixtures from those inventive metallocene compounds may be particularly useful as intermediates for making hydrogenated and/or functionalized PAO materials, where the reactivity of vinylidenes and/ort-substituted vinylenes are particularly high (and therefore desired).

TABLE I

Catalyst 0.08 μmol (0.4 mmol/l in toluene), with 0.08 μmol N,N-Dimethylanilinium Tetrakisperfluorophenylborate (BF20) activator (0.4 mmol/l in toluene), about 0.6 μmol of TNOA (0.01 mol/l in isohexane), 2 mL 1-Decene, isohexane solvent, 1 h.

| Ex. # | | MC | Conditions Temp (° C.) | Activity (g/s · mol) | Olefins Distribution (%) Di | Vi | Tri | Vd | Yield (g) | Mn* (g/mol) | Conv. %** | % Vinylidene (avg) | Mn* (avg) (g/mol) |
|---|---|---|---|---|---|---|---|---|---|---|---|---|---|
| 1 | a | 1A | 60 | 1370 | 0.7 | 3.6 | 2.6 | 93.1 | 0.394 | 1166 | 26.6 | 93.5 | 1153 |
| | b | | 60 | 1420 | 0.5 | 3.4 | 2.3 | 93.8 | 0.409 | 1140 | 27.6 | | |
| 2 | a | 1A | 85 | 2320 | 0.3 | 3.3 | 2.6 | 93.7 | 0.669 | 555 | 45.1 | 93.8 | 538 |
| | b | | 85 | 2050 | 0.4 | 3.1 | 2.7 | 93.8 | 0.589 | 520 | 39.7 | | |
| 3 | a | 1A | 110 | 2810 | 0.2 | 1.0 | 2.9 | 96.0 | 0.809 | 371 | 54.6 | 95.9 | 372 |
| | b | | 110 | 2810 | 0.2 | 1.2 | 2.8 | 95.8 | 0.809 | 372 | 54.6 | | |
| 4 | a | B | 60 | 721 | 0.3 | 4.5 | 3.8 | 91.4 | 0.208 | 1282 | 14.0 | 91.4 | 1285 |
| | b | | 60 | 745 | 0.0 | 4.6 | 4.1 | 91.3 | 0.215 | 1287 | 14.5 | | |
| 5 | a | B | 85 | 1460 | 0.3 | 5.1 | 4.3 | 90.3 | 0.421 | 632 | 28.4 | 89.8 | 636 |
| | b | | 85 | 1470 | 0.4 | 5.5 | 4.8 | 89.3 | 0.424 | 640 | 28.6 | | |
| 6 | a | B | 110 | 2170 | 0.2 | 3.3 | 5.3 | 91.2 | 0.625 | 413 | 42.2 | 91.2 | 415 |
| | b | | 110 | 2250 | 0.2 | 3.4 | 5.4 | 91.1 | 0.649 | 417 | 43.8 | | |
| 7 | a | 1A/B (1:1) | 60 | 1090 | 0.5 | 3.8 | 2.8 | 92.9 | 0.314 | 1203 | 21.2 | 92.6 | 1191 |
| | b | | 60 | 1100 | 0.7 | 3.8 | 3.2 | 92.3 | 0.318 | 1178 | 21.5 | | |
| 8 | a | 1A/B (1:1) | 85 | 1940 | 0.7 | 4.3 | 4.3 | 90.6 | 0.558 | 572 | 37.7 | 91.4 | 581 |
| | b | | 85 | 1900 | 0.4 | 4.2 | 3.3 | 92.1 | 0.547 | 589 | 36.9 | | |
| 9 | a | 1A/B (1:1) | 110 | 2280 | 0.3 | 3.1 | 4.0 | 92.6 | 0.658 | 402 | 44.4 | 93.1 | 405 |
| | b | | 110 | 2680 | 0.2 | 2.5 | 3.8 | 93.5 | 0.772 | 408 | 52.1 | | |
| 10 | a | C | 60 | 555 | — | 2.7 | 2.5 | 94.7 | 0.160 | 967 | 10.8 | 94.5 | 982 |
| | b | | 60 | 651 | — | 3.1 | 2.7 | 94.2 | 0.188 | 996 | 12.7 | | |
| 11 | a | C | 85 | 1440 | — | 3.9 | 3.4 | 92.8 | 0.416 | 535 | 28.1 | 93.5 | 541 |
| | b | | 85 | 1220 | — | 3.1 | 2.7 | 94.2 | 0.351 | 546 | 23.7 | | |
| 12 | a | C | 110 | 2980 | — | 1.6 | 3.0 | 95.5 | 0.860 | 361 | 58.0 | 95.5 | 361 |
| | b | | 110 | 3290 | — | 1.4 | 3.2 | 95.4 | 0.947 | 361 | 63.9 | | |
| 13 | a | D | 60 | 3820 | 0.9 | 23.0 | 3.4 | 72.6 | 1.10 | 3004 | 74.2 | 72.9 | 3039 |
| | b | | 60 | 3830 | 0.9 | 22.9 | 3.0 | 73.2 | 1.10 | 3074 | 74.2 | | |
| 14 | a | D | 85 | 4340 | 1.2 | 12.0 | 4.3 | 82.5 | 1.25 | 987 | 84.3 | 83.3 | 1012 |
| | b | | 85 | 4360 | 0.5 | 12.2 | 3.2 | 84.1 | 1.26 | 1036 | 85.0 | | |

TABLE I-continued

Catalyst 0.08 μmol (0.4 mmol/l in toluene), with 0.08 μmol N,N-Dimethylanilinium Tetrakisperfluorophenylborate (BF20) activator (0.4 mmol/l in toluene), about 0.6 μmol of TNOA (0.01 mol/l in isohexane), 2 mL 1-Decene, isohexane solvent, 1 h.

| | | Conditions | | | Olefins Distribution (%) | | | | Yield | Mn* | % Conv. | % Vinylidene | Mn* |
| | | | Temp | Activity | | | | | | (g/ | | | (avg) |
| Ex. # | MC | | (° C.) | (g/s · mol) | Di | Vi | Tri | Vd | (g) | mol) | %** | (avg) | (g/mol) |
|---|---|---|---|---|---|---|---|---|---|---|---|---|---|
| 15 | a | D | 110 | 4130 | 0.5 | 5.9 | 3.4 | 90.2 | 1.19 | 578 | 80.3 | 90.0 | 577 |
| | b | | 110 | 4140 | 0.5 | 6.5 | 3.2 | 89.8 | 1.19 | 576 | 80.3 | | |
| 16 | a | E | 60 | 4240 | 3.7 | 6.4 | 3.8 | 86.1 | 1.22 | 4550 | 82.3 | 85.3 | 4445 |
| | b | | 60 | 4270 | 3.9 | 6.1 | 5.5 | 84.5 | 1.23 | 4339 | 83.0 | | |
| 17 | a | E | 85 | 4540 | 2.3 | 2.1 | 6.8 | 88.8 | 1.31 | 1285 | 88.4 | 88.8 | 1288 |
| | b | | 85 | 4600 | 2.3 | 1.9 | 7.1 | 88.7 | 1.32 | 1291 | 89.1 | | |
| 18 | a | E | 110 | 4050 | 1.4 | 4.1 | 6.1 | 88.4 | 1.17 | 729 | 78.9 | 87.7 | 723 |
| | b | | 110 | 4050 | 1.8 | 4.3 | 7.0 | 86.9 | 1.17 | 717 | 78.9 | | |
| 19 | a | F$^c$ | 60 | 4370 | 3.3 | — | 7.3 | 89.4 | 1.26 | 1048 | 85.0 | 89.2 | 1044 |
| | b | | 60 | 4350 | 3.4 | — | 7.5 | 89.0 | 1.25 | 1040 | 84.3 | | |
| 20 | a | F$^c$ | 85 | 4380 | 4.1 | — | 11.6 | 84.3 | 1.26 | 551 | 85.0 | 84.3 | 551 |
| | b | | 85 | 4450 | 4.1 | — | 11.6 | 84.2 | 1.28 | 550 | 86.4 | | |
| 21 | a | F$^c$ | 110 | 4230 | 5.7 | — | 16.5 | 77.8 | 1.22 | 402 | 82.3 | 77.8 | 409 |
| | b | | 110 | 4240 | 5.6 | — | 16.8 | 77.7 | 1.22 | 415 | 82.3 | | |
| 22 | a | G$^c$ | 60 | 1600 | 0.8 | 6.0 | 9.8 | 83.3 | 0.462 | 3519 | 31.2 | 83.4 | 3612 |
| | b | | 60 | 1540 | 0.9 | 6.0 | 9.8 | 83.4 | 0.443 | 3704 | 29.9 | | |
| 23 | a | G$^c$ | 85 | 2120 | 1.2 | 8.3 | 12.9 | 77.5 | 0.610 | 1311 | 41.2 | 78.9 | 1321 |
| | b | | 85 | 1990 | 0.5 | 7.6 | 11.6 | 80.2 | 0.572 | 1330 | 38.6 | | |
| 24 | a | G$^c$ | 110 | 1740 | 1.0 | 8.7 | 15.8 | 74.6 | 0.502 | 702 | 33.9 | 74.9 | 702 |
| | b | | 110 | 1520 | 0.9 | 8.6 | 15.4 | 75.1 | 0.438 | 701 | 29.6 | | |
| 25 | a | H$^c$ | 60 | 2480 | — | 33.4 | 19.4 | 47.2 | 0.713 | 6554 | 48.1 | 49.2 | 6863 |
| | b | | 60 | 2590 | — | 33.4 | 15.4 | 51.2 | 0.745 | 7172 | 50.3 | | |
| 26 | a | H$^c$ | 85 | 3050 | 0.7 | 37.5 | 17.2 | 44.6 | 0.880 | 2167 | 59.4 | 44.6 | 2212 |
| | b | | 85 | 2600 | 0.9 | 37.4 | 17.2 | 44.5 | 0.748 | 2256 | 50.5 | | |
| 27 | a | H$^c$ | 110 | 1660 | 0.7 | 30.8 | 17.6 | 50.9 | 0.478 | 953 | 32.3 | 51.3 | 892 |
| | b | | 110 | 2280 | 0.9 | 28.6 | 18.9 | 51.7 | 0.658 | 830 | 44.4 | | |
| 28 | a | J | 60 | 1730 | 1.2 | 1.6 | 12.3 | 84.9 | 0.499 | 2386 | 33.7 | 84.3 | 2372 |
| | b | | 60 | 1740 | 1.4 | 1.9 | 12.9 | 83.7 | 0.502 | 2358 | 33.9 | | |
| 29 | a | J | 85 | 2730 | 1.4 | 2.1 | 16.8 | 79.7 | 0.787 | 867 | 53.1 | 79.9 | 878 |
| | b | | 85 | 2870 | 1.3 | 2.0 | 16.6 | 80.0 | 0.826 | 888 | 55.7 | | |
| 30 | a | J | 110 | 2910 | 1.4 | 1.6 | 20.8 | 76.2 | 0.838 | 509 | 56.5 | 76.3 | 511 |
| | b | | 110 | 2890 | 1.3 | 1.5 | 20.9 | 76.3 | 0.832 | 513 | 56.1 | | |
| 31 | a | K$^c$ | 60 | 4120 | 12.3 | 0.0 | 16.0 | 71.6 | 1.19 | 12368 | 80.3 | 67.6 | 12286 |
| | b | | 60 | 3970 | 15.9 | 0.0 | 20.6 | 63.5 | 1.14 | 12203 | 76.9 | | |
| 32 | a | K$^c$ | 85 | 4570 | 5.5 | 4.3 | 18.2 | 72.1 | 1.32 | 4740 | 89.1 | 72.0 | 4902 |
| | b | | 85 | 4610 | 5.5 | 4.4 | 18.2 | 71.9 | 1.33 | 5064 | 89.7 | | |
| 33 | a | K$^c$ | 110 | 3830 | 4.3 | 11.3 | 17.3 | 67.1 | 1.10 | 3020 | 74.2 | 66.5 | 3007 |
| | b | | 110 | 3710 | 4.4 | 11.4 | 18.4 | 65.8 | 1.07 | 2993 | 72.2 | | |
| 34 | a | L | 60 | 485 | 9.6 | — | 12.5 | 77.9 | 0.140 | 1930 | 9.4 | 78.2 | 1959 |
| | b | | 60 | 486 | 9.8 | — | 11.8 | 78.4 | 0.140 | 1988 | 9.4 | | |
| 35 | a | L | 85 | 815 | 8.1 | 0.4 | 12.1 | 79.4 | 0.235 | 864 | 15.9 | 79.1 | 863 |
| | b | | 85 | 887 | 8.3 | 0.6 | 12.4 | 78.7 | 0.256 | 861 | 17.3 | | |
| 36 | a | L | 110 | 1330 | 8.9 | 0.4 | 14.2 | 76.5 | 0.383 | 534 | 25.8 | 75.8 | 525 |
| | b | | 110 | 1310 | 9.4 | 0.5 | 15.0 | 75.1 | 0.377 | 515 | 25.4 | | |

*Mn estimated by $^1$H NMR;

**Conv. % calculated from isolated yield and it is the minimum conversion due to volatility of the dimer product;

$^c$Comparative catalysts and polymerization examples.

Metallocene compounds used in the polymerization processes of Examples 1-36, have structures as follows:
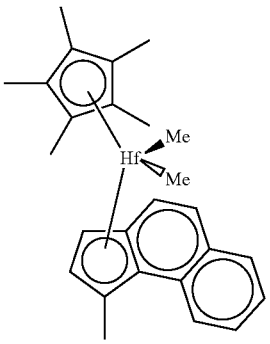
1A
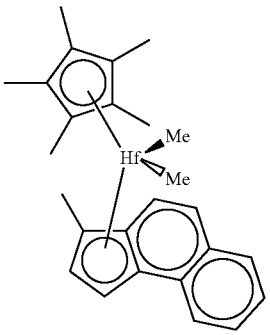
B
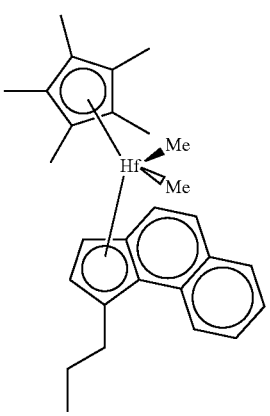
C
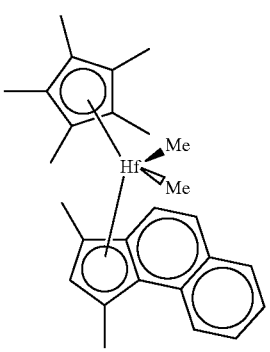
D
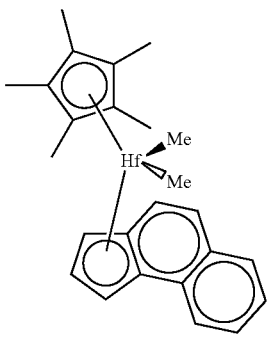
E
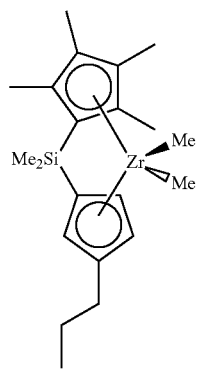
F (comparative)
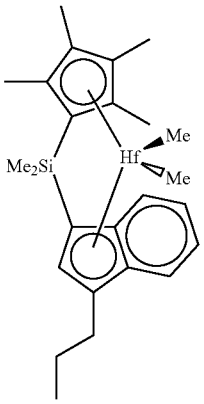
G (comparative)
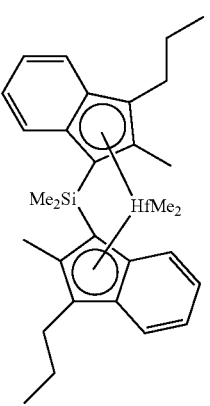
H (comparative)

J

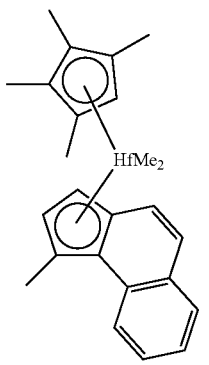

K (comparative)

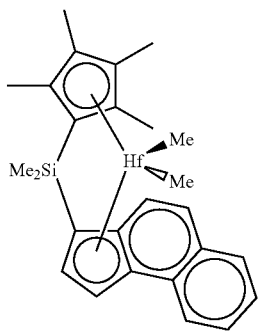

L

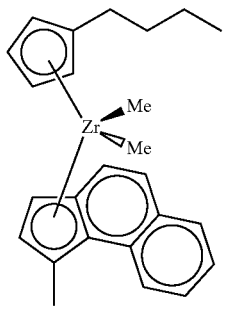

1-Decene Polymerizations using N,N-dimethylanilinium tetrakisperfluoronaphthylborate Activator TABLE II below shows Examples 37-42, using N,N-dimethylanilinium tetrakisperfluoronaphthylborate as an activator, listing reaction conditions including identity of the metallocene compound (MC), the polymerization temperature, the yield of isolated PAO, the catalyst activity, together with Mn, as measured by $^1$H NMR, and the distributions of the olefins in terms of mole percentages of each type, on the basis of the total moles of the four categories of olefins.

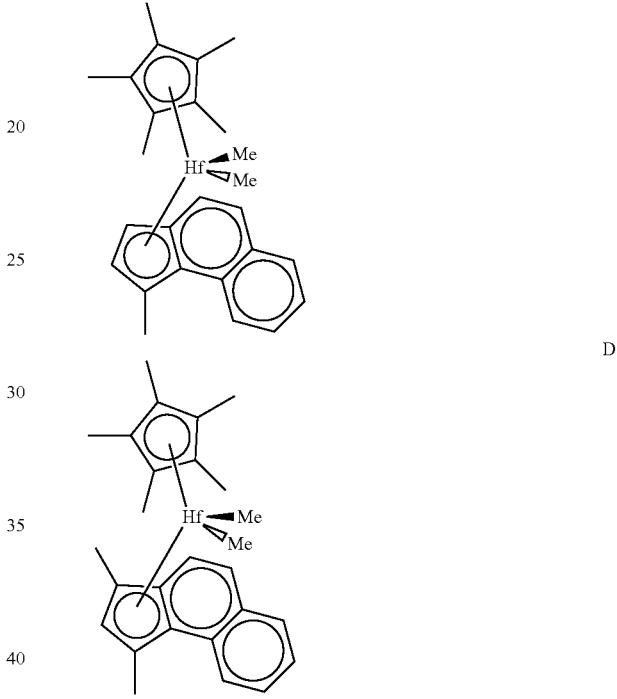

1A

D

TABLE II

Catalyst 0.08 μmol (0.4 mmol/l in toluene), with 0.08 μmol N,N-Dimethylanilinium tetrakisperfluoronaphthylborate activator (0.4 mmol/l in toluene), about 0.6 μmol of TNOA (0.01 mol/l in isohexane), 2 mL 1-Decene, isohexane solvent, 1 h.

| | | Conditions | | | Olefins Distribution (%) | | | | Yield | Mn* | Conv. |
|---|---|---|---|---|---|---|---|---|---|---|---|
| Ex. # | MC | | Temp (° C.) | Activity (g/s · mol) | Di | Vi | Tri | Vd | (g) | (g/mol) | %** |
| 37 | a | 1A | 60 | 696 | 1.2 | 7.3 | 8.8 | 82.7 | 0.200 | 1885 | 13.5 |
| | b | | 60 | 663 | 1.1 | 7.2 | 8.6 | 83.2 | 0.191 | 2009 | 12.9 |
| 38 | a | 1A | 85 | 1350 | 0.9 | 7.6 | 7.6 | 83.8 | 0.388 | 772 | 26.2 |
| | b | | 85 | 1280 | 0.6 | 7.4 | 7.4 | 84.6 | 0.369 | 796 | 24.9 |
| 39 | a | 1A | 110 | 2050 | 0.4 | 5.5 | 6.6 | 87.5 | 0.590 | 456 | 39.8 |
| | b | | 110 | 2340 | 0.4 | 5.2 | 6.7 | 87.7 | 0.674 | 460 | 45.5 |
| 40 | a | D | 60 | 2600 | 1.0 | 34.7 | 8.7 | 55.6 | 0.750 | 4353 | 50.6 |
| | b | | 60 | 2500 | 1.7 | 33.2 | 10.3 | 54.8 | 0.719 | 4353 | 48.5 |
| 41 | a | D | 85 | 3280 | 1.0 | 31.9 | 6.4 | 60.7 | 0.946 | 1405 | 63.8 |
| | b | | 85 | 3480 | 0.9 | 30.8 | 7.4 | 60.9 | 1.00 | 1349 | 67.5 |
| 42 | a | D | 110 | 3850 | 1.0 | 19.3 | 5.8 | 73.9 | 1.11 | 657 | 74.9 |
| | b | | 110 | 3690 | 0.7 | 21.8 | 6.6 | 71.0 | 1.06 | 669 | 71.5 |

*Mn estimated by $^1$H NMR.
**Conv. % calculated from isolated yield and it is the minimum conversion due to volatility of the dimer product.

1-Decene Polymerizations using N,N-dimethylanilinium tetrakis(perfluorophenyl)borate Activator TABLE 3 below compares metallocene catalysts 1A, 2, 3, and 4, and TABLE 4 compares metallocene catalysts 5 through 17 listing reaction conditions including identity of the metallocene compound (MC), the polymerization temperature, the isolated yield of PAO, together with Mn, as measured by $^1$H NMR, and the distributions of the olefins in terms of mole percentages of each type, on the basis of the total moles of the four categories of olefins. Conversion (%)=(grams isolated PAO/grams alpha-olefin used)×100.

Samples of each catalyst system were repeated at three polymerization temperatures (60° C., 85° C., and 110° C.), with each sample being test twice at each temperature. Data in the tables show that polymerization using certain inventive metallocene compounds resulted in extraordinarily high selectivity toward vinylidenes or toward a combination of vinylidenes and tri-substituted vinylenes, and in general, a very low selectivity toward di-substituted vinylenes and toward vinyl groups. As such, the uPAO product mixtures from those inventive metallocene compounds may be particularly useful as intermediates for making hydrogenated and/or functionalized PAO materials, where the reactivity of vinylidenes and/or tri-substituted vinylenes are particularly high (and therefore desired).

Metallocene Catalysts

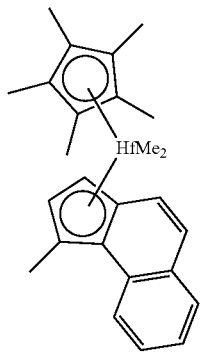

1A

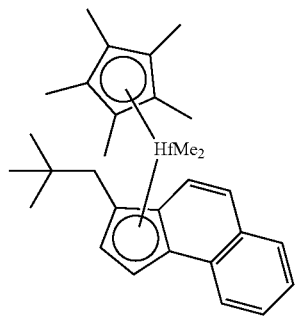

2

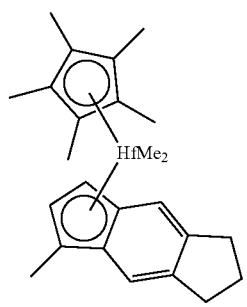

3

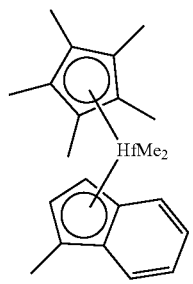

4

TABLE 3

Catalyst 0.08 µmol (0.4 mmol/l in toluene), with 0.08 µmol N,N-Dimethylanilinium Tetrakisperfluorophenylborate (BF20) activator (0.4 mmol/l in toluene), about 0.6 µmol of TNOA (0.01 mol/l in isohexane), 2 mL 1-Decene, isohexane solvent, 1 h.

| EX | T (° C.) | MC | Iso-lated Yield (g) | % Vinylene | % Tri-sub | % Vinyl | % Vinylidene | Mn* g/mol | % Vinylidene (avg) | Mn* (avg) (g/mol) | Conv %** |
|---|---|---|---|---|---|---|---|---|---|---|---|
| 43A | 60 | 1A | 0.3942 | 0.7 | 2.6 | 3.6 | 93.1 | 1166 | 93.5 | 1153 | 26.6 |
| 43B | 60 | 1A | 0.4087 | 0.5 | 2.3 | 3.4 | 93.8 | 1140 | | | 27.6 |
| 44A | 85 | 1A | 0.6694 | 0.3 | 2.6 | 3.3 | 93.7 | 555 | 93.8 | 537 | 45.2 |
| 44B | 85 | 1A | 0.5894 | 0.4 | 2.7 | 3.1 | 93.8 | 520 | | | 39.8 |
| 45A | 110 | 1A | 0.8086 | 0.2 | 2.9 | 1.0 | 95.9 | 371 | 95.9 | 372 | 54.6 |
| 45B | 110 | 1A | 0.8092 | 0.2 | 2.8 | 1.2 | 95.8 | 372 | | | 54.6 |
| 46A | 60 | 2 | 0.1097 | 0.4 | 1.1 | 0.8 | 97.8 | 504 | 97.9 | 519 | 7.4 |
| 46B | 60 | 2 | 0.1064 | 0.4 | 1.0 | 0.7 | 97.9 | 533 | | | 7.2 |
| 47A | 85 | 2 | 0.194 | 0.1 | 0.8 | 0.1 | 99.0 | 324 | 99.0 | 325 | 13.1 |
| 47B | 85 | 2 | 0.1762 | 0.1 | 0.8 | 0.2 | 98.9 | 327 | | | 11.9 |
| 48A | 110 | 2 | 0.3025 | 0.2 | 1.3 | 0.2 | 98.3 | 303 | 98.5 | 303 | 20.4 |
| 48B | 110 | 2 | 0.2614 | 0.1 | 1.1 | 0.1 | 98.7 | 303 | | | 17.6 |
| 49A | 60 | 3 | 0.1548 | 0.3 | 0.7 | 0.9 | 98.1 | 622 | 97.7 | 620 | 10.4 |
| 49B | 60 | 3 | 0.1594 | 0.4 | 1.1 | 1.3 | 97.2 | 618 | | | 10.8 |
| 50A | 85 | 3 | 0.4458 | 0.8 | 2.1 | 1.2 | 95.9 | 367 | 97.0 | 373 | 30.1 |
| 50B | 85 | 3 | 0.4442 | 0.2 | 0.9 | 0.7 | 98.2 | 379 | | | 30.0 |

TABLE 3-continued

Catalyst 0.08 µmol (0.4 mmol/l in toluene), with 0.08 µmol N,N-Dimethylanilinium Tetrakisperfluorophenylborate (BF20) activator (0.4 mmol/l in toluene), about 0.6 µmol of TNOA (0.01 mol/l in isohexane), 2 mL 1-Decene, isohexane solvent, 1 h.

| EX | T (° C.) | MC | Iso-lated Yield (g) | % Vinylene | % Tri-sub | % Vinyl | % Vinylidene | Mn* g/mol | % Vinylidene (avg) | Mn* (avg) (g/mol) | Conv %** |
|---|---|---|---|---|---|---|---|---|---|---|---|
| 51A | 110 | 3 | 0.8584 | 0.1 | 1.3 | 0.2 | 98.4 | 320 | 98.1 | 317 | 57.9 |
| 51B | 110 | 3 | 0.8568 | 0.3 | 1.6 | 0.4 | 97.7 | 315 | | | 57.8 |
| 52A | 60 | 4 | 0.1827 | 0.3 | 3.1 | 4.7 | 91.9 | 1313 | 91.9 | 1298 | 12.3 |
| 52B | 60 | 4 | 0.1844 | 0.3 | 3.2 | 4.6 | 91.9 | 1284 | | | 12.4 |
| 53A | 85 | 4 | 0.7312 | 0.1 | 3.5 | 6.7 | 89.8 | 722 | 89.5 | 710 | 49.3 |
| 53B | 85 | 4 | 0.5846 | 0.2 | 4.0 | 6.6 | 89.2 | 699 | | | 39.4 |
| 54A | 110 | 4 | 0.8993 | 0.3 | 4.7 | 5.8 | 89.2 | 426 | 89.8 | 430 | 60.7 |
| 54B | 110 | 4 | 0.9406 | 0.2 | 4.0 | 5.4 | 90.4 | 435 | | | 63.5 |

*Mn estimated by $^1$H NMR,
**Conv % calculated from isolated yield and it is the minimum conversion due to volatility of the dimer product.

Catalysts numbered 5 through 17 were prepared as described above. Polymerization conditions utilized 0.08 µmol of the indicated catalyst with the N,N-Dimethylanilinium Tetrakisperfluorophenylborate activator, 2 mL 1-decene, isohexane solvent and a 1 h reaction time at the indicated temperature. These data are shown in Table 4.

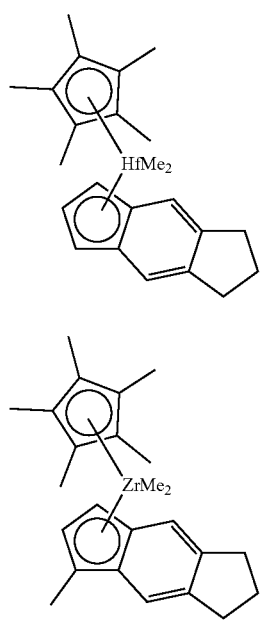

5

6

7

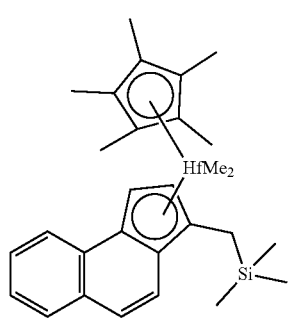

-continued

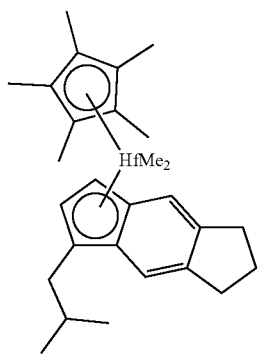

8

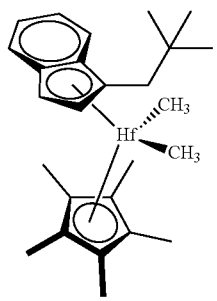

9

10

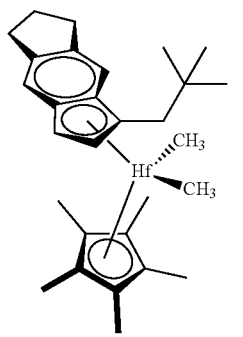
11
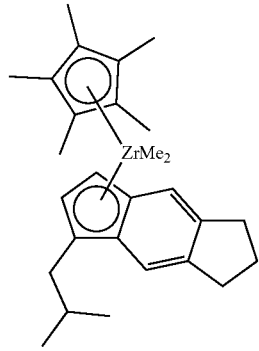
15
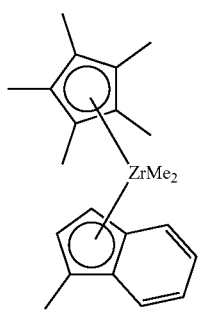
12
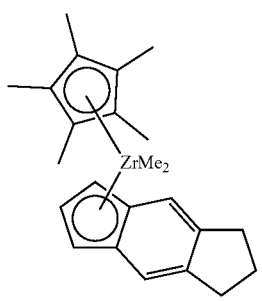
13
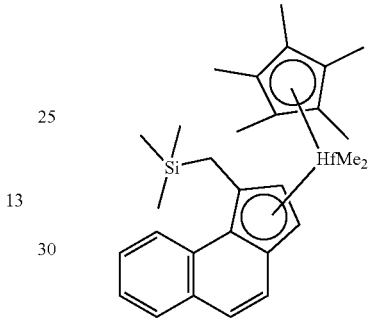
16
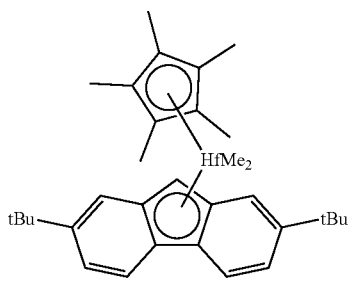
14
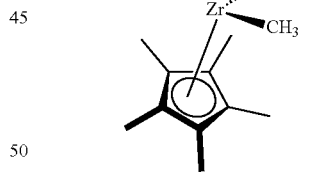
17
TABLE 4
Catalyst 0.08 μmol (0.4 mmol/l in toluene), with 0.08 μmol N,N-Dimethylanilinium Tetrakisperfluorophenylborate (BF20) activator (0.4 mmol/l in toluene), about 0.6 μmol of TNOA (0.01 mol/l in isohexane), 2 mL 1-Decene, isohexane solvent, 1 h.
| EX | T (° C.) | MC | Isolated Yield (g) | % Vinylene | % Tri-sub | % Vinyl | % Vinylidene | Mn* g/mol | % Vinylidene (avg) | Mn* (avg) (g/mol) | Conv %** |
|---|---|---|---|---|---|---|---|---|---|---|---|
| 55A | 60 | 5 | 1.2132 | 1.5 | 5.7 | 2.4 | 90.4 | 2552 | 90.4 | 2592 | 81.9 |
| 55B | 60 | 5 | 1.1997 | 1.5 | 5.7 | 2.4 | 90.4 | 2632 | | | 81.0 |
| 56A | 85 | 5 | 1.2801 | 1.2 | 8.9 | 1.2 | 88.8 | 914 | 88.7 | 917 | 86.4 |
| 56B | 85 | 5 | 1.2557 | 1.2 | 9.1 | 1.1 | 88.6 | 921 | | | 84.7 |
| 57A | 110 | 5 | 1.1828 | 1.1 | 11.4 | 1.0 | 86.5 | 534 | 86.1 | 536 | 79.8 |
| 57B | 110 | 5 | 1.2055 | 1.2 | 12.1 | 1.0 | 85.7 | 538 | | | 81.3 |
| 58A | 60 | 6 | 0.0278 | 0.6 | 0.6 | 0.3 | 98.5 | 552 | 98.1 | 551 | 1.9 |

TABLE 4-continued

Catalyst 0.08 µmol (0.4 mmol/l in toluene), with 0.08 µmol N,N-Dimethylanilinium Tetrakisperfluorophenylborate (BF20) activator (0.4 mmol/l in toluene), about 0.6 µmol of TNOA (0.01 mol/l in isohexane), 2 mL 1-Decene, isohexane solvent, 1 h.

| EX | T (° C.) | MC | Isolated Yield (g) | % Vinylene | % Tri-sub | % Vinyl | % Vinylidene | Mn* g/mol | % Vinylidene (avg) | Mn* (avg) (g/mol) | Conv %** |
|---|---|---|---|---|---|---|---|---|---|---|---|
| 58B | 60 | 6 | 0.0285 | 0.6 | 1.1 | 0.6 | 97.6 | 549 | | | 1.9 |
| 59A | 85 | 6 | 0.1436 | 0.4 | 1.0 | 0.4 | 98.2 | 356 | 98.1 | 353 | 9.7 |
| 59B | 85 | 6 | 0.1477 | 0.4 | 1.1 | 0.4 | 98.1 | 351 | | | 10.0 |
| 60A | 110 | 6 | 0.3657 | 0.5 | 1.5 | 0.3 | 97.8 | 314 | 98.1 | 314 | 24.7 |
| 60B | 110 | 6 | 0.3488 | 0.2 | 1.1 | 0.2 | 98.4 | 315 | | | 23.5 |
| 61A | 60 | 7 | 0.1337 | 0.6 | 4.0 | 7.2 | 88.2 | 1919 | 87.2 | 1913 | 9.0 |
| 61B | 60 | 7 | 0.1306 | 0.6 | 5.2 | 7.8 | 86.3 | 1907 | | | 8.8 |
| 62A | 85 | 7 | 0.1532 | 0.5 | 5.4 | 9.3 | 84.8 | 872 | 85.4 | 874 | 10.3 |
| 62B | 85 | 7 | 0.1626 | 0.5 | 4.6 | 8.9 | 86.0 | 876 | | | 11.0 |
| 63A | 110 | 7 | 0.1944 | 0.4 | 4.9 | 8.8 | 85.9 | 507 | 86.2 | 520 | 13.1 |
| 63B | 110 | 7 | 0.2602 | 0.3 | 4.7 | 8.5 | 86.4 | 532 | | | 17.6 |
| 64A | 60 | 8 | 0.1246 | 0.5 | 1.2 | 1.0 | 97.3 | 583 | 96.6 | 588 | 8.4 |
| 64B | 60 | 8 | 0.1245 | 0.5 | 1.9 | 1.8 | 96.0 | 593 | | | 8.4 |
| 65A | 85 | 8 | 0.4319 | 0.2 | 1.2 | 0.8 | 97.8 | 369 | 97.8 | 368 | 29.1 |
| 65B | 85 | 8 | 0.4452 | 0.2 | 1.2 | 0.7 | 97.9 | 367 | | | 30.0 |
| 66A | 110 | 8 | 0.8973 | 0.0 | 1.1 | 0.2 | 98.6 | 317 | 98.4 | 317 | 60.5 |
| 66B | 110 | 8 | 0.9322 | 0.1 | 1.4 | 0.3 | 98.2 | 317 | | | 62.9 |
| 67A | 60 | 9 | 0.0323 | 0.0 | 3.3 | 1.3 | 95.4 | 507 | 95.3 | 513 | 2.2 |
| 67B | 60 | 9 | 0.0326 | 0.0 | 3.3 | 1.6 | 95.1 | 518 | | | 2.2 |
| 68A | 85 | 9 | 0.1665 | 0.0 | 3.2 | 0.7 | 96.1 | 330 | 96.4 | 327 | 11.2 |
| 68B | 85 | 9 | 0.1832 | 0.0 | 3.0 | 0.4 | 96.6 | 325 | | | 12.4 |
| 69A | 110 | 9 | 0.1824 | 0.0 | 2.3 | 0.3 | 97.4 | 309 | 97.3 | 307 | 12.3 |
| 69B | 110 | 9 | 0.226 | 0.0 | 2.5 | 0.4 | 97.1 | 306 | | | 15.2 |
| 70A | 60 | 10 | 0.0695 | 0.5 | 1.3 | 1.3 | 96.8 | 794 | 97.5 | 794 | 4.7 |
| 70B | 60 | 10 | 0.0622 | 0.4 | 1.2 | 0.1 | 98.2 | 794 | | | 4.2 |
| 71A | 85 | 10 | 0.0821 | 0.3 | 1.3 | 2.0 | 96.4 | 490 | 96.7 | 489 | 5.5 |
| 71B | 85 | 10 | 0.0913 | 0.3 | 1.1 | 1.7 | 97.0 | 488 | | | 6.2 |
| 72A | 110 | 10 | 0.1419 | 0.1 | 1.2 | 1.2 | 97.4 | 362 | 97.3 | 361 | 9.6 |
| 72B | 110 | 10 | 0.1801 | 0.2 | 1.3 | 1.3 | 97.2 | 360 | | | 12.2 |
| 73A | 60 | 11 | 0.0917 | 0.3 | 0.8 | 1.0 | 97.9 | 636 | 97.3 | 630 | 6.2 |
| 73B | 60 | 11 | 0.092 | 0.4 | 1.4 | 1.5 | 96.7 | 625 | | | 6.2 |
| 74A | 85 | 11 | 0.2414 | 0.1 | 0.9 | 1.1 | 98.0 | 406 | 98.0 | 399 | 16.3 |
| 74B | 85 | 11 | 0.2651 | 0.1 | 0.9 | 1.0 | 98.0 | 393 | | | 17.9 |
| 75A | 110 | 11 | 0.6764 | 0.0 | 1.2 | 0.5 | 98.3 | 317 | 98.3 | 317 | 45.6 |
| 75B | 110 | 11 | 0.6827 | 0.0 | 1.1 | 0.5 | 98.4 | 317 | | | 46.1 |
| 76A | 60 | 12 | 0.039 | — | — | — | — | — | — | — | 2.6 |
| 76B | 60 | 12 | 0.0351 | — | — | — | — | — | | | 2.4 |
| 77A | 85 | 12 | 0.1596 | 0.3 | 1.5 | 0.2 | 98.0 | 344 | 97.8 | 345 | 10.8 |
| 77B | 85 | 12 | 0.1621 | 0.3 | 1.7 | 0.4 | 97.6 | 346 | | | 10.9 |
| 78A | 110 | 12 | 0.2002 | 0.8 | 2.7 | 0.0 | 96.4 | 311 | 97.2 | 313 | 13.5 |
| 78B | 110 | 12 | 0.2236 | 0.3 | 1.7 | 0.0 | 98.0 | 315 | | | 15.1 |
| 79A | 60 | 13 | 0.5464 | 3.4 | 5.3 | 2.3 | 89.0 | 1191 | 91.0 | 1246 | 36.9 |
| 79B | 60 | 13 | 0.5493 | 2.6 | 3.4 | 1.0 | 93.0 | 1301 | | | 37.1 |
| 80A | 85 | 13 | 0.8176 | 1.6 | 4.5 | 0.6 | 93.4 | 550 | 93.3 | 553 | 55.2 |
| 80B | 85 | 13 | 0.8451 | 1.6 | 4.6 | 0.6 | 93.2 | 557 | | | 57.0 |
| 81A | 110 | 13 | 0.9876 | 1.3 | 6.8 | 0.1 | 91.8 | 382 | 91.9 | 383 | 66.6 |
| 81B | 110 | 13 | 0.9961 | 1.2 | 6.7 | 0.1 | 91.9 | 385 | | | 67.2 |
| 82A | 60 | 14 | 0.0467 | — | — | — | — | — | — | — | 3.2 |
| 82B | 60 | 14 | 0.0462 | — | — | — | — | — | | | 3.1 |
| 83A | 85 | 14 | 0.1268 | 4.0 | 3.7 | 1.8 | 90.5 | 854 | 90.4 | 847 | 8.6 |
| 83B | 85 | 14 | 0.1369 | 3.9 | 3.8 | 1.9 | 90.3 | 839 | | | 9.2 |
| 84A | 110 | 14 | 0.0899 | 2.0 | 5.1 | 2.6 | 90.4 | 593 | 90.6 | 585 | 6.1 |
| 84B | 110 | 14 | 0.0912 | 1.6 | 5.0 | 2.4 | 90.9 | 577 | | | 6.2 |
| 85A | 60 | 15 | 0.0207 | — | — | — | — | — | — | — | 1.4 |
| 85B | 60 | 15 | 0.0209 | — | — | — | — | — | | | 1.4 |
| 86A | 85 | 15 | 0.0974 | 0.3 | 1.4 | 0.9 | 97.4 | 365 | 97.6 | 361 | 6.6 |
| 86B | 85 | 15 | 0.1094 | 0.4 | 1.3 | 0.6 | 97.7 | 358 | | | 7.4 |
| 87A | 110 | 15 | 0.2949 | 1.2 | 2.7 | 0.7 | 96.0 | 298 | 97.2 | 305 | 19.9 |
| 87B | 110 | 15 | 0.3415 | 0.3 | 1.2 | 0.1 | 98.4 | 312 | | | 23.0 |
| 88A | 60 | 16 | 0.1052 | 0.5 | 4.2 | 6.8 | 88.6 | 1780 | 89.3 | 1770 | 7.1 |
| 88B | 60 | 16 | 0.1152 | 0.4 | 3.3 | 6.2 | 90.1 | 1760 | | | 7.8 |
| 89A | 85 | 16 | 0.1241 | 0.6 | 4.9 | 8.9 | 85.6 | 857 | 83.9 | 815 | 8.4 |
| 89B | 85 | 16 | 0.1415 | 1.4 | 7.7 | 8.8 | 82.2 | 773 | | | 9.5 |
| 90A | 110 | 16 | 0.1986 | 0.3 | 5.5 | 10.4 | 83.8 | 661 | 85.3 | 586 | 13.4 |
| 90B | 110 | 16 | 0.2248 | 0.4 | 4.6 | 8.2 | 86.8 | 511 | | | 15.2 |
| 91A | 60 | 17 | 0.0195 | — | — | — | — | — | — | — | 1.3 |
| 91B | 60 | 17 | 0.0189 | — | — | — | — | — | | | 1.3 |
| 92A | 85 | 17 | 0.0735 | — | — | — | — | — | — | — | 5.0 |
| 92B | 85 | 17 | 0.0929 | — | — | — | — | — | | | 6.3 |

TABLE 4-continued

Catalyst 0.08 μmol (0.4 mmol/l in toluene), with 0.08 μmol N,N-Dimethylanilinium Tetrakisperfluorophenylborate (BF20) activator (0.4 mmol/l in toluene), about 0.6 μmol of TNOA (0.01 mol/l in isohexane), 2 mL 1-Decene, isohexane solvent, 1 h.

| EX | T (° C.) | MC | Isolated Yield (g) | % Vinylene | % Tri-sub | % Vinyl | % Vinylidene | $M_n$* g/mol | % Vinylidene (avg) | $M_n$* (avg) (g/mol) | Conv %** |
|---|---|---|---|---|---|---|---|---|---|---|---|
| 93A | 110 | 17 | 0.2384 | 0.2 | 1.3 | 0.4 | 98.1 | 314 | 97.1 | 310 | 16.1 |
| 93B | 110 | 17 | 0.2354 | 0.9 | 2.4 | 0.6 | 96.1 | 305 | | | 15.9 |

*$M_n$ estimated by $^1$H NMR;
**Conv % calculated from isolated yield and it is the minimum conversion due to volatility of the dimer product.
"—" indicates insufficient material for analysis or data not available.

1-Decene Polymerizations using N,N-dimethylanilinium tetrakisperfluoronaphthylborate Activator

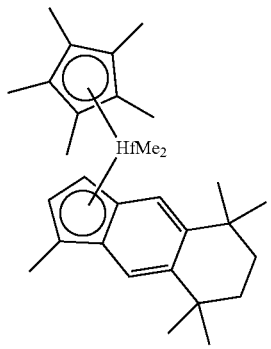

18

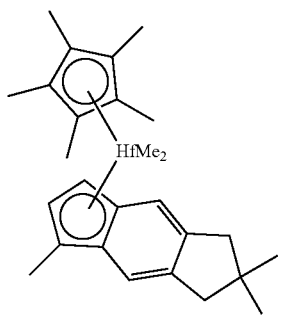

19

Figure 2:
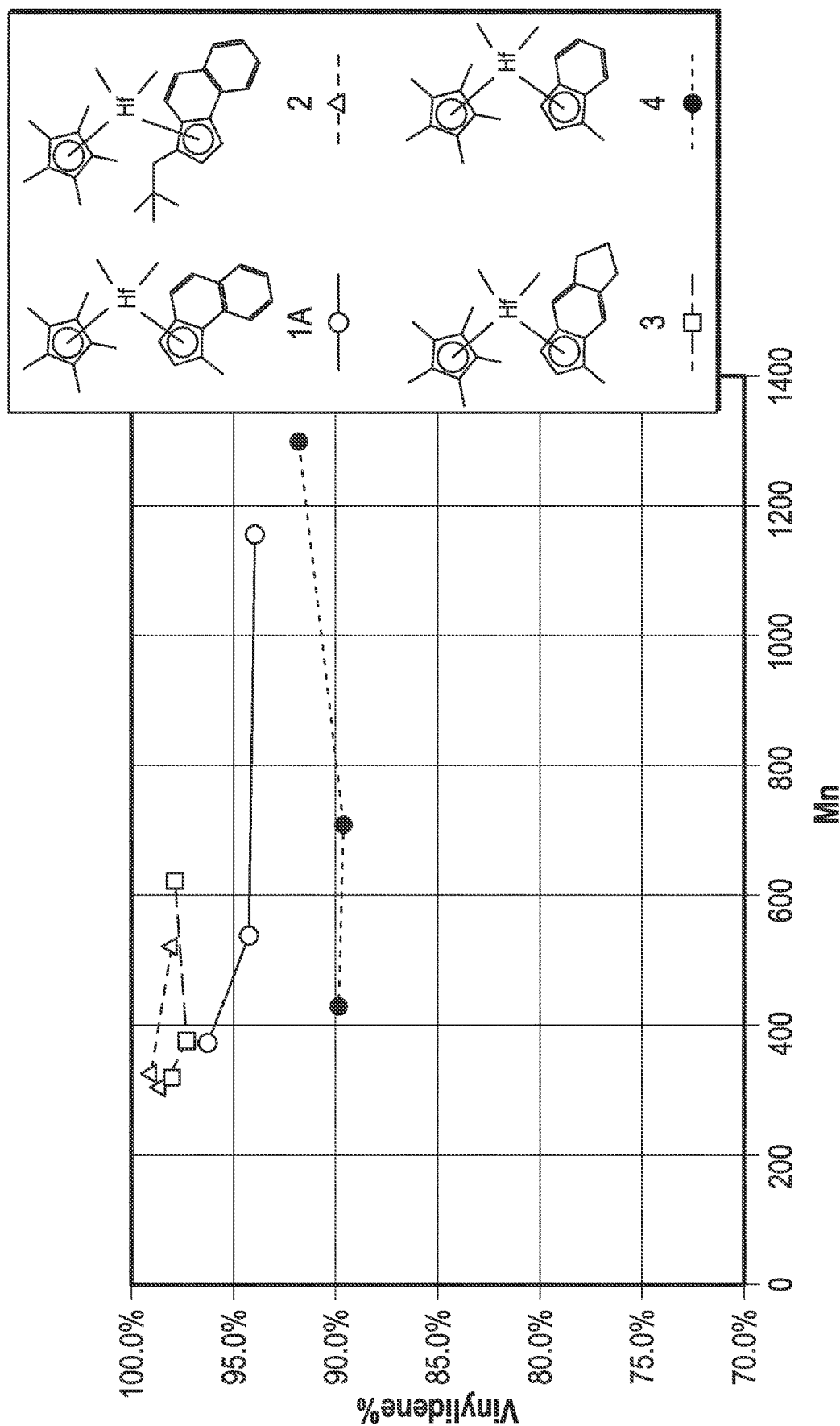
FIG. 2 is a graph comparing mole percent vinylidene versus $M_n$ of 1-decene oligomers produced using catalysts and methods according to embodiments of the invention.

As shown in Tables 3 and 4, and further illustrated in FIGS. 1 and 2, inventive catalysts 2, 3, 6, 8, 9, 10, 11, 12, 14, 15, and 17 have even higher vinylidene selectivity of greater than or equal to 96% than catalyst 1A, which produced PAOs having 93-95.9% vinylidene, across all temperatures tested. Notably, catalysts 2 and 3 also show capabilities for much desired lower $M_n$ in comparison to catalyst 1A, all under similar polymerization conditions using similar drying/isolation procedures. As these data also show, catalyst 4, which is used in other polymerization processes, a 1-Me-indenyl metallocene, was further discovered to be useful for producing low viscosity, low Mn unsaturated PAOs, showing vinylidene terminations of 89-92 mol % under similar conditions. The Zr version of 4, catalyst 12, gives high vinylidene selectivities but has much lower activities in comparison to catalyst 3.

It is considered that even small changes in metallocene compound structure can cause drastic differences in the characteristics of the oligomeric products. For instance, the only difference between metallocene D and metallocene A is a single methyl group, instead of a hydrogen, at the $R^3$ position (alpha to the naphthyl portion of the benzindenyl ring and beta to the $R^1$ methyl group on the cyclopentadienyl portion of the benzindenyl ring). Despite that relatively small structural difference, as shown in Table I (Ex. 13-14 vs. Ex. 1-2), using same activator (dimethylanilinium tetrakisperfluorophenylborate) and under same conditions, a catalyst system comprising metallocene D can be seen to produce a uPAO product having a significant vinyl content, whereas a catalyst system comprising metallocene A can be seen to produce a uPAO product having an extraordinarily high vinylidene content (and very little vinyl content). A similar trend has been observed using dimethylanilinium tetrakisperfluoronaphthylborate as an activator (Table II, Ex. 40-42 vs. Ex. 37-39). These results show both the unexpect-

TABLE 5

Catalyst 0.04 μmol (0.8 mmol/l in toluene), with 0.04 μmol N,N-dimethylanilinium tetrakis(perfluoronaphthyl)borate as activator (0.8 mmol/l in toluene), about 0.6 μmol of TNOA (0.01 mol/l in isohexane), 2 mL 1-decene, isohexane solvent, 1 h.

| EX | T (° C.) | MC | Isolated Yield (g) | % Vinylene | % Tri-sub | % Vinyl | % Vinylidene | $M_n$* g/mol | % Vinylidene (avg) | $M_n$* (avg) (g/mol) | Conv %** |
|---|---|---|---|---|---|---|---|---|---|---|---|
| 94A | 85 | 18 | 0.0594 | 0.5% | 6.3 | 5.1 | 88.2 | 521 | 87.6 | 533 | 4.0 |
| 94B | 85 | 18 | 0.0539 | 0.6% | 7.2 | 5.2 | 87.0 | 546 | | | 3.6 |
| 95A | 85 | 19 | 0.1231 | 0.7% | 4.3 | 3.8 | 91.3 | 492 | 91.5 | 496 | 8.3 |
| 95B | 85 | 19 | 0.1287 | 0.6% | 4.2 | 3.5 | 91.7 | 501 | | | 8.7 |

*$M_n$ estimated by $^1$H NMR.
**Conv % calculated from isolated yield and it is the minimum conversion due to volatility of the dimer product.

edness of the uPAO product characteristics and the unpredictability of the effect of ligand structure change on metallocene catalysis.

All documents described herein are incorporated by reference herein for purposes of all jurisdictions where such practice is allowed, including any priority documents, related applications, and/or testing procedures to the extent they are not inconsistent with this text, provided however that any priority document not named in the initially filed application or filing documents is not incorporated by reference herein. As should be apparent from the foregoing general description and the specific embodiments, while forms of the invention have been illustrated and described, various modifications can be made without departing from the spirit and scope of the invention. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the invention, and all such modifications are intended to be included within the scope of the invention. Accordingly, it is not intended that the invention be limited thereby. Likewise, the term "comprising" is considered synonymous with the terms "including" and "containing." Also, whenever a composition, an element, or a group of elements is preceded with the transitional phrase "comprising," it should be understood that the same composition or group of elements is contemplated with transitional phrases "consisting essentially of," "consisting of," "selected from the group of consisting of," or "is" preceding the recitation of the composition, element, or elements, and vice versa.

What is claimed is:

1. An unsaturated poly alpha-olefin (PAO) product comprising:
   greater than or equal to about 80 mol % vinylidenes, based on total moles of vinyls, vinylidenes, di-substituted vinylenes, and tri-substituted vinylenes contained therein;
   0.1 mol % to 3.5 mol % of tri-substituted vinylenes;
   3.0 mol % or less of di-substituted vinylenes;
   3.0 mol % or less of vinyl groups; based on total moles of vinylidenes, tri-substituted vinylenes, di-substituted vinylenes, and vinylidenes contained therein;
   and having an Mn of less than 5000 g/mol as determined by $^1$H NMR.

2. The unsaturated poly alpha-olefin (PAO) product of claim 1 further comprising:
   96.5 mol % to 99.9 mol % of vinylidenes; and
   a number average molecular weight (Mn) of 1500 g/mol or less as measured by $^1$H NMR.

3. The unsaturated poly alpha-olefin (PAO) product of claim 1 further comprising:
   less than or equal to about 1.0 mol % di-substituted vinylenes, when present;
   less than or equal to about 1.0 mol % vinyl groups when present; and
   a number average molecular weight (Mn) of 1000 g/mol or less as measured by $^1$H NMR.

4. The unsaturated poly alpha-olefin (PAO) product of claim 1 further comprising greater than or equal to about 80 mol % vinylidenes, based on total moles of vinyls, vinylidenes, di-substituted vinylenes, and tri-substituted vinylenes contained therein, and from 98 mol % to 99.5 mol % of a combination of vinylidenes and tri-substituted vinylenes; 0.5 mol % to 2 mol % of a combination of di-substituted vinylenes and vinyl groups; and a number average molecular weight (Mn) of 800 g/mol or less as measured by $^1$HNMR.

5. The unsaturated poly alpha-olefin product of claim 3 wherein the unsaturated poly alpha-olefin product is dimer.

6. The unsaturated poly alpha-olefin product of claim 4 wherein the unsaturated poly alpha-olefin product is dimer.

7. The unsaturated poly alpha-olefin (PAO) product of claim 1 wherein the PAO product comprises greater than or equal to about 90 mol % vinylidenes, based on total moles of vinyls, vinylidenes, di-substituted vinylenes, and tri-substituted vinylenes contained therein and having an Mn of less than 5000 g/mol as determined by $^1$H NMR.

8. A process for making a poly alpha-olefin, PAO, the process comprising:
   contacting a feed comprising a C6-C32 alpha-olefin with a catalyst system comprising a metallocene compound in a polymerization reactor under polymerization conditions to effect a polymerization reaction to obtain a polymerization reaction mixture comprising vinylidenes, tri-substituted vinylenes, optionally di-substituted vinylenes, and optionally vinyls; and
   obtaining an unsaturated PAO product from the polymerization reaction mixture, wherein the unsaturated PAO product comprises greater than or equal to about 80 mol % vinylidenes, based on total moles of vinyls, vinylidenes, di-substituted vinylenes, and tri-substituted vinylenes contained therein, 0.1 mol % to 3.5 mol % of tri-substituted vinylenes, 3.0 mol % or less of di-substituted vinylenes, 3.0 mol % or less of vinyl groups; based on total moles of vinylidenes, tri-substituted vinylenes, di-substituted vinylenes, and vinylidenes contained therein, and having an Mn of less than 5000 g/mol as determined by $^1$H NMR,
   wherein the conversion is about 10% or more and the polymerization reaction exhibits a selectivity toward greater than or equal to about 80 mol % vinylidenes, based on total moles of vinyls, vinylidenes, di-substituted vinylenes, and tri-substituted vinylenes in the unsaturated PAO product,
   wherein the metallocene compound is represented by formula (F-MC):

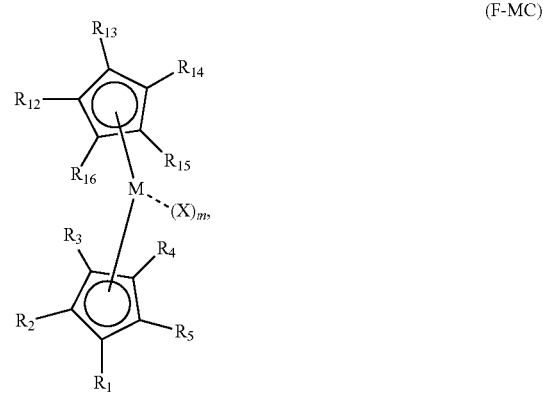

wherein:
   $R^2$ is hydrogen and one of $R^1$ and $R^3$ is a substituted or unsubstituted linear, branched, or cyclic $C_1$-$C_6$ hydrocarbyl group, and the other one of $R^1$ and $R^3$ is a hydrogen;

$R^4$ and $R^5$ taken together with the carbon atoms in the cyclopentadienyl ring to which they are directly connected, collectively form one or more substituted or unsubstituted rings annulated to the cyclopentadienyl ring;

$R^{12}$, $R^{13}$, $R^{14}$, $R^{15}$, and $R^{16}$ are each independently a hydrogen, or a substituted or unsubstituted linear, branched, or cyclic $C_1$-$C_{20}$ hydrocarbyl, silylcarbyl, or germanyl group, and optionally at least three of $R^{12}$, $R^{13}$, $R^{14}$, $R^{15}$, and $R^{16}$ are not hydrogen;

M is a group 3, 4 or 5 transition metal having an integer coordination number of v; wherein v is 3, 4, or 5, each X is independently a halogen, a hydride, an amide, an alkoxide, or a $C_1$-$C_{20}$ substituted or unsubstituted linear, branched, or cyclic hydrocarbyl group, or optionally two or more X moieties together form a fused ring or ring system; and m is an integer equal to v-2.

9. The process of claim 8, wherein:

one of substituted hydrocarbyls $R^1$ and $R^3$ comprise an alpha Group 14 atom directly attached to the indenyl ring, a beta Group 14 atom attached to the alpha atom, and two or more, substituted or unsubstituted linear, branched linear, or cyclic $C_1$-$C_8$ hydrocarbyl groups attached to the beta atom.

10. The process of claim 8, wherein the metallocene compound is represented by formula (II):

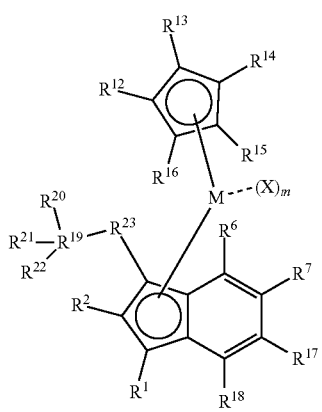

(II)

wherein:

$R^1$ and $R^2$ are hydrogen;

$R^3$ comprises $R^{23}$ and $R^{19}$ which comprise one or more Group 14 atoms;

$R^{20}$, $R^{21}$, and $R^{22}$ are independently hydrogen or a substituted or unsubstituted linear, branched, or cyclic $C_1$-$C_{20}$ hydrocarbyl group and at least two of $R^{20}$, $R^{21}$, and $R^{22}$ are independently a substituted or unsubstituted linear, branched, or cyclic $C_1$-$C_{20}$ hydrocarbyl group, wherein at least two of $R^{20}$, $R^{21}$, and $R^{22}$ are a substituted or unsubstituted linear, branched, or cyclic $C_1$-$C_{20}$ hydrocarbyl group;

$R^6$, $R^7$, $R^{17}$, and $R^{18}$ are each independently hydrogen; a substituted or unsubstituted linear, branched, or cyclic $C_1$-$C_{30}$ hydrocarbyl group; or $R^6$ and $R^7$, $R^7$ and $R^{17}$, or $R^{17}$ and $R^{18}$, taken together with the carbon atoms in the indenyl ring to which they are directly connected, collectively form one or more substituted or unsubstituted rings annulated to the indenyl ring;

$R^{12}$, $R^{13}$, $R^{14}$, $R^{15}$ and $R^{16}$ are each independently a substituted or unsubstituted linear, branched, or cyclic $C_1$-$C_8$ hydrocarbyl group;

each X is independently a halogen, a hydride, an amide, an alkoxide, or a $C_1$-$C_{20}$ substituted or unsubstituted linear, branched, or cyclic hydrocarbyl group, or two or more X moieties together form a fused ring or ring system;

M is a group 3, 4 or 5 transition metal having an integer coordination number of v; wherein v is 3, 4, or 5, and m is an integer equal to v-2.

11. The process of claim 9, wherein:

one of substituted hydrocarbyls $R^1$ and $R^3$ comprise an alpha Group 14 atom directly attached to the indenyl ring, a beta Group 14 atom attached to the alpha atom, and two or more, substituted or unsubstituted linear, branched linear, or cyclic $C_1$-$C_8$ hydrocarbyl groups attached to the beta atom.

12. The process of claim 10, wherein $R^{23}$ and $R^{19}$ comprise one or more silicon atoms.

* * * * *